United States Patent [19]

Hayashi et al.

[11] Patent Number: 4,479,966
[45] Date of Patent: Oct. 30, 1984

[54] 6,9-METHANO-PGI2 ANALOGUES

[75] Inventors: Masaki Hayashi; Yoshitaka Konishi, both of Takatsuki; Yoshinobu Arai, Toyonaka, all of Japan

[73] Assignee: Ono Pharmaceutical Company, Ltd., Osaka, Japan

[21] Appl. No.: 113,502

[22] Filed: Jan. 21, 1980

Related U.S. Application Data

[62] Division of Ser. No. 025,096, Mar. 29, 1979, abandoned.

[30] Foreign Application Priority Data

Mar. 31, 1978 [JP] Japan ................................ 53-037952
Nov. 10, 1978 [JP] Japan ................................ 53-137867

[51] Int. Cl.³ .................... C07C 177/00; C07C 59/46; A01K 31/557
[52] U.S. Cl. .................................... 424/305; 536/46; 549/66; 549/415; 549/422; 549/473; 549/475; 556/441; 560/56; 560/100; 560/102; 560/107; 560/116; 560/119; 560/227; 560/228; 560/256; 562/498; 562/501; 562/466; 424/317
[58] Field of Search ................ 424/305, 317; 536/46; 542/426; 549/66, 415, 422, 473, 475; 556/441; 560/560, 100, 102, 107, 116, 119, 227, 228, 256; 562/498, 501, 466

[56] References Cited

FOREIGN PATENT DOCUMENTS 2013001 8/1979 United Kingdom ................ 560/119

*Primary Examiner*—Robert Gerstl
*Attorney, Agent, or Firm*—John F. Witherspoon

[57] ABSTRACT

Prostaglandin I₂ analogues of the formula:

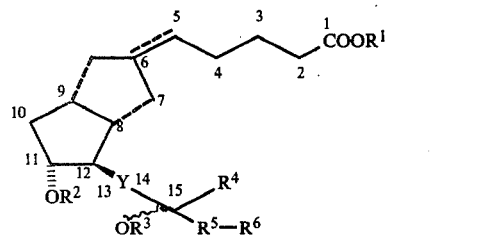

[wherein the symbol ≒ between the carbon atoms in positions 5 and 6 represents a single or double bond, Y represents ethylene or trans-vinylene, $R^1$ represents hydrogen, alkyl of 1 to 12 carbon atoms, aralkyl of 7 to 12 carbon atoms, cycloalkyl of 4 to 7 carbon atoms optionally substituted by alkyl of 1 to 4 carbon atoms, phenyl optionally substituted by chlorine, trifluoromethyl, alkyl of 1 to 4 carbon atoms or phenyl, a —$C_mH_{2m}COOR^7$ group (wherein m represents an integer of from 1 to 12 and $R^7$ represents alkyl of 1 to 4 carbon atoms), a —$C_nH_{2n}OR^8$ group (wherein n represents an integer of from 2 to 12 and $R^8$ represents hydrogen or alkyl of 1 to 4 carbon atoms) or a

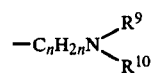

group (wherein $R^9$ and $R^{10}$ each represent alkyl of 1 to 4 carbon atoms and n is as hereinbefore defined), $R^2$ represents hydrogen or a hydroxy-protecting group, $R^3$ represents hydrogen or a hydroxy-protecting group which is eliminated under acidic conditions, $R^4$ represents hydrogen, methyl or ethyl, $R^5$ represents a single bond or alkylene of 1 to 4 carbon atoms optionally substituted by a chlorine atom (provided that, when $R^5$ is alkylene substituted by chlorine, $R^6$ represents hydrogen or alkyl) $R^6$ represents hydrogen, alkyl or 1 to 8 carbon atoms, cycloalkyl of 4 to 7 carbon atoms optionally substituted by alkyl of 1 to 8 carbon atoms, or phenyl or phenoxy optionally substituted by chlorine, trifluoromethyl or alkyl of 1 to 4 carbon atoms, and when ≒ represents a double bond that bond is E, Z or a mixture thereof and when, ≒ represents a single bond, the absolute configuration of $C_6$ is R, S or a mixture thereof] and, when $R^2$ and $R^3$ represent hydrogen, cyclodextrin clathrates of such acids and esters and, when $R^1$, $R^2$ and $R^3$ represent hydrogen, non-toxic salts thereof and, when $R^1$ represents

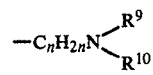

in which n, $R^9$ and $R^{10}$ are as hereinbefore defined, non-toxic acid addition salts thereof, are new compounds, possessing prostaglandin-like activity.

40 Claims, No Drawings

6,9-METHANO-PGI2 ANALOGUES

DESCRIPTION

This is a division of application Ser. No. 25,096 filed Mar. 29, 1979, now abandoned.

This invention relates to new prostaglandin I₂ (PGI₂) analogues, to a process for their preparation and to pharmaceutical compositions containing them.

PGI₂ is a physiologically active substance having the following formula:

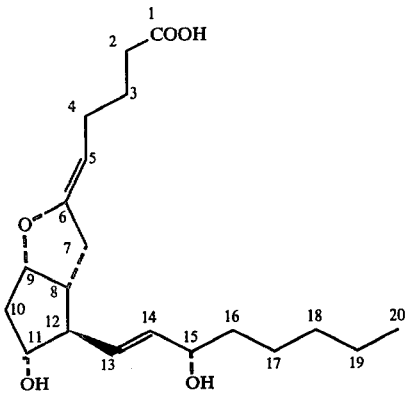

I and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI₂ can be prepared by incubation of prostaglandin G₂ (PGG₂) or prostaglandin H₂ (PGH₂) with microsomal fractions prepared from thoracic aorta of swine, mesenteric artery of swine, rabbit aorta or the stomach fundus of rats. PGI₂ has a relaxing activity on the artery, which is peculiar to the artery and which does not operate on other smooth muscle. Furthermore, PGI₂ strongly inhibits arachidonic acid-induced blood platelet aggregation of the human.

Taking into consideration that thromboxane A₂ prepared by incubation of PGG₂ or PGH₂ with blood platelet microsome, has a contracting activity on the artery and an aggregating activity on blood platelets, the properties of PGI₂ heretofore mentioned show that PGI₂ fulfils a very important physiological part in a living body. PGI₂ may be useful in the treatment of arteriosclerosis, cardiac failure or thrombosis.

Widespread investigations have been carried out in order to discover inter alia new products possessing the pharmacological properties of the 'natural' PGI₂ or one or more of such properties to an enhanced degree, or hitherto unknown pharmacological properties. As a result of extensive research and experimentation it has now been discovered that by replacing the 6,9-epoxy group of PGI₂ and certain analogues thereof by a 6,9-methano group, the pharmacological properties of the 'natural' PGI₂ are, in some aspects of its activities, improved or modified.

The present invention accordingly provides new prostaglandin I₂ analogues of the general formula:

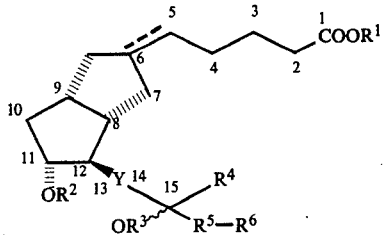

II

[wherein the symbol ===== between the carbon atoms in positions 5 and 6 represents a single or, preferably, a double bond, Y represents ethylene (i.e. —CH₂CH₂—) or, preferably, trans-vinylene (i.e.

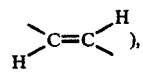

), $R^1$ represents a hydrogen atom, a straight- or branched-chain alkyl group containing from 1 to 12 carbon atoms, an aralkyl group containing from 7 to 12 carbon atoms, a cycloalkyl group containing from 4 to 7 carbon atoms unsubstituted or substituted by at least one straight- or branched-chain alkyl group containing from 1 to 4 carbon atoms, a phenyl group unsubstituted or substituted by at least one chlorine atom, trifluoromethyl group, alkyl group containing from 1 to 4 carbon atoms or phenyl group, a —$C_mH_{2m}COOR^7$ group (wherein m represents an integer of from 1 to 12 and $R^7$ represents a straight- or branched-chain alkyl group containing from 1 to 4 carbon atoms), a —$C_nH_{2n}OR^8$ group (wherein n represents an integer of from 2 to 12 and $R^8$ represents a hydrogen atom or a straight- or branched-chain alkyl group containing from 1 to 4 carbon atoms) or a

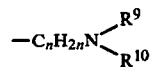

group (wherein $R^9$ and $R^{10}$, which may be the same or different, each represent a straight- or branched-chain alkyl group containing from 1 to 4 carbon atoms and n is as hereinbefore defined), $R^2$ represents a hydrogen atom or a hydroxy-protecting group which is eliminated under acidic or alkaline conditions, $R^3$ represents a hydrogen atom or a hydroxy-protecting group which is eliminated under acidic conditions, $R^4$ represents a hydrogen atom or a methyl or ethyl group, $R^5$ represents a single bond or a straight- or branched-chain alkylene group containing from 1 to 4 carbon atoms unsubstituted or substituted by a chlorine atom (provided that, when $R^5$ is an alkylene group substituted by a chlorine atom, $R^6$ represents a hydrogen atom or an alkyl group), $R^6$ represents a hydrogen atom, a straight- or branched-chain alkyl group containing from 1 to 8 carbon atoms, a cycloalkyl group containing from 4 to 7 carbon atoms unsubstituted or substituted by at least one straight- or branched-chain alkyl group containing from 1 to 8 carbon atoms, or a phenyl or phenoxy group unsubstituted or substituted by at least one chlorine atom, trifluoromethyl group or straight- or branched-chain alkyl group containing from 1 to 4 carbon atoms, the wavy line ⁓⁓⁓ attached to the carbon atom in position 15 represents α- or β-configuration (i.e. S- or R-configuration) or a mixture thereof and when ≅≅≅ represents a double bond, the double bond between $C_5$–$C_6$ is E, Z or a mixture thereof (i.e. EZ) and, when ≅≅≅ represents a single bond, the absolute configuration of $C_6$ is R, S or a mixture thereof (i.e. RS)] and, when $R^2$ and $R^3$ represent hydrogen atoms, cyclodextrin clathrates of such acids and esters and, when $R^1$, $R^2$ and $R^3$ represent hydrogen atoms, non-toxic (e.g. sodium) salts thereof and, when $R^1$ represents a

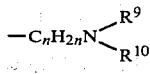

group in which n, $R^9$ and $R^{10}$ are as hereinbefore defined, non-toxic acid addition salts thereof. Preferably the hydroxy group or the protected-hydroxy group attached to the C-15 carbon atom in formula II is in α-configuration.

The present invention is concerned with all compounds of general formula II in the 'natural' form or its enantiomeric form, or mixtures thereof, more particularly the racemic form consisting of equimolecular mixtures of natural and its enantiomeric form.

As will be apparent to those skilled in the art, the compounds depicted in general formula II have at least five centres of chirality, these five centres of chirality being at C-8, C-9, C-11, C-12 and C-15 carbon atoms. Still further centres of chirality may occur when $R^1$ or $R^6$ is a branched-chain alkyl group or $R^5$ or a $C_mH_{2m}$ or $C_nH_{2n}$ moiety is a branched-chain alkylene group. The presence of chirality leads, as is well known, to the existence of isomerism. However, the compounds of general formula II all have such a configuration that the substituent groups attached to the ring carbon atoms in the positions identified as 8 and 9 are cis with respect to each other and that the substituent groups attached to the ring carbon atoms in the positions identified as 8 and 12 are trans with respect to each other. Accordingly, all isomers of general formula II and mixtures thereof which have those substituent groups attached to the ring carbon atoms in positions 8 and 9 in the cis-configuration, those attached in positions 8 and 12 in the trans-configuration and the group $OR^2$ as depicted in the 11-position and the group $OR^3$ as depicted in the 15-position are to be considered within the scope of general formula II.

Examples of the straight- or branched-chain alkyl group containing from 1 to 12 carbon atoms represented by $R^1$ are methyl, ethyl, propyl, butyl, pentyl, hexyl, heptyl, octyl, nonyl, decyl, undecyl and dodecyl and their isomers.

Examples of the aralkyl group containing from 7 to 12 carbon atoms represented by $R^1$ are benzyl, 1-phenylethyl, 2-phenylethyl, 3-phenylbutyl, 4-phenylbutyl, 1-(2-naphthyl)ethyl and 2-(1-naphthyl)ethyl.

Examples of the cycloalkyl group containing from 4 to 7 carbon atoms unsubstituted or substituted by at least one straight- or branched-chain alkyl group containing from 1 to 4 carbon atoms represented by $R^1$ are cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, 2,6-dimethyl-4-propylcyclohexyl and cycloheptyl.

Examples of the phenyl group unsubstituted or substituted by at least one chlorine atom, trifluoromethyl group, straight- or branched-chain alkyl group containing from 1 to 4 carbon atoms or phenyl group represented by $R^1$ are phenyl, 2-chlorophenyl, 3-chlorophenyl, 4-chlorophenyl, 2,4-dichlorophenyl, 2,4,6-trichlorophenyl, 2-tolyl, 3-tolyl, 4-tolyl, 4-ethylphenyl, 4-tert-butylphenyl, 4-sec-butylphenyl, 3-trifluoromethylphenyl and 4-biphenyl.

Examples of the $C_mH_{2m}$ or $C_nH_{2n}$ moiety of the $C_mH_{2m}COOR^7$, $C_nH_{2n}OR^8$ and

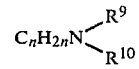

groups represented by $R^1$ are methylene (when m in the —$C_mH_{2m}$— moiety is 1), ethylene, trimethylene, tetramethylene, pentamethylene, hexamethylene, heptamethylene, octamethylene, nonamethylene, decamethylene, undecamethylene, dodecamethylene and their isomers.

Examples of the straight- or branched-chain alkyl group containing from 1 to 4 carbon atoms represented by $R^7$, $R^8$, $R^9$ and $R^{10}$ are methyl, ethyl, propyl, isopropyl, butyl, isobutyl, sec-butyl and tert-butyl.

Preferably $R^1$ is a hydrogen atom or a straight- or branched-chain alkyl group containing from 1 to 4 carbon atoms, most preferably a hydrogen atom or a methyl group.

It is to be understood that by the term "hydroxy-protecting group" as used in this specification and the accompanying claims is meant a group which may be removed under conditions which do not substantially affect the rest of the molecule. The hydroxy-protecting groups, represented by $R^2$ and $R^3$, which are eliminated under acidic conditions, include protecting groups which are easily eliminated under mild acidic conditions, for example, (1) heterocyclic groups such as the tetrahydropyran-2-yl, tetrahydrofuran-2-yl, and tetrahydrothiopyran-2-yl groups, (2) ether groups such as the 1-ethoxyethyl, (1-methoxy-1-methyl)ethyl, 1-methoxy-cyclohexyl and (1-methoxy-1-phenyl)ethyl groups, (3) tri-substituted silyl groups such as the trimethylsilyl, triethylsilyl, tri-n-butylsilyl, tert-butyldimethylsilyl, tribenzylsilyl and triphenylsilyl groups.

Examples of the hydroxy-protecting groups, represented by $R^2$, which are eliminated under alkaline conditions, are acyl groups such as acetyl, chloroacetyl, dichloroacetyl, trichloroacetyl, trifluoroacetyl, propionyl, benzoyl, p-phenylbenzoyl or naphthyloyl.

Preferably $R^2$ and $R^3$ both represent hydrogen atoms, $R^2$ and $R^3$ both represent tetrahydropyran-2-yl groups or $R^2$ represents a tetrahydropyran-2-yl group and $R^3$ represents a hydrogen atom.

Preferably the grouping —$R^5$—$R^6$ represents, e.g. pentyl, 1-chloropentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, 1-propylcyclobutyl, 1-butylcyclobutyl, 1-pentylcyclobutyl, 1-hexylcyclobutyl, 2- methylcyclobutyl, 2-propylcyclobutyl, 3-ethylcyclobutyl, 3-propylcyclobutyl, 2,3,4-triethylcyclobutyl, cyclopentyl, cyclopentylmethyl, 1-cyclopentylethyl, 2-cyclopentylethyl, 2-cyclopentylpropyl, 3-cyclopentylpropyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, 3-cyclohexylpropyl, (1-methyl-2-cyclohexyl)ethyl, 2-cyclohexylpropyl, (1-methyl-2-cyclohexyl)ethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl, 1-methylcyclohexylmethyl, cycloheptyl, cycloheptylmethyl, 1-cycloheptylethyl, 2-cycloheptylethyl, phenyl, benzyl, 1-phenethyl, 2-phenethyl, phenoxymethyl, 2-chlorophenoxymethyl, 3-chlorophenoxymethyl, 4-chlorophenoxymethyl, 2,4-dichlorophenoxymethyl, 2,4,6-trichlorophenoxymethyl, 3-trifluoromethylphenoxymethyl, 2-methylphenoxymethyl, 3-methylphenoxymethyl, 4-methylphenoxymethyl, 4-ethylphenoxymethyl, 4-tert-butylphenoxymethyl, 4-sec-butylphenoxymethyl.

Particularly preferred groupings represented by —R$^5$—R$^6$ are n-pentyl or n-hexyl unsubstituted or substituted by a chlorine atom or a methyl group, or a cyclobutyl, cyclopentyl or cyclohexyl group unsubstituted or substituted by a methyl, ethyl or propyl group, or a chlorophenoxymethyl group, especially n-pentyl, 1-chloropentyl, 1-methylpentyl, 2-methylhexyl, 3-ethylcyclobutyl, cyclopentyl, 3-ethylcyclopentyl, 3-propylcyclopentyl, cyclohexyl, 4-methylcyclohexyl and 3-chlorophenoxymethyl.

According to a feature of the present invention, the prostaglandin I$_2$ analogues of general formula II, wherein Y represents trans-vinylene, R$^1$ represents a straight- or branched-chain alkyl group containing from 1 to 12 carbon atoms, R$^2$ and R$^3$ represent hydrogen atoms and the other symbols are as hereinbefore defined, i.e. compounds of the general formula:

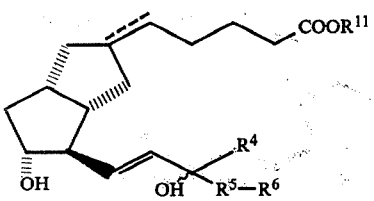

(wherein R$^{11}$ represents a straight- or branched-chain alkyl group containing from 1 to 12 carbon atoms and the other symbols are as hereinbefore defined), may be prepared by the process which comprises hydrolysing to a hydroxy group the group OR$^{12}$ of a compound of the general formula:

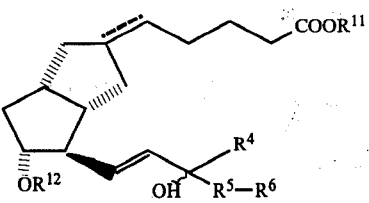

wherein R$^{12}$ represents a hydroxy-protecting group which is eliminated under acidic conditions and the other symbols are as hereinbefore defined. The group OR$^{12}$ of the compounds of general formula IVA may be converted to the hydroxy group by mild acidic hydrolysis with (1) an aqueous solution of an organic acid such as acetic acid, propionic acid, oxalic acid or p-toluenesulphonic acid, or an aqueous solution of an inorganic acid such as hydrochloric acid, sulphuric acid or phosphoric acid, advantageously in the presence of an inert organic solvent miscible with water, e.g. a lower alkanol such as methanol or ethanol, preferably methanol, or an ether such as 1,2-dimethoxyethane, dioxane or tetrahydrofuran, preferably tetrahydrofuran, at a temperature from ambient to 75° C., preferably at a temperature from ambient to 45° C., or (2) an anhydrous solution of an organic acid such as p-toluenesulphonic acid or trifluoroacetic acid in a lower alkanol such as methanol or ethanol at a temperature from 10° to 45° C., or (3) an anhydrous solution of p-toluenesulphonic acid-pyridine complex in a lower alkanol such as methanol or ethanol at a temperature from 10° to 60° C. Advantageously the mild hydrolysis under acidic conditions may be carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, a mixture of p-toluenesulphonic acid and methanol or a mixture of p-toluenesulphonic acid-pyridine complex and methanol.

Compounds of general formula III may be converted to compounds of general formula II, wherein Y represents trans-vinylene, R$^1$, R$^2$ and R$^3$ represent hydrogen atoms and the other symbols are as hereinbefore defined, i.e. compounds of the general formula:

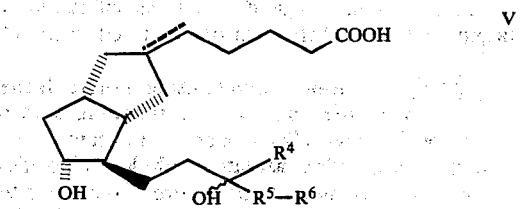

(wherein the various symbols are as hereinbefore defined) by reaction with an aqueous solution of an alkali metal, e.g. sodium or potassium, or an alkaline earth metal, e.g. calcium or barium, hydroxide or carbonate in the presence of a water-miscible solvent, e.g. an ether such as dioxan or tetrahydrofuran or a lower alkanol such as methanol or ethanol at a temperature from −10° to 70° C. preferably at ambient temperature.

Compounds of general formula V may be converted to compounds of general formula II, wherein Y represents trans-vinylene, R$^1$ is other than a hydrogen atom, R$^2$ and R$^3$ represents hydrogen atoms and the other symbols are as hereinbefore defined, i.e. compounds of the general formula:

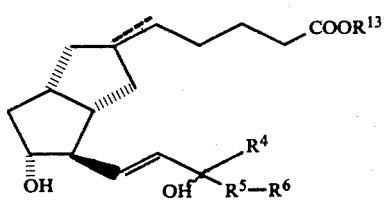

[wherein $R^{13}$ represents a straight- or branched-chain alkyl group containing from 1 to 12 carbon atoms, an aralkyl group containing from 7 to 12 carbon atoms, a cycloalkyl group containing from 4 to 7 carbon atoms unsubstituted or substituted by at least one straight- or branched-chain alkyl group containing from 1 to 4 carbon atoms, a phenyl group unsubstituted or substituted by at least one chlorine atom, trifluoromethyl group, alkyl group containing from 1 to 4 carbon atoms or phenyl group, a group $-C_mH_{2m}COOR^7$, $-C_nH_{2n}OR^8$ or

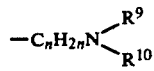

(in which the various symbols are as hereinbefore defined), and the other symbols are as hereinbefore defined] by esterification by methods known per se. The esterification may be carried out for example, when $R^{13}$ represents an alkyl group, using (1) a diazoalkane, (2) an alkyl halide, or (3) an N,N-dimethylformamide-dialkyl acetal, or when $R^{13}$ represents an alkyl, aralkyl, cycloalkyl, phenyl, $-C_mH_{2m}COOR^7$, $-C_nH_{2n}OR^8$ or

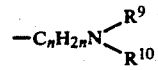

group, using (4) dicyclohexylcarbodiimide (by the procedure described in our Japanese Pat. No. 762305) (5) a pivaloyl halide (by the procedure described in our British Pat. No. 1,364,125), or (6) an arylsulphonyl or alkylsulphonyl halide (by the procedure described in our British Pat. No. 1,362,956). By the expression "methods known per se" as used in this specification is meant methods heretofore used or described in the chemical literature.

The preparation of esters using a diazoalkane is carried out by reacting the corresponding acid with an appropriate diazoalkane in an inert organic solvent, e.g. diethyl ether, ethyl acetate, methylene chloride or acetone, or a mixture of two or more of them, at a temperature from $-10°$ C. to ambient, preferably $0°$ C. The preparation of esters using an alkyl halide is carried out by reacting the corresponding acid with an appropriate alkyl halide, e.g. methyl iodide, (i) in acetone in the presence of a carbonate of an alkali metal such as potassium carbonate [cf. J. Org. Chem., 34, 3717 (1969)], (ii) in N,N-dimethylacetamide or N,N-dimethylformamide in the presence of a bicarbonate of an alkali metal such as sodium or potassium bicarbonate [cf. Advan. Org. Chem., 5, 37 (1965)], or (iii) in dimethyl sulphoxide in the presence of calcium oxide at a temperature from $0°$ C. to ambient [Synthesis, 262 (1972)]. The preparation of esters using an N,N-dimethylformamide-dialkyl acetal is carried out by reacting the corresponding acid with an N,N-dimethylformamide-dialkyl acetal, e.g. N,N-dimethylformamide-dimethyl acetal, in anhydrous benzene at a temperature from $0°$ C. to ambient [cf. Helv. Chem. Acta., 48, 1746 (1965)]. The preparation of esters using dicyclohexylcarbodiimide is carried out by reacting the corresponding acid with the appropriate alcohol in an inert organic solvent, e.g. a halogenated hydrocarbon such as chloroform or methylene chloride in the presence of a base such as pyridine or picoline, preferably pyridine, at a temperature from $0°$ C. to ambient. The preparation of esters using a pivaloyl halide, arylsulphonyl halide or alkylsulphonyl halide is carried out by reacting the corresponding acid with a tertiary amine, e.g. triethylamine, or pyridine and a pivaloyl halide (e.g. pivaloyl chloride, arylsulphonyl halide (e.g. benzenesulphonyl chloride or p-toluenesulphonyl chloride) or an alkylsulphonyl halide (e.g. methanesulphonyl chloride or ethanesulphonyl chloride) in the presence or absence of an inert organic solvent such as a halogenated hydrocarbon, e.g. chloroform or methylene chloride, or diethyl ether to prepare a mixed acid anhydride, and adding thereto an appropriate alcohol at a temperature from $0°$ C. to ambient.

Compounds of general formula V may also be prepared from a compound of the general formula:

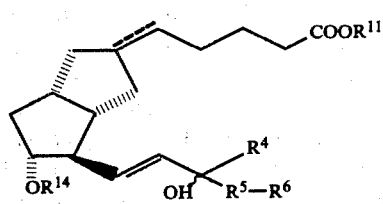

(wherein $R^{14}$ represents a hydroxy-protecting group which is eliminated under alkaline conditions and the other symbols are as hereinbefore defined) by means heretofore mentioned for the conversion of compounds of general formula III to those of general formula V.

Compounds of general formulae IVA and IVB, i.e. compounds of the general formula:

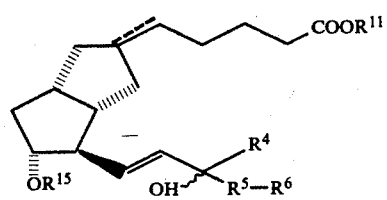

[wherein $R^{15}$ represents a hydroxy-protecting group which is eliminated under acidic or alkaline conditions, preferably the tetrahydropyran-2-yl group (which is eliminated under acidic conditions), and the other symbols are as hereinbefore defined] may be prepared from a compound of the general formula:

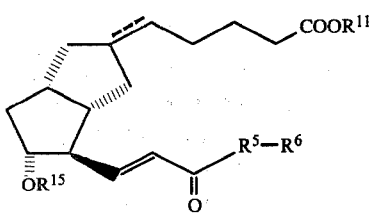

VII (wherein the various symbols are as hereinbefore defined), (1) when $R^4$ in the formula IV is a hydrogen atom, by reaction with a known reducing agent for the conversion of an oxo group to a hydroxy group without affecting carbon to carbon double bonds, e.g. sodium borohydride, potassium borohydride, lithium borohydride, zinc borohydride, tri-tert-butoxylithiumaluminiumhydride, trimethoxylithiumaluminiumhydride or sodium cyanoborohydride, or diisobornyloxyaluminiumisopropoxide (described in Japanese Patent Application No. 52-142283), or by the method described in J. Amer. Chem. Soc., 94, 8616 (1972), and (2) when $R^4$ is a methyl or ethyl group, by reaction with an organometallic compound of the general formula:

$$R^{16}\text{—Met} \qquad \text{VIII}$$

(wherein $R^{16}$ represents a methyl or ethyl group and Met represents a lithium atom or a magnesium halide group) in an inert organic solvent, e.g. diethyl ether, tetrahydrofuran or hexane, at a low temperature, preferably below 0° C., more particularly in the case of a organolithium compound, at below −20° C., or with an aluminium compound of the general formula:

$$(R^{16})_3\text{Al} \qquad \text{IX}$$

(wherein $R^{16}$ is as hereinbefore defined) by the method described in J. Amer. Chem. Soc., 96, 5865 (1974).

Compounds of general formula III may also be prepared from compounds of the general formula:

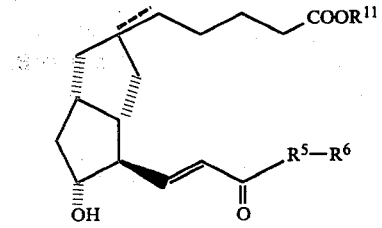

X (wherein the various symbols are as hereinbefore defined) by means heretofore mentioned for the conversion of compounds of general formula VII to those of general formula IV.

Compounds of general formula X may be prepared from compounds of general formula VII, wherein $R^{15}$ represents a hydroxy-protecting group which is eliminated under acidic conditions and the other symbols are as hereinbefore defined, i.e. compounds of the general formula:

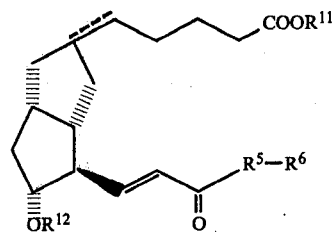

XI (wherein the various symbols are as hereinbefore defined) by hydrolysis under acidic conditions by means heretofore mentioned for the conversion of compounds of general formula IVA to those of general formula III.

The product of general formula III or IV, thus obtained, is a mixture of isomers in which the hydroxy group at position 15 is in the α- or β-configuration. If desired, the isomer having the hydroxy group in a α-configuration may be separated from the isomer having the hydroxy group in β-configuration by a known method of separation, e.g. by thin layer, column or high-speed liquid chromatography on silica gel.

The method hereinbefore described for the preparation of prostaglandin $I_2$ analogues of general formulae III, V and VI may be represented by the series of reactions depicted schematically below in Scheme A, wherein the various symbols are as hereinbefore defined.

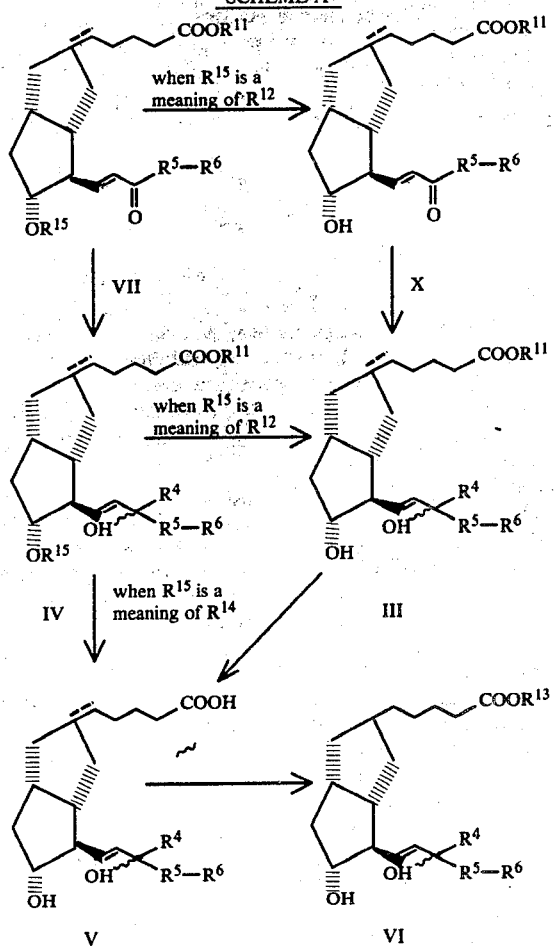

SCHEME A

Starting materials of general formula VII may be prepared by the Wittig reaction of a compound of the general formula:

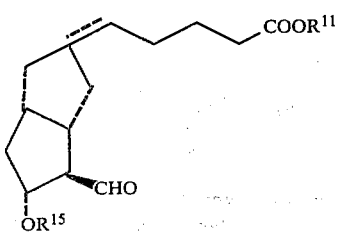

(wherein the various symbols are as hereinbefore defined) with the sodium derivative of a dialkylphosphonate of the general formula:

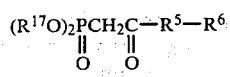

(wherein $R^{17}$ represents a lower alkyl group containing from 1 to 4 carbon atoms, preferably methyl or ethyl, and $R^5$ and $R^6$ are as hereinbefore defined), obtained by the reaction of a dialkylphosphonate of formula XIII with sodium hydride, or with a phosphorane compound of the general formula:

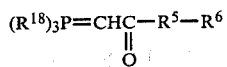

(wherein $R^{18}$ represents a phenyl group unsubstituted or substituted by a lower alkyl group containing from 1 to 4 carbon atoms, preferably an unsubstituted phenyl group, or a lower alkyl group containing from 1 to 6 carbon atoms, preferably butyl, or the cyclohexyl group, and $R^5$ and $R^6$ are as hereinbefore defined) to form the trans-enone compound of general formula VII stereoselectively. The Wittig reaction is effected in an inert organic solvent, e.g. an ether such as diethyl ether, tetrahydrofuran, dioxan or 1,2-dimethoxyethane, a hydrocarbon such as benzene, toluene, xylene or hexane, a dialkyl sulphoxide such as dimethyl sulphoxide, a dialkylformamide such as N,N-dimethylformamide, a halogenated hydrocarbon such as methylene chloride or chloroform, or a lower alkanol such as methanol or ethanol at a temperature from 0° to the reflux temperature of the reaction mixture.

The dialkyl phosphonates of general formula XIII and the phosphonate compounds of general formula XIV may be prepared by methods known per se.

Compounds of general formula XII may be prepared from a compound of the general formula:

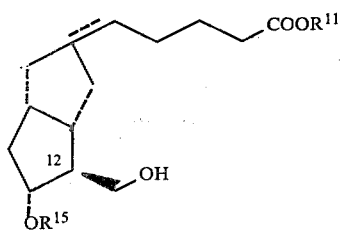

(wherein the various symbols are as hereinbefore defined) by oxidation to convert the hydroxymethyl group attached to the 12-position to a formyl group. The oxidation is carried out by methods known per se for the conversion of a hydroxymethyl group to a formyl group, for example by methods described in (a) Tetsuji Kameya, 'Synthetic Organic Chemistry III, Organic Synthesis 1' pp 176–206 (1976), Nankodo (Japan), or in (b) 'Compendium of Organic Synthetic Methods', Volume 1 (1971), 2 (1974) and 3 (1977), Section 48, John Wiley & Sons, Inc. (USA). Preferably the oxidation is carried out under mild and neutral conditions, for example with dimethyl sulphide-N-chlorosuccinimide complex, thioanisole-N-chlorosuccinimide complex, dimethyl sulphide-chlorine complex or thioanisolechlorine complex [cf. J. Amer. Chem. Soc., 94, 7586 (1972)], dicyclohexylcarbodiimide-dimethyl sulphoxide complex [cf. J. Amer. Chem. Soc., 87, 5661 (1965)], pyridinium chlorochromate ($C_5H_5NHCrO_3Cl$) [cf. Tetrahedron Letters, 2647 (1975)], chromium trioxide-pyridine complex (e.g. Collins' reagent) or Jones' reagent.

The oxidation using dimethyl sulphide-N-chlorosuccinimide complex, thioanisole-N-chlorosuccinimide complex, dimethyl sulphide-chlorine complex or thioanisolechlorine complex may be effected by reaction in a halogenated hydrocarbon such as chloroform, methylene chloride or carbon tetrachloride, or toluene at $-30°$ to $0°$ C., and then treatment with triethylamine. The oxidation using the dicyclohexylcarbodiimide-dimethyl sulphoxide complex is normally effected by reaction in excess dimethyl sulphoxide in the presence of an acid, e.g. phosphoric acid, phosphoric acid, cyanoacetic acid, pyridine-phosphoric acid salt or trifluoroacetic acid, as catalyst. The oxidation using the pyridinium chlorochromate may be effected by reaction in a halogenated hydrocarbon such as chloroform, methylene chloride or carbon tetrachloride in the presence of sodium acetate, normally at ambient temperature. The oxidation using the chromium trioxidepyridine complex may be effected by reaction in a halogenated hydrocarbon such as chloroform, methylene chloride or carbon tetrachloride at a temperature from 0° C. to ambient, preferably 0° C. The oxidation using Jones' reagent is normally effected with acetone and dilute sulphuric acid at a temperature from 0° C. to ambient.

Compounds of general formula XV, wherein ----- represents a double bond and the other symbols are as hereinbefore defined, i.e. compounds of the general formula:

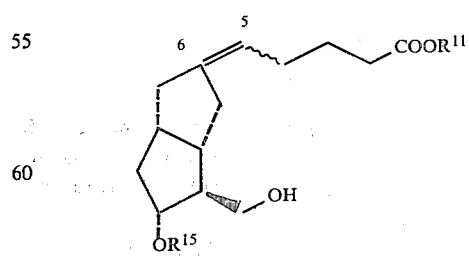

[wherein the double bond between $C_5-C_6$ is E or Z or a mixture thereof (i.e. EZ) and the other symbols are as hereinbefore defined] may be prepared by the Wittig reaction of a compound of the general formula:

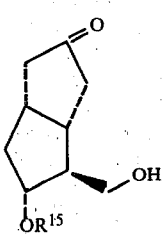

XVII (wherein $R^{15}$ is as hereinbefore defined) with (4-carboxybutylidene)triphenylphosphorane of the formula:

$$(C_6H_5)_3P=CH—(CH_2)_3—COOH \qquad XVIII$$

and then esterification by methods known per se. The method for the Wittig reaction is described in Organic Reactions, 14, Chapter 3 (1965), John Wiley & Sons, Inc. Preferably the Wittig reaction is carried out in an inert organic solvent such as dimethyl sulphoxide, normally at a temperature from 10° to 60° C.

The phosphorane of general formula XVIII may be obtained by reaction of dimsyl sodium with (4-carboxybutyl)triphenylphosphonium bromide.

The esterification may be carried out by means heretofore mentioned for the conversion of compounds of general formula V to those of general formula VI.

The product of general formula XVI, thus obtained, is a mixture of isomers in which the double bond between $C_5-C_6$ is E or Z. If desired, the isomer having the double bond in Z configuration may be separated from the isomer having the double bond in E configuration by a known method of separation, e.g. by thin layer or column chromatography on silica gel or magnesium trisilicate.

Compounds of general formula XV, wherein 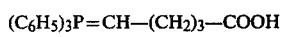 represents a single bond and the other symbols are as hereinbefore defined, i.e. compounds of the general formula:

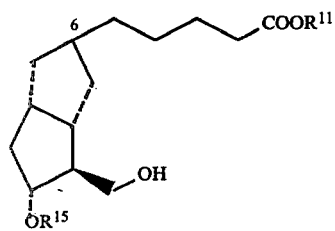

XIX

[wherein the absolute configuration of $C_6$ is R, S or a mixture thereof (i.e. RS) and $R^{11}$ and $R^{15}$ are as hereinbefore defined] may be prepared from compounds of general formula XVI or a compound of the general formula:

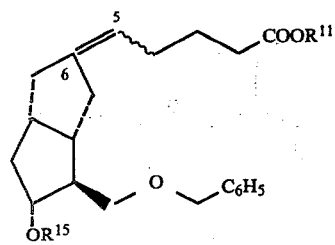

XX (wherein the double bond between $C_5-C_6$ is E or Z, or a mixture thereof, and $R^{11}$ and $R^{15}$ are as hereinbefore defined) by reduction. It is to be understood that the group $C_6H_5$ in formula XX and in subsequent formulae in this specification is the phenyl group. Suitably, the reduction may be effected by hydrogenation in the presence of a hydrogenation catalyst, e.g. palladium on charcoal, palladium black or platinum dioxide, in an inert organic solvent, for example a lower alkanol such as methanol or ethanol, or acetic acid or a mixture of them at laboratory temperature at normal or elevated pressure, for example at a hydrogen pressure from atmospheric to 15 kg/cm².

Compounds of general formula XX may be prepared from a compound of the general formula:

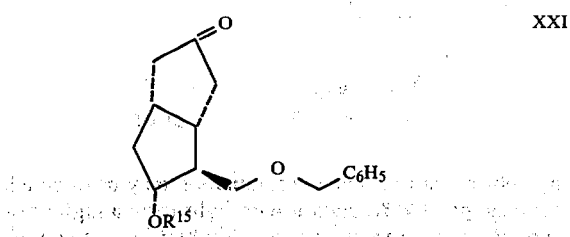

XXI (wherein $R^{15}$ is as hereinbefore defined) by means heretofore mentioned for the conversion of compounds of general formula XVII to those of general formula XVI.

Compounds of general formula XVII may be prepared by reductive elimination of the benzyl group of compounds of general formula XXI by means heretofore mentioned for the conversion of compounds of general formula XX to those of general formula XIX.

Compounds of general formula XXI may be prepared by converting the hydroxy group of a compound of the formula:

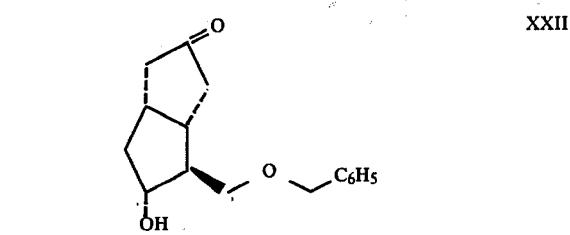

XXII to a protected hydroxy group by methods known per se. For example, methods for the conversion are described in 'Protective Groups in Organic Chemistry', Chapter 3 (1973), Plenum Press, particularly ibid, pp 104–106 for the conversion of a hydroxy group to a tetrahydropyran-2-yloxy group which is preferable as $OR^{15}$. For example, when $R^{15}$ is a heterocyclic group or an ether group, the conversion may be effected by using 2,3-dihydropyran, 2,3-dihydrofuran, 2,3-dihydrothiopyran, ethyl vinyl ether, 2-methoxypropene, 1-methoxycyclohexane or α-methoxystyrene in an inert organic solvent such as methylene chloride in the presence of a condensing agent, e.g. p-toluenesulphonic acid, sulphuric acid, trifluoroborane-etherate or phosphorus oxychloride at a temperature from ambient to 30° C., preferably at ambient temperature, or when $R^{15}$ is a tri-substituted silyl group, the reaction may be effected by using a tri-substituted silylating reagent, e.g. trimethylchlorosilane or trimethylsilyldiethylamine in the absence or presence of a tertiary amine such as pyridine or triethylamine in an inert organic solvent such as methylene chloride or acetone at a temperature from ambient to 30° C. When $R^{15}$ is an acetyl or mono-, di- or tri-haloacetyl group, the reaction may be effected by using acetyl or a haloacetyl chloride, or acetic or a haloacetic anhydride in the presence of a tertiary amine such as triethylamine or pyridine in an inert organic solvent such as methylene chloride at a temperature below ambient, preferably at 0° C.

The compounds of formula XXII may be prepared from a compound of the formula:

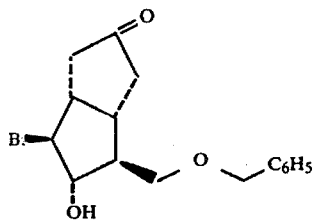
XXIII by debromination. The debromination may be effected, for example, by irradiation with light from a high pressure mercury lamp using tributyltin hydride in the presence of $\alpha,\alpha'$-azobisisobutyronitrile in benzene at room temperature.

The compound of formula XXIII may be converted to a compound of the general formula:

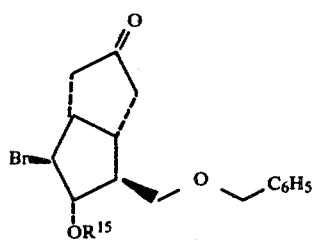
XXIV (wherein $R^{15}$ is as hereinbefore defined) by means heretofore mentioned for the conversion of compounds of general formula XXII to those of general formula XXI.

Compounds of general formula XXIV may be converted to compounds of general formula XXI by means heretofore mentioned for the conversion of compounds of general formula XXIII to those of general formula XXII.

The compounds of formula XXIII may be prepared from a compound of the formula:

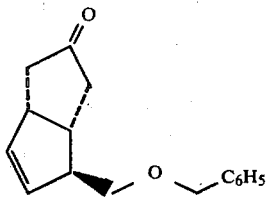
XXV by methods known per se for the conversion of an olefine to a bromohydrin, for example, by reaction with N-bromosuccinimide in aqueous dimethyl sulphoxide at room temperature.

The method hereinbefore described for the preparation of compounds of general formula VII may be represented by the series of reactions depicted schematically below in Scheme B, wherein the various symbols are as hereinbefore defined.

SCHEME B

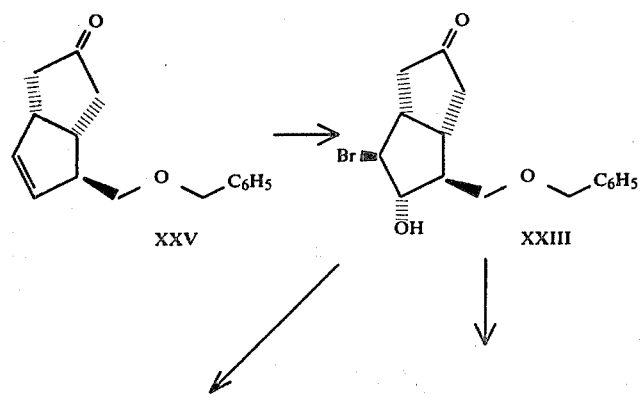

-continued
SCHEME B
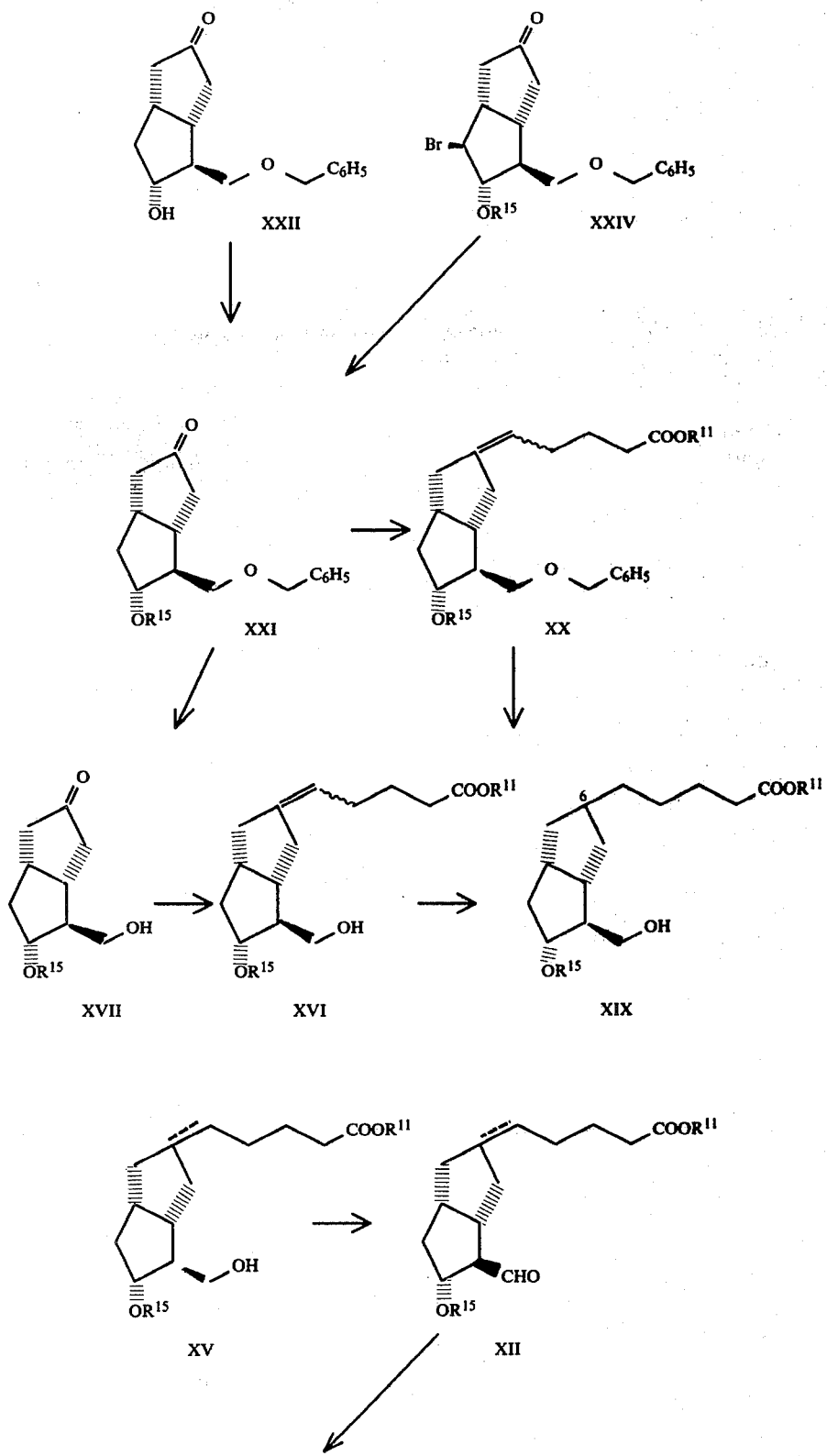

SCHEME B
-continued

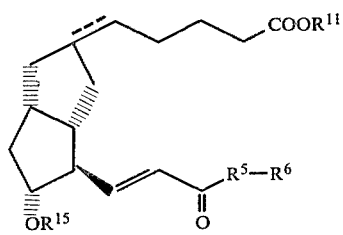

VII

Compounds of general formula XXV, used as a starting material may themselves be prepared from a known compound of the formula XXVI (depicted hereafter) described in J. Amer. Chem. Soc., 93, 1492 (1971) by the series of reactions depicted schematically below in Scheme C, wherein $R^{19}$ and $R^{20}$, which may be the same or different, each represent a methyl or ethyl group: the group $COOR^{19}$ or $COOR^{20}$ in formula XXIX may be attached to the 2- or 4-position.

by the method described in Angew. Chem. Internat. Edit., 14, 103 (1975).

The conversion of compounds of general formula XXVIII to those of general formula XXIX may be carried out by the Dieckmann reaction, for example, by reaction in the presence of potassium tert-butoxide in benzene at a temperature from ambient to 80° C.

The conversion of compounds of general formula XXIX to those of general formula XXV may be carried

SCHEME C

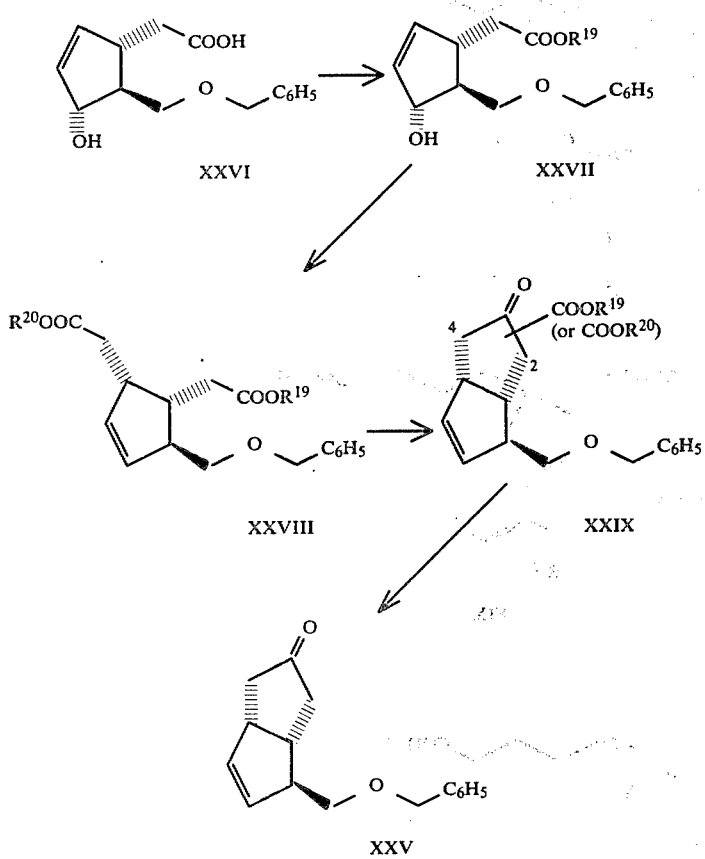

The conversion of the compound of formula XXVI to compounds of general formula XXVII may be carried out by esterification by known methods, e.g. as heretofore mentioned for the conversion of compounds of general formula V to those of general formula VI.

The conversion of compounds of general formula XXVII to those of general formula XXVIII may be carried out by the Claisen rearrangement, for example, out by decarboxylation, by heating in an inert organic solvent having a high boiling-point, such as aqueous hexamethylphosphoramide (HMPA) or aqueous dimethyl sulphoxide.

Compounds of general formula XXI may also be prepared from compounds of general formula XXVII by the series of reactions depicted schematically below in Scheme D, wherein $R^{15}$ and $R^{19}$ are as hereinbefore defined.

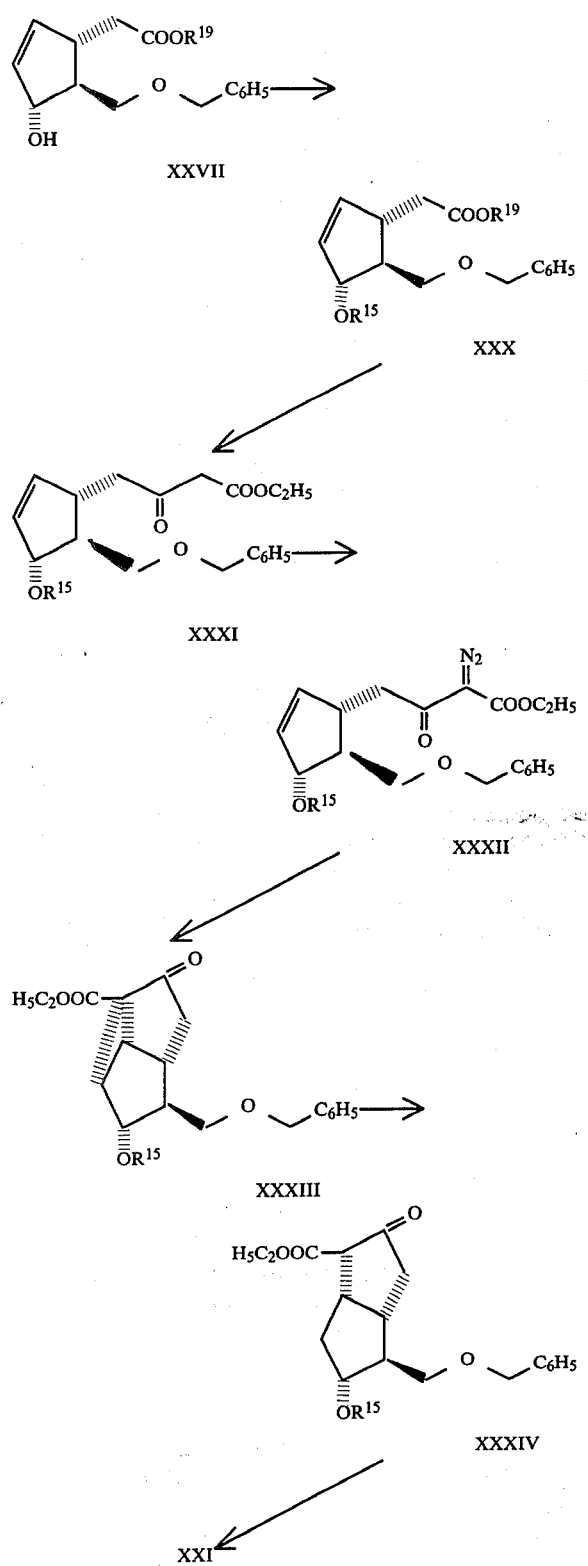

The conversion of compounds of general formula XXVII to those of general formula XXX may be carried out by means heretofore mentioned for the conversion of compounds of general formula XXII to those of general formula XXI.

Compounds of general formula XXXI may be prepared by reacting compounds of general formula XXX with lithium ethyl acetate ($LiCH_2COOC_2H_5$, obtained from lithium diisopropylamide and ethyl acetate) in tetrahydrofuran at $-78°$ to $0°$ C.

Compounds of general formula XXXII may be prepared by reacting compounds of general formula XXXI with p-toluenesulphonyl azide in the presence of triethylamine in acetonitrile at a temperature from $0°$ C. to ambient.

Compounds of general formula XXXIII may be prepared from compounds of general formula XXXII by heating to reflux in the presence of copper (II) sulphate in benzene.

Compounds of general formula XXXIV may be prepared from compounds of general formula XXXIII by irradiation with light from a high pressure mercury lamp using tributyltin hydride in the presence of $\alpha,\alpha'$-azobisisobutyronitrile in benzene at room temperature.

The conversion of compounds of general formula XXXIV to those of general formula XXI may be carried out by means heretofore mentioned for the conversion of compounds of general formula XXIX to those of general formula XXV.

A compound of general formula XXI wherein $R^{15}$ is a tetrahydropyran-2-yl group, i.e. a compound of the formula XL (depicted hereafter) may also be prepared from a known compound of the formula XXXV (depicted hereafter) described in J. Amer. Chem. Soc., 93, 1490 (1971) by the series of reactions depicted schematically below in Scheme E, wherein THP represents a tetrahydropyran-2-yl group: the group $COOCH_3$ in formula XXXVII may be in the E or Z configuration; the group $COOCH_3$ in formula XXXIX may be attached to the 2- or 4-position.

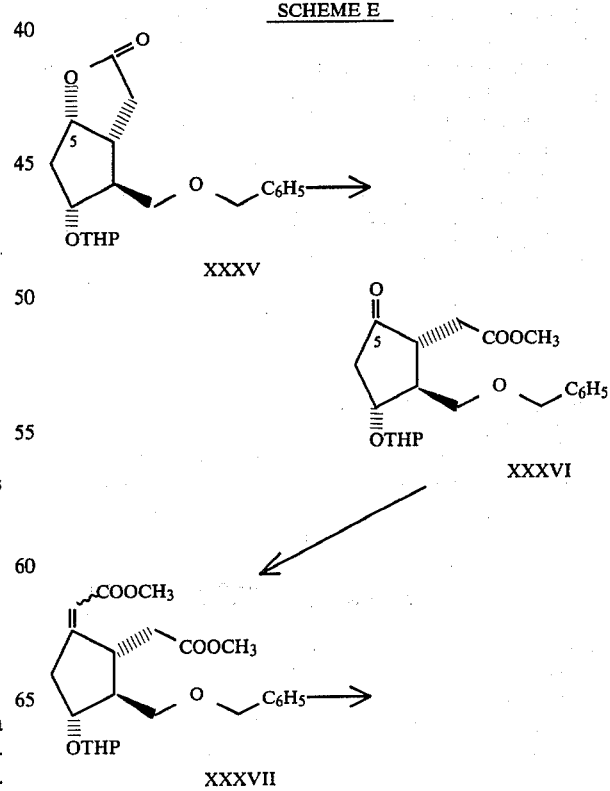

-continued
SCHEME E

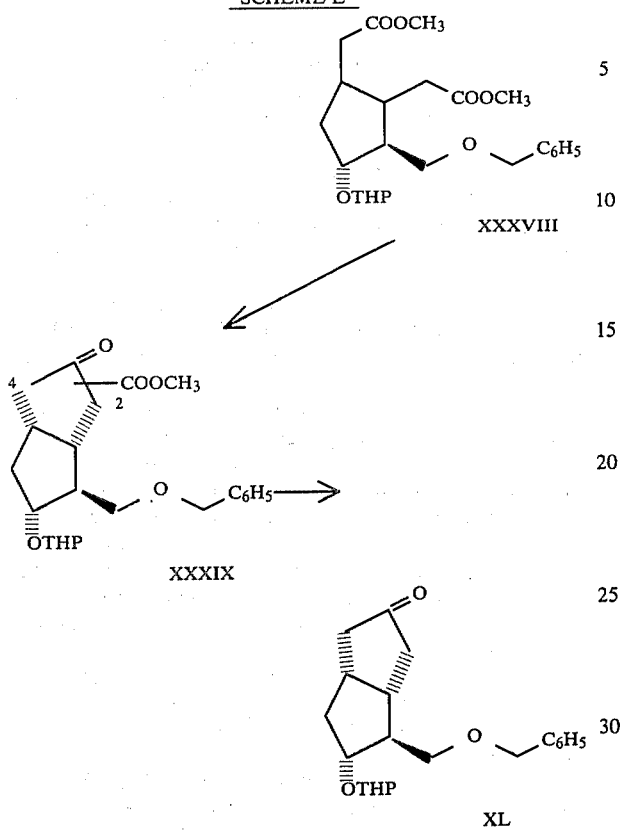

XXXVIII

XXXIX

XL

The compound of formula XXXVI may be prepared from the compound of formula XXXV by hydrolysis under alkaline conditions by means heretofore mentioned for the conversion of compounds of general formula III to those of general formula V, converting the resulting product to the corresponding methyl ester by means heretofore mentioned for the conversion of compounds of general formula V to those of general formula VI and then oxidizing a hydroxy group in the 5-position to an oxo group by methods known per se, for example, by the method described in J. Amer. Chem. Soc., 97, 5927 (1975).

The compound of formula XXXVII may be prepared by reacting the compound of formula XXXVI with methyllithiotrimethylsilyl acetate

[i.e. $(CH_3)_3Si\overset{\ominus}{C}HCOOCH_3$]

by the method described in J. Amer. Chem. Soc., 96, 1620 (1974).

The conversion of the compound of formula XXXVII to that of formula XXXVIII may be carried out by means heretofore mentioned for the conversion of compounds of general formula XX to those of general formula XIX.

The conversion of the compound of formula XXXVIII to that of formula XXXIX may be carried out by means heretofore mentioned for the conversion of compounds of general formula XXVIII to those of general formula XXIX.

The conversion of the compound of formula XXXIX to that of formula XL may be carried out by means heretofore mentioned for the conversion of compounds of general formula XXIX to a compound of formula XXV.

The compound of formula XL may be converted to the compound of formula XXII by hydrolysis under acidic conditions by means heretofore mentioned for the conversion of compounds of general formula IVA to those of general formula III. The compound of formula XXII, thus obtained, may be converted to compounds of general formula XXI, wherein $R^{15}$ represents a group other than a tetrahydropyran-2-yl group.

According to a further feature of the present invention, the prostaglandin $I_2$ analogues of general formula II, wherein ≈≈≈ represents a double bond, $R^2$ and $R^3$ represent hydrogen atoms and the other symbols are as hereinbefore defined, i.e. compounds of the general formula:

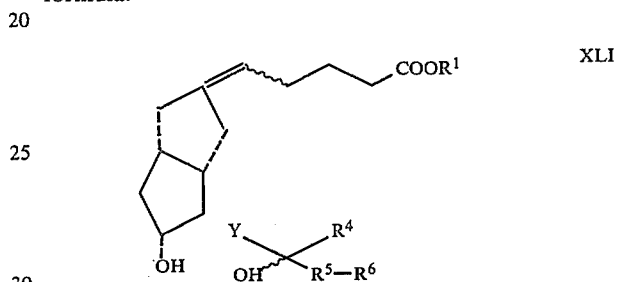

XLI

[wherein the double bond between $C_5$–$C_6$ is E or Z or a mixture thereof (i.e. EZ) and the other symbols are as hereinbefore defined] may be prepared from a compound of general formula II, wherein ≈≈≈ represents a double bond, $R^2$ represents a hydrogen atom or a hydroxy-protecting group which is eliminated under acidic conditions, $R^3$ represents a hydroxy-protecting group which is eliminated under acidic conditions and the other symbols are as hereinbefore defined, i.e. a compound of the general formula:

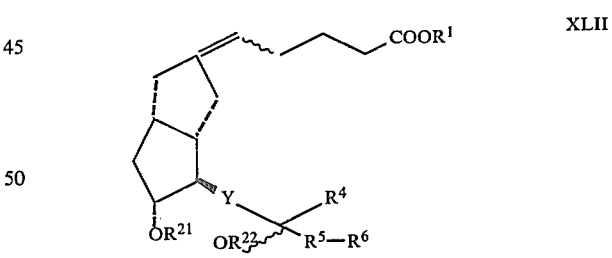

XLII (wherein $R^{21}$ represents a hydrogen atom or a hydroxy-protecting group which is eliminated under acidic conditions, $R^{22}$ represents a hydroxy-protecting group which is eliminated under acidic conditions and the other symbols are as hereinbefore defined) by means heretofore mentioned for the conversion of compounds of general formula IVA to those of general formula III.

Esters of general formula XLII, wherein $R^1$ is other than a hydrogen atom and the other symbols are as hereinbefore defined, may be prepared from compounds of general formula XLII, wherein $R^1$ is a hydrogen atom and the other symbols are as hereinbefore defined, i.e. compounds of the general formula:

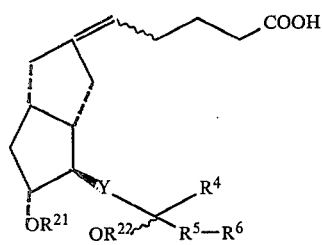

XLIII

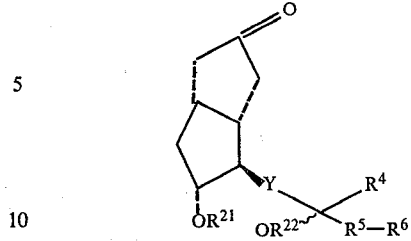

XLIV (wherein the various symbols are as hereinbefore defined) by esterification by means heretofore mentioned for the conversion of compounds of formula V to those of general formula VI.

According to a further feature of the present invention compounds of general formulae III, IV, IVA, IVB, V, VI, XLI, XLII and XLIII having a double bond in one or both of the $C_5$–$C_6$ and $C_{13}$–$C_{14}$ positions may be converted to corresponding compounds of general formula III, IV, IVA, IVB, V, VI, XLI, XLII and XLIII, respectively, having a single bond in both the $C_5$–$C_6$ and $C_{13}$–$C_{14}$ positions by means heretofore described for the conversion of compounds of general formula XVI or XX to those of general formula XIX.

Compounds of general formula XLIII may be prepared by the Wittig reaction of a compound of the general formula:

(wherein the various symbols are as hereinbefore defined) with (4-carboxybutylidene)triphenylphosphorane of formula XVIII by means heretofore mentioned for the conversion of compounds of general formula XVII to those of general formula XVI.

The product of general formula XLIII, thus obtained, is a mixture of isomers in which the double bond between $C_5$–$C_6$ is E or Z. If desired the isomer having the double bond in Z configuration may be separated from the isomer having the double bond in E configuration by a known method of separation, e.g. by thin layer or column chromatography on silica gel or magnesium trisilicate.

Compounds of general formula XLIV, used as a starting material in the hereinbefore described procedure, may themselves be prepared by the series of reactions depicted schematically below in Scheme F, wherein $CO\phi$ represents the benzoyl group, Ac represents the acetyl group and the other symbols are as hereinbefore defined. The group $COOCH_3$ in formula XLIX may be attached to the 2- or 4-position.

SCHEME F

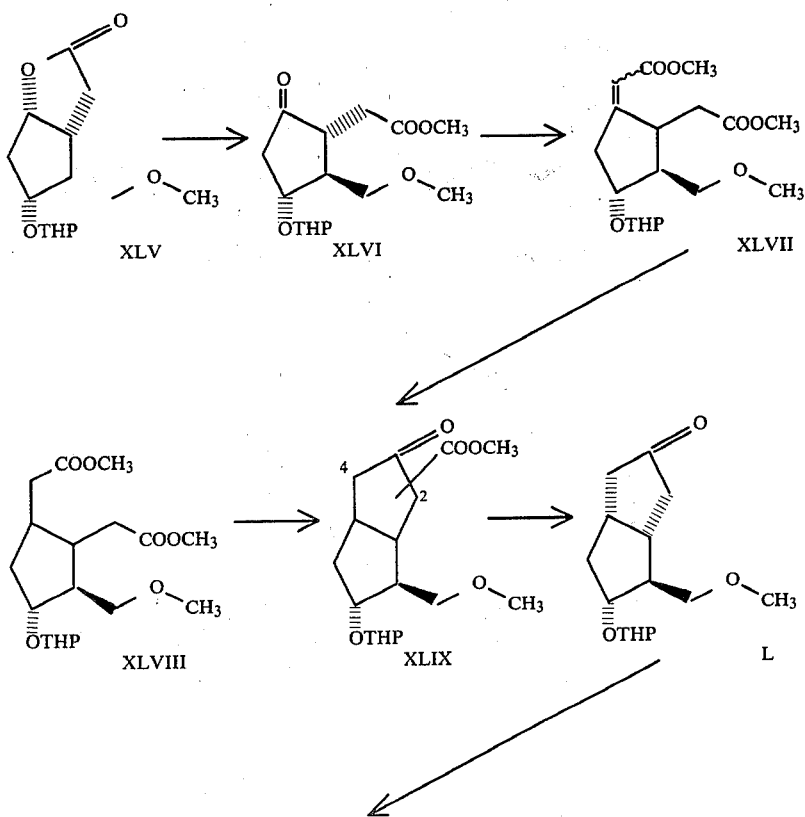

SCHEME F
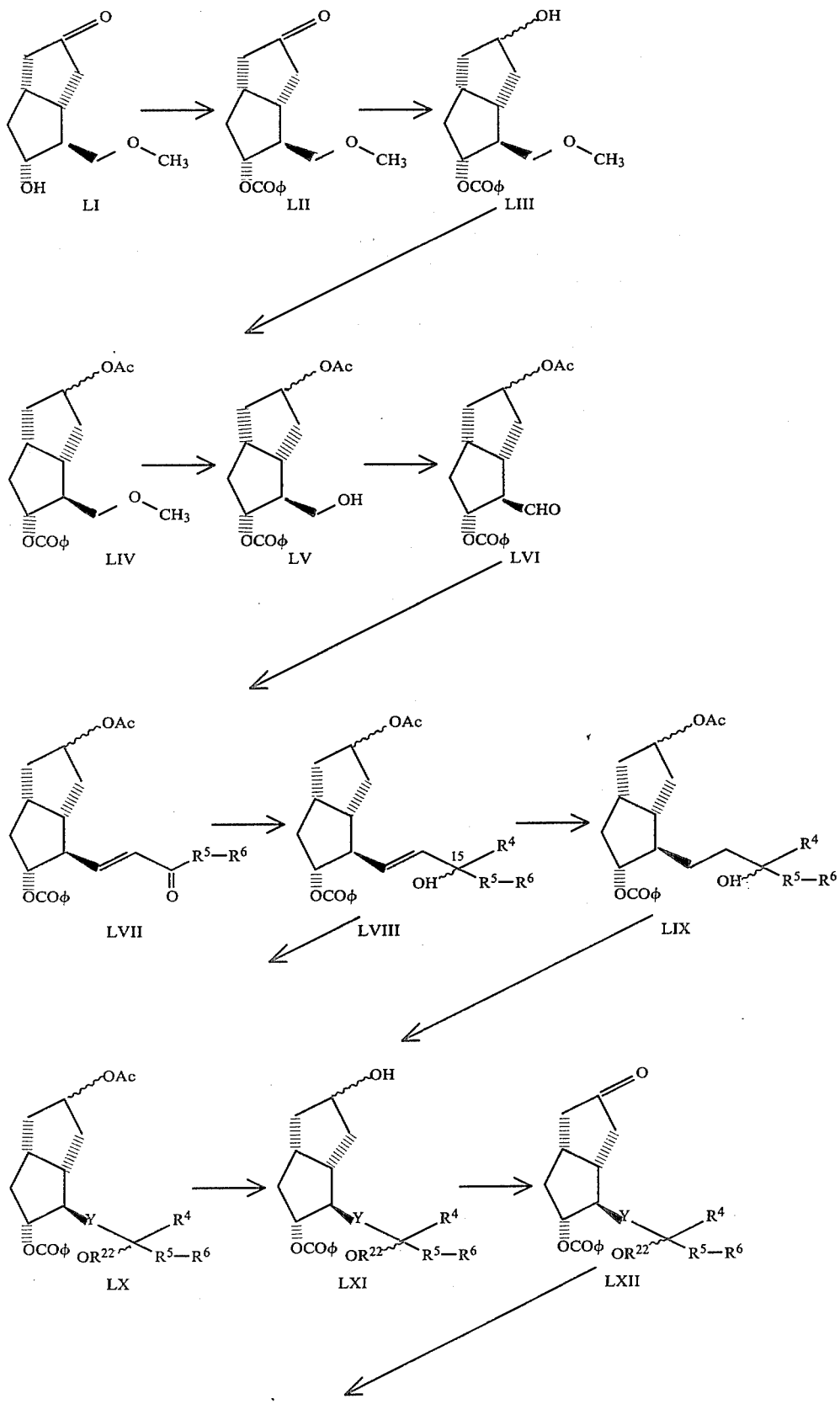

-continued
SCHEME F

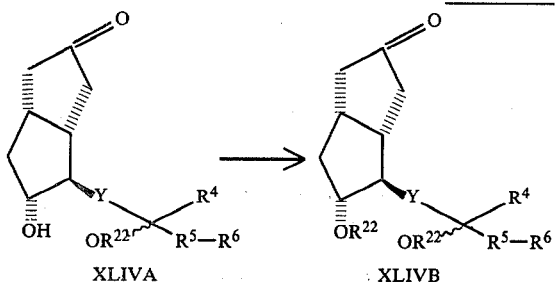

The series of reactions XLV→XLVI→XLVII→XLVXII→XLIX→L in Scheme F may be effected as hereinbefore described for the series of reactions XXXV→XXXVI→XXXVII→XXXVIII→XXXIX→XL in Scheme E.

The conversion of the compound of formula L to that of formula LI may be carried out by means heretofore mentioned for the conversion of the compounds of formula IVA to those of formula III.

The compound of formula LII may be prepared by reacting the compound of formula LI with benzoyl chloride in the presence of a tertiary amine such as pyridine or triethylamine in an inert organic solvent such as methylene chloride at room temperature.

The conversion of the compound of formula LII to that of the formula LIII may be carried out by means heretofore mentioned for the conversion of compounds of general formula VII to those of general formula IV, wherein $R^4$ is a hydrogen atom.

The conversion of the compound of formula LIII to that of formula LIV may be carried out by using acetyl chloride or acetic anhydride in the presence of a tertiary amine such as pyridine or triethylamine in an inert organic solvent such as methylene chloride at 0° C.

The conversion of the compound of formula LIV to that of formula LV may be carried out by methods described in J. Amer. Chem. Soc., 91, 5676 (1969).

The conversions of the compound of formula LV to that of formula LVI, of the compound of formula LVI to the compound of general formula LVII and of the compounds of general formula LVII to those of general formula LVIII may be carried out by means heretofore mentioned for the conversion of the compounds of formula XV to those of formula XII, of the compounds of formula XII to those of formula VII, and of the compounds of formula VII to those of formula IV, respectively.

The product of general formula LVIII, thus obtained, is a mixture of isomers in which the hydroxy group at position 15 is in α- or β-configuration. If desired, the isomer having the hydroxy group in α-configuration may be separated from the isomer having the hydroxy group in β-configuration by a known method of separation, e.g. by thin layer, column or high-speed liquid chromatography on silica gel.

The conversion of compounds of general formula LVIII to those of general formula LIX may be carried out by means heretofore mentioned for the conversion of the compounds of formula XX to those of formula XIX.

Compounds of general formula LX may be prepared by converting by methods known per se the hydroxy group of compounds of general formula LVIII or of general formula LIX to a hydroxy-protecting group which is eliminated under acidic conditions.

Compounds of general formula LXI may be prepared by deacetylation of compounds of general formula LX using sodium or potassium carbonate in a lower alkanol such as methanol or ethanol at a temperature below ambient. Preferably the deacetylation is carried out at 0° C. in order to avoid the risk of removal of the benzoyl group.

The conversion of compounds of general formula LXI to those of general formula LXII may be carried out by means heretofore mentioned for the conversion of compounds of general formula XV to those of general formula XII.

Compounds of general formula XLIVA may be prepared from compounds of general formula LXII by elimination of the benzoyl group in compounds of formula LXXI using an alkali metal, e.g. sodium or potassium, hydroxide or carbonate in a lower alkanol such as methanol or ethanol at a temperature above ambient.

If desired, compounds of general formula XLIVA may be converted to compounds of general formula XLIVB by means heretofore mentioned for the conversion of compounds of formula LVIII or LIX to those of general formula LX.

Compounds of general formula XLV, used as a starting material in the hereinbefore described procedure, may themselves be prepared by deacetylation of the compound of the formula:

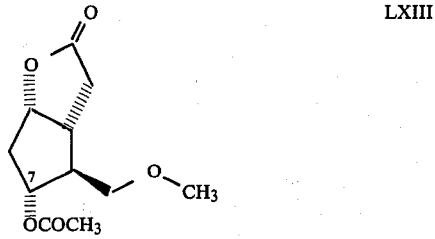

LXIII

[described in J. Amer. Chem. Soc., 91, 5675 (1969) and ibid, 92, 397 (1970)] by means heretofore mentioned for the conversion of compounds of general formula LX to those of general formula LXI, followed by conversion of a hydroxy group in the 7-position of the resulting compound to a tetrahydropyran-2-yloxy group by means heretofore mentioned for the conversion of compounds of general formula LVIII or LIX to those of general formula LX.

Esters of the prostaglandin $I_2$ analogues of general formula II, wherein $R^1$ is other than a hydrogen atom, $R^2$ and $R^3$ represent hydrogen atoms and the other symbols are as hereinbefore defined, may be prepared by esterification of the corresponding acid of general formula II, wherein $R^1$, $R^2$ and $R^3$ represent hydrogen atoms and the other symbols are as hereinbefore defined by methods known per se, for example by means heretofore mentioned for the conversion of compounds of general formula V to those of general formula VI.

Acids of the prostaglandin $I_2$ analogues of general formula II, wherein $R^1$, $R^2$ and $R^3$ represent hydrogen atoms and the other symbols are as hereinbefore defined, may be prepared by saponification of the corresponding ester of general formula II, wherein $R^1$ is other than a hydrogen atom, $R^2$ and $R^3$ are hydrogen atoms and the other symbols are as hereinbefore defined, by methods known per se, for example by means heretofore mentioned for the conversion of compounds of general formula III to those of general formula V.

Cyclodextrin clathrates of the prostaglandin $I_2$ analogues of general formula II, wherein $R^2$ and $R^3$ represent hydrogen atoms and the other symbols are as hereinbefore defined, may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. $\alpha$-, $\beta$- or $\gamma$-Cyclodextrins or mixtures thereof may be used in the preparation of the cyclodextrin clathrates. Conversion into cyclodextrin clathrates serves to increase the stability of the prostaglandin $I_2$ analogues of general formula II.

Compounds of general formula II, wherein $R^1$, $R^2$ and $R^3$ represent a hydrogen atom, may, if desired, be converted by methods known per se into salts. Preferably the salts are non-toxic salts. By the term 'non-toxic salts', as used in this specification, is meant salts the cations of which are relatively innocuous to the animal organism when used in therapeutic doses so that the beneficial pharmacological properties of the compounds of general formula II are not vitiated by side-effects ascribable to those cations. Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acid are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms. Suitable non-toxic amine salts are, e.g. tetralkylammonium, such as tetramethylammonium, salts, and other organic amine salts such as methylamine salts, dimethylamine salts, cyclopentylamine salts, benzylamine salts, phenethylamine salts, piperidine salts, monoethanolamine salts, diethanolamine salts, lysine salts and arginine salts.

Salts may be prepared from the acids of general formula II, wherein $R^1$, $R^2$ and $R^3$ represent hydrogen atoms, by methods known per se, for example by reaction of stoichiometric quantities of an acid of general formula II and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

Sodium salts may also be prepared by treatment of an ester of general formula II, wherein $R^1$ represents an alkyl group containing from 1 to 12 carbon atoms, $R^2$ and $R^3$ represent hydrogen atoms and the other symbols are as hereinbefore defined, with one equivalent amount of sodium hydroxide in the presence of an aqueous alkanol containing from 1 to 4 carbon atoms, preferably aqueous methanol, at a temperature of from 0° to 60° C. preferably at ambient temperature.

Prostaglandin analogues of general formula II wherein $R^1$ represents a group

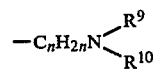

wherein n, $R^9$ and $R^{10}$ are as hereinbefore defined and $R^2$ and $R^3$ represent hydrogen atoms may be converted by methods known per se into acid addition salts, which are preferably non-toxic. By the term 'non-toxic acid addition salts' as used in this specification is meant salts the anions of which are relatively innocuous to the animal organism when used in therapeutic doses so that the beneficial pharmacological properties of the compounds of general formula II are not vitiated by side effects ascribable to those anions.

Acid addition salts may be prepared from the compounds of general formula II by methods known per se for example by reaction of stoichiometric quantities of a compound of general formula II and the appropriate acid, e.g. an inorganic acid such as hydrochloric acid, hydrobromic acid, hydroiodic acid, sulphuric acid, phosphoric acid or nitric acid, or an organic acid such as acetic acid, propionic acid, lactic acid, tartaric acid, citric acid, methanesulphonic acid, ethanesulphonic acid, benzenesulphonic acid, toluenesulphonic acid, isethionic acid or succinic acid, in a suitable solvent. The acid addition salts may be purified by recrystallisation from one or two or more suitable solvents.

The prostaglandin analogues of general formula II wherein $R^2$ and $R^3$ represent hydrogen atoms, and their cyclodextrin clathrates, and when $R^1$, $R^2$ and $R^3$ represent atoms, non-toxic salts thereof and, when $R^1$ represents a

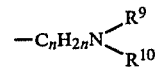

group in which n, $R^9$ and $R^{10}$ are as hereinbefore defined and $R^2$ and $R^3$ represent hydrogen atoms, non-toxic acid addition salts thereof, possess the valuable pharmacological properties typical of the prostaglandins in a selective fashion, in particular hypotensive activity, inhibitory activity on blood platelet aggregation, stimulatory activity on uterine contraction, and are useful in the treatment of hypertension, in the treatment of disorders of the peripheral circulation, and in the prevention and treatment of cerebral thrombosis, myocardial infarction and arteriosclerosis.

For example, in standard laboratory tests, (i) by intravenous administration to the allobarbital anaesthetized dog, (5EZ,13E)-(9α,11α,15α)-6,9-methano-11,15-dihydroxyprosta-5,13-dienoic acid methyl ester produces falls in blood pressure of 16, 24 and 30 mmHg lasting 3, 5 and 7 minutes at the doses of 5, 10 and 20 μg/kg animal body weight, respectively, (5EZ,13E)-(9α,11α,15α)-6,9-methano-11,15-dihydroxyprosta-5,13-dienoic acid produces falls in blood pressure of 26 and 34 mmHg lasting 4 and 7 minutes at the doses of 4 and 8 μg/kg animal body weight, respectively, (5EZ,13E)-(9α,11α,15α,16RS)-6,9-methano-11,15-dihydroxy-16-chloroprosta-5,13-dienoic acid methyl ester produces falls in blood pressure of 24 and 44 mmHg lasting 9 and 13 minutes at the doses of 5 and 10 μg/kg animal body weight, respectively, (5EZ,13E)-(9α,11α,15α)-6,9-methano-11,15-dihydroxy-16-(3-chlorophenoxy)-17,18,19,20-tetranorprosta-5,13-dienoic acid produces falls in blood pressure of 18 and 27 mmHg lasting 2 and 4 minutes at the doses of 10 and 30 μg/kg animal body weight, respectively, (5EZ,13E)-(9α,11α,15α,16R)-6,9-methano-11,15-dihydroxy-16-methylprosta-5,13-dienoic acid produces falls in blood pressure of 15 and 34 mmHg lasting 6 and 10 minutes at the doses of 5 and 10 μg/kg animal body weight, respectively, (5EZ,13E)-(9α,11α,15α)-6,9-methano-11,15-dihydroxy-15-(3-propylcyclopentyl)-16,17,18,19,20-pentanorprosta-5,13-dienoic acid produces falls in blood pressure of 18, 34 and 52 mmHg lasting 7, 9 and 14 minutes at the doses of 2, 5 and 10 μg/kg animal body weight, respectively, (5EZ,13E)-(9α,11α,15α,16S)-6,9-methano-11,15-dihydroxy-16-methylprosta-5,13-dienoic acid produces falls in blood pressure of 18 and 48 mmHg lasting 7 and 18 minutes at the doses of 2 and 5 mg/kg animal body weight respectively, (5EZ,13E)-(9α,11α,15α)-6,9-methano-11,15-dihydroxy-15-cyclohexyl-16,17,18,19,20-pentanorprosta-5,13-dienoic acid produces falls in blood pressure of 20, 44 and 58 mmHg lasting 4, 10 and 16 minutes at the doses of 5, 10 and 20 μg/kg animal body weight, respectively, (5EZ,13E)-(9α,11α, 15α,17S)-6,9-methano-11,15-dihydroxy-17,20-dimethylprosta-5,13-dienoic acid produces falls in blood pressure of 28 and 38 mmHg lasting 5 and 9 minutes at the doses of 1 and 2 μg/kg animal body weight, respectively, (5EZ,13E)-(9α,11α,15αβ)-6,9-methano-11,15-dihydroxy-15-methylprosta-5,13-dienoic acid produces falls in blood pressure of 16 and 48 mmHg lasting 12 and 22 minutes at the doses of 20 and 50 μg/kg animal body weight, respectively, (5EZ,13E)-(9α,11α,15α)-6,9-methano-11,15-dihydroxy-15-(3-ethylcyclopentyl)-16,17,18,19,20-pentanorprosta-5,13-dienoic acid produces falls in blood pressure of 10, 28 and 42 mmHg lasting 4, 6 and 12 minutes at the doses of 5, 10 and 30 μg/kg animal body weight, respectively, (5EZ,13E)-(9α,11α,15α)-6,9-methano-11,15-dihydroxy-15-(3-ethylcyclobutyl)-16,17,18,19,20-pentanorprosta-5,13-dienoic acid produces falls in blood pressure of 16, 25 and 38 mmHg lasting 3, 6 and 12 minutes at the doses of 5, 10 and 30 μg/kg animal body weight, respectively, (5EZ,13E)-(9α,11α,15α)-6,9-methano-11,15-dihydroxy-15-(4-methylcyclohexyl)-16,17,18,19,20-pentanorprosta-5,13-dienoic acid produces falls in blood pressure of 22 and 38 mmHg lasting 9 and 12 minutes at the doses of 30 and 100 μg/kg animal body weight, respectively, (5EZ,13E)-(9α,11α,15α)-6,9-methano-11,15-dihydroxy-15-cyclopentyl-16,17,18,19,20-pentanorprosta-5,13-dienoic acid produces falls in blood pressure of 28 and 47 mmHg lasting 6 and 8 minutes at the doses of 10 and 50 μg/kg animal body weight, respectively and (ii) (5EZ,13E)-(9α,11α,15α)-6,9-methano-11,15-dihydroxyprosta-5,13-dienoic acid methyl ester, (5EZ,13E)-(9α,11α,15α)-6,9-methano-11,15-dihydroxyprosta-5,13-dienoic acid, (5EZ,13E)-(9α,11α,15α,16RS)-6,9-methano-11,15-dihydroxy-16-chloroprosta-5,13-dienoic acid methyl ester, (5EZ,13E)-(9α,11α,15α)-6,9-methano-11,15-dihydroxy-16-(3-chlorophenoxy)-17,18,19,20-tetranorprosta-5,13-dienoic acid, (5EZ,13E)-(9α,11α,15α,16R)-6,9-methano-11,15-dihydroxy-16-methylprosta-5,13-dienoic acid, (5EZ,13E)-(9α,11α,15α)-6,9-methano-11,15-dihydroxy-15-(3-propylcyclopentyl)-16,17,18,19,20-pentanorprosta-5,13-dienoic acid, (5EZ,13E)-(9α,11α,15α,16S)-6,9-methano-11,15-dihydroxy-16-methylprosta-5,13-dienoic acid, (5EZ,13E)-(9α,11α,15α)-6,9-methano-11,15-dihydroxy-15-cyclohexyl-16,17,18,19,20-pentanorprosta-5,13-dienoic acid (5EZ,13E)-(9α,11α,15α,17S)-6,9-methano-11,15-dihydroxy-17,20-dimethylprosta-5,13-dienoic acid, (5EZ,13E)-(9α,11α,15αβ)-6,9-methano-11,15-dihydroxy-15-methylprosta-5,13-dienoic acid, (5EZ,13E)-(9α,11α,15α)-6,9-methano-11,15-dihydroxy-15-(3-ethylcyclopentyl)-16,17,18,19,20-pentanorprosta-5,13-dienoic acid, (5EZ,13E)-(9α,11α,15α)-6,9-methano-11,15-dihydroxy-15-(3-ethylcyclobutyl)-16,17,18,19,20-pentanorprosta-5,13-dienoic acid, (5EZ,13E)-(9α,11α,15α)-6,9-methano-11,15-dihydroxy-15-(4-methylcyclohexyl)-16,17,18,19,20-pentanorprosta-5,13-dienoic acid and (5EZ,13E)-(9α,11α,15α)-6,9-methano-11,15-dihydroxy-15-cyclopentyl-16,17,18,19,20-pentanorprosta-5,13-dienoic acid produce a 50% inhibition of adenosine diphosphate-induced blood platelet aggregation in platelet-rich plasma of rats at the concentrations of $4.9 \times 10^{-2}$, $5.8 \times 10^{-2}$, $5.0 \times 10^{-2}$, $7.5 \times 10^{-1}$, $5.8 \times 10^{-2}$, $4.7 \times 10^{-2}$, $2.48 \times 10^{-2}$, $5.8 \times 10^{-2}$, $1.4 \times 10^{-2}$, $7.5 \times 10^{-1}$, $4.8 \times 10^{-2}$, $4.7 \times 10^{-2}$, $4.7 \times 10^{-1}$ and $8.4 \times 10^{-2}$ μg/ml, respectively, in comparison with controls.

Preferred PGI$_2$ analogues of the present invention are as follows:

(5E,13E)-(9α,11α,15α)-6,9-methano-11,15-dihydroxyprosta-5,13-dienoic acid, (5E,13E)-(9α,11α,15α)-6,9-methano-11,15-dihydroxy-16-chloroprosta-5,13-dienoic acid, (5E,13E)-(9α,11α,15α)-6,9-methano-11,15-dihydroxy-16-methylprosta-5,13-dienoic acid, (5E,13E)-(9α,11α,15α)-6,9-methano-11,15-dihydroxy-17-methylprosta-5,13-dienoic acid, (5E,13E)-(9α,11α,15α)-6,9-methano-11,15-dihydroxy-18-methylprosta-5,13-dienoic acid, (5E,13E)-(9α,11α,15α)-6,9-methano-11,15-dihydroxy-19-methylprosta-5,13-dienoic acid, (5E,13E)-(9α,11α,15α)-6,9-methano-11,15-dihydroxy-16,16-dimethylprosta-5,13-dienoic acid, (5E,13E)-(9α,11α,15α)-6,9-methano-11,15-dihydroxy-16,17-dimethylprosta-5,13-dienoic acid, (5E,13E)-(9α,11α,15α)-6,9-methano-11,15-dihydroxy-16,19-dimethylprosta-5,13-dienoic acid, (5E,13E)-(9α,11α,15α)-6,9-methano-11,15-dihydroxy-16-ethylprosta-5,13-dienoic acid, (5E,13E)-(9α,11α,15α)-6,9-methano-11,15-dihydroxy-17-ethylprosta-5,13-dienoic acid, (5E,13E)-(9α,11α,15α)-6,9-methano-11,15-dihydroxy-16-propylprosta-5,13-dienoic acid, (5E,13E)-(9α,11α,15α)-6,9-methano -11,15-dihydroxy-17-propylprosta-5,13-dienoic acid, (5E,13E)-(9α,11α,15α)-6,9-methano-11,15-dihydroxy-20-methylprosta-5,13-dienoic acid, (5E,13E)-(9α,11α,15α)-6,9-methano-11,15-dihydroxy-16,20-dimethylprosta-5,13-dienoic acid,
(5E,13E)-(9α,11α,15α)-6,9-methano-11,15-dihydroxy-17,20-dimethylprosta-5,13-dienoic acid,
(5E,13E)-(9α,11α,15α)-6,9-methano-11,15-dihydroxy-16,16,20-trimethylprosta-5,13-dienoic acid,
(5E,13E)-(9α,11α,15α)-6,9-methano-11,15-dihydroxy-16-ethyl-20-methylprosta-5,13-dienoic acid,
(5E,13E)-(9α,11α,15α)-6,9-methano-11,15-dihydroxy-17-ethyl-20-methylprosta-5,13-dienoic acid,
(5E,13E)-(9α,11α,15α)-6,9-methano-11,15-dihydroxy-20-ethylprosta-5,13-dienoic acid,
(5E,13E)-(9α,11α,15α)-6,9-methano-11,15-dihydroxy-17,20-diethylprosta-5,13-dienoic acid,
(5E,13E)-(9α,11α,15α)-6,9-methano-11,15-dihydroxy-20-butylprosta-5,13-dienoic acid,
(5E,13E)-(9α,11α,15α)-6,9-methano-11,15-dihydroxy-20-hexylprosta-5,13-dienoic acid,
(5E,13E)-(9α,11α,15α)-6,9-methano-11,15-dihydroxy-15-cyclobutyl-16,17,18,19,20-pentanorprosta-5,13-dienoic acid,
(5E,13E)-(9α,11α,15α)-6,9-methano-11,15-dihydroxy-15-(1-propylcyclobutyl)-16,17,18,19,20-pentanorprosta-5,13-dienoic acid,
(5E,13E)-(9α,11α,15α)-6,9-methano-11,15-dihydroxy-15-(1-butylcyclobutyl)-16,17,18,19,20-pentanorprosta-5,13-dienoic acid,
(5E,13E)-(9α,11α,15α)-6,9-methano-11,15-dihydroxy-15-(1-pentylcyclobutyl)-16,17,18,19,20-pentanorprosta-5,13-dienoic acid,
(5E,13E)-(9α,11α,15α)-6,9-methano-11,15-dihydroxy-15-(1-hexylcyclobutyl)-16,17,18,19,20-pentanorprosta-5,13-dienoic acid,
(5E,13E)-(9α,11α,15α)-6,9-methano-11,15-dihydroxy-15-(2-methylcyclobutyl)-16,17,18,19,20-pentanorprosta-5,13-dienoic acid,
(5E,13E)-(9α,11α,15α)-6,9-methano-11,15-dihydroxy-15-(2-propylcyclobutyl)-16,17,18,19,20-pentanorprosta-5,13-dienoic acid,
(5E,13E)-(9α,11α,15α)-6,9-methano-11,15-dihydroxy-15-(3-ethylcyclobutyl)-16,17,18,19,20-pentanorprosta-5,13-dienoic acid,
(5E,13E)-(9α,11α,15α)-6,9-methano-11,15-dihydroxy-15-(3-propylcyclobutyl)-16,17,18,19,20-pentanorprosta-5,13-dienoic acid,
(5E,13E)-(9α,11α,15α)-6,9-methano-11,15-dihydroxy-15-(2,3,4-triethylcyclobutyl)-16,17,18,19,20-pentanorprosta-5,13-dienoic acid,
(5E,13E)-(9α,11α,15α)-6,9-methano-11,15-dihydroxy-15-cyclopentyl-16,17,18,19,20-pentanorprosta-5,13-dienoic acid,
(5E,13E)-(9α,11α,15α)-6,9-methano-11,15-dihydroxy-16-cyclopentyl-17,18,19,20-tetranorprosta-5,13-dienoic acid,
(5E,13E)-(9α,11α,15α)-6,9-methano-11,15-dihydroxy-17-cyclopentyl-18,19,20-trinorprosta-5,13-dienoic acid,
(5E,13E)-(9α,11α,15α)-6,9-methano-11,15-dihydroxy-16-cyclopentyl-18,19,20-trinorprosta-5,13-dienoic acid,
(5E,13E)-(9α,11α,15α)-6,9-methano-11,15-dihydroxy-18-cyclopentyl-19,20-dinorprosta-5,13-dienoic acid,
(5E,13E)-(9α,11α,15α)-6,9-methano-11,15-dihydroxy-17-cyclopentyl-19,20-dinorprosta-5,13-dienoic acid,
(5E,13E)-(9α,11α,15α)-6,9-methano-11,15-dihydroxy-15-(2-pentylcyclopentyl)-16,17,18,19,20-pentanorprosta-5,13-dienoic acid,
(5E,13E)-(9α,11α,15α)-6,9-methano-11,15-dihydroxy-15-(2,2-dimethylcyclopentyl)-16,17,18,19,20-pentanorprosta-5,13-dienoic acid,
(5E,13E)-(9α,11α,15α)-6,9-methano-11,15-dihydroxy-15-(3-ethylcyclopentyl)-16,17,18,19,20-pentanorprosta-5,13-dienoic acid,
(5E,13E)-(9α,11α,15α)-6,9-methano-11,15-dihydroxy-15-(3-propylcyclopentyl)-16,17,18,19,20-pentanorprosta-5,13-dienoic acid,
(5E,13E)-(9α,11α,15α)-6,9-methano-11,15-dihydroxy-15-(3-butylcyclopentyl)-16,17,18,19,20-pentanorprosta-5,13-dienoic acid,
(5E,13E)-(9α,11α,15α)-6,9-methano-11,15-dihydroxy-15-3-tert-butylcyclopentyl)-16,17,18,19,20-pentanorprosta-5,13-dienoic acid,
(5E,13E)-(9α,11α,15α)-6,9-methano-11,15-dihydroxy-15-(1-methyl-3-propylcyclopentyl)-16,17,18,19,20-pentanorprosta-5,13-dienoic acid,
(5E,13E)-(9α,11α,15α)-6,9-methano-11,15-dihydroxy-15-(2-methyl-3-propylcyclopentyl)-16,17,18,19,20-pentanorprosta-5,13-dienoic acid,
(5E,13E)-(9α,11α,15α)-6,9-methano-11,15-dihydroxy-15-(2-methyl-4-propylcyclopentyl)-16,17,18,19,20-pentanorprosta-5,13-dienoic acid,
(5E,13E)-(9α,11α,15α)-6,9-methano-11,15-dihydroxy-15-cyclohexyl-16,17,18,19,20-pentanorprosta-5,13-dienoic acid,
(5E,13E)-(9α,11α,15α)-6,9-methano-11,15-dihydroxy-16-cyclohexyl-17,18,19,20-tetranorprosta-5,13-dienoic acid,
(5E,13E)-(9α,11α,15α)-6,9-methano-11,15-dihydroxy-17-cyclohexyl-18,19,20-trinorprosta-5,13-dienoic acid,
(5E,13E)-(9α,11α,15α)-6,9-methano-11,15-dihydroxy-16-cyclohexyl-18,19,20-trinorprosta-5,13-dienoic acid,
(5E,13E)-(9α,11α,15α)-6,9-methano-11,15-dihydroxy-18-cyclohexyl-19,20-dinorprosta-5,13-dienoid acid,
(5E,13E)-(9α,11α,15α)-6,9-methano-11,15-dihydroxy-16-methyl-17-cyclohexyl-18,19,20-trinorprosta-5,13-dienoic acid,
(5E,13E)-(9α,11α,15α)-6,9-methano-11,15-dihydroxy-17-cyclohexyl-19,20-dinorprosta-5,13-dienoic acid,
(5E,13E)-(9α,11α,15α)-6,9-methano-11,15-dihydroxy-16-methyl-16-cyclohexyl-18,19,20-trinorprosta-5,13-dienoic acid,
(5E,13E)-(9α,11α,15α)-6,9-methano-11,15-dihydroxy-19-cyclohexyl-20-norprosta-5,13-dienoic acid,
(5E,13E)-(9α,11α,15α)-6,9-methano-11,15-dihydroxy-15-(3-ethylcyclohexyl)-16,17,18,19,20-pentanorprosta-5,13-dienoic acid,
(5E,13E)-(9α,11α,15α)-6,9-methano-11,15-dihydroxy-15-(3-isopropylcyclohexyl)-16,17,18,19,20-pentanorprosta-5,13-dienoic acid,
(5E,13E)-(9α,11α,15α)-6,9-methano-11,15-dihydroxy-15-(4-methylcyclohexyl)-16,17,18,19,20-pentanorprosta-5,13-dienoic acid,
(5E,13E)-(9α,11α,15α)-6,9-methano-11,15-dihydroxy-15-(4-ethylcyclohexyl)-16,17,18,19,20-pentanorprosta-5,13-dienoic acid,
(5E,13E)-(9α,11α,15α)-6,9-methano-11,15-dihydroxy-15-(4-propylcyclohexyl)-16,17,18,19,20-pentanorprosta-5,13-dienoic acid,
(5E,13E)-(9α,11α,15α)-6,9-methano-11,15-dihydroxy-15-(4-tert-butylcyclohexyl)-16,17,18,19,20-pentanorprosta-5,13-dienoic acid, (5E,13E)-(9α,11α,15α)-6,9-methano-11,15-dihydroxy-15-(2,6-dimethylcyclohexyl)-16,17,18,19,20-pentanorprosta-5,13-dienoic acid,
(5E,13E)-(9α,11α,15α)-6,9-methano-11,15-dihydroxy-15-(2,2-dimethylcyclohexyl)-16,17,18,19,20-pentanorprosta-5,13-dienoic acid,
(5E,13E)-(9α,11α,15α)-6,9-methano-11,15-dihydroxy-15-(2,6-dimethyl-4-propylcyclohexyl)-16,17,18,19,20-pentanorprosta-5,13-dienoic acid,
(5E,13E)-(9α,11α,15α)-6,9-methano-11,15-dihydroxy-16-(1-methylcyclohexyl)-17,18,19,20-tetranorprosta-5,13-dienoic acid,
(5E,13E)-(9α,11α,15α)-6,9-methano-11,15-dihydroxy-15-cycloheptyl-16,17,18,19,20-pentanorprosta-5,13-dienoic acid,
(5E,13E)-(9α,11α,15α)-6,9-methano-11,15-dihydroxy-16-cycloheptyl-17,18,19,20-tetranorprosta-5,13-dienoic acid,
(5E,13E)-(9α,11α,15α)-6,9-methano-11,15-dihydroxy-17-cycloheptyl-18,19,20-trinorprosta-5,13-dienoic acid,
(5E,13E)-(9α,11α,15α)-6,9-methano-11,15-dihydroxy-16-cycloheptyl-18,19,20-trinorprosta-5,13-dienoic acid,
(5E,13E)-(9α,11α,15α)-6,9-methano-11,15-dihydroxy-15-phenyl-16,17,18,19,20-pentanorprosta-5,13-dienoic acid,
(5E,13E)-(9α,11α,15α)-6,9-methano-11,15-dihydroxy-16-phenyl-17,18,19,20-tetranorprosta-5,13-dienoid acid,
(5E,13E)-(9α,11α,15α)-6,9-methano-11,15-dihydroxy-16-phenyl-18,19,20-trinorprosta-5,13-dienoic acid,
(5E,13E)-(9α,11α,15α)-6,9-methano-11,15-dihydroxy-17-phenyl-18,19,20-trinorprosta-5,13-dienoic acid,
(5E,13E)-(9α,11α,15α)-6,9-methano-11,15-dihydroxy-16-phenylprosta-5,13-dienoic acid,
(5E,13E)-(9α,11α,15α)-6,9-methano-11,15-dihydroxy-16-phenoxy-17,18,19,20-tetranorprosta-5,13-dienoic acid,
(5E,13E)-(9α,11α,15α)-6,9-methano-11,15-dihydroxy-16-(3-chlorophenoxy)-17,18,19,20-tetranorprosta-5,13-dienoic acid,
(5E,13E)-(9α,11α,15α)-6,9-methano-11,15-dihydroxy-16-(4-chlorophenoxy)-17,18,19,20-tetranorprosta-5,13-dienoic acid,
(5E,13E)-(9α,11α,15α)-6,9-methano-11,15-dihydroxy-16-(3-trifluoromethylphenoxy)-17,18,19,20-tetranorprosta-5,13-dienoic acid,
the corresponding 15-methyl and 15-ethyl analogues and corresponding (5Z)-isomers and (5EZ)-compounds and 13,14-dihydro analogues, esters, cyclodextrin clathrates, non-toxic salts and acid addition salts of such PGI$_2$, 15-methyl-PGI$_2$, 15-ethyl-PGI$_2$ and (5Z)- and (5EZ)-PGI$_2$ analogues and compounds; further preferred compounds of the present invention are the corresponding compounds of general formula II, wherein both R$^2$ and R$^3$ are hydroxy-protecting groups, particularly tetrahydropyran-2-yloxy or R$^2$ is a hydrogen atom and R$^3$ is a hydroxy-protecting group, particularly tetrahydropyran-2-yloxy.

The most preferred PGI$_2$ analogues of the invention are (5EZ,13E)-(9α,11α,15α)-6,9-methano-11,15-dihydroxy-15-(3-ethylcyclobutyl)-16,17,18,19,20-pentanorprosta-5,13-dienoic acid methyl ester, (5EZ,13E)-(9α,11α,15α)-6,9-methano-11,15-dihydroxy-15-(4-methylcyclohexyl)-16,17,18,19,20-pentanorprosta-5,13-dienoic acid methyl ester, (5EZ,13E)-(9α,11α,15α)-6,9-methano-11,15-dihydroxy-15-cyclopentyl-16,17,18,19,20-pentanorprosta-5,13-dienoic acid methyl ester, (5EZ,13E)-(9α,11α,15α)-6,9-methano-11,15-dihydroxy-15-(3-ethylcyclopentyl)-16,17,18,19,20-pentanorprosta-5,13-dienoic acid methyl ester, (5EZ,13E)-(9α,11α,15α,17S)-6,9-methano-11,15-dihydroxy-17,20-dimethylprosta-5,13-dienoic acid methyl ester, (5EZ,13E)-(9α,11α,15α)-6,9-methano-11,15-dihydroxy-15-cyclohexyl-16,17,18,19,20-pentanorprosta-5,13-dienoic acid methyl ester, (5EZ,13E)-(9α,11α,15α,16S)-6,9-methano-11,15-dihydroxy-16-methylprosta-5,13-dienoic acid methyl ester, (5EZ,13E)-(9α,11α,15α)-6,9-methano-11,15-dihydroxy-15-(3-propylcyclopentyl)-16,17,18,19,20-pentanorprosta-5,13-dienoic acid methyl ester, (5EZ,13E)-(9α,11α,15α,16R)-6,9-methano-11,15-dihydroxy-16-methylprosta-5,13-dienoic acid methyl ester, (5EZ,13E)-(9α,11α,15α)-6,9-methano-11,15-dihydroxy-16-(3-chlorophenoxy)-17,18,19,20-tetranorprosta-5,13-dienoic acid methyl ester and (5EZ,13E)-(9α,11α,15αβ)-6,9-methano-11,15-dihydroxy-15-methylprosta-5,13-dienoic acid methyl ester, and more particularly (5EZ,13E)-(9α,11α,15α)-6,9-methano-11,15-dihydroxyprosta-5,13-dienoic acid methyl ester, (5EZ,13E)-(9α,11α,15α)-methano-11,15-dihydroxyprosta-5,13-dienoic acid, (5EZ,13E)-(9α,11α,15α,16RS)-6,9-methano-11,15-dihydroxy-16-chloroprosta-5,13-dienoic acid methyl ester, (5EZ,13E)-(9α,11α,15α)-6,9-methano-11,15-dihydroxy-16-(3-chlorophenoxy)-17,18,19,20-tetranorprosta-5,13-dienoic acid, (5EZ,13E)-(9α,11α,15α,16R)-6,9-methano-11,15-dihydroxy-16-methylprosta-5,13-dienoic acid, (5EZ,13E)-(9α,11α,15α)-6,9-methano-11,15-dihydroxy-15-(3-propylcyclopentyl)-16,17,18,19,20-pentanorprosta-5,13-dienoic acid, (5EZ,13E)-(9α,11α,15α,16S)-6,9-methano-11,15-dihydroxy-16-methylprosta-5,13-dienoic acid, (5EZ,13E)-(9α,11α,15α)-6,9-methano-11,15-dihydroxy-15-cyclohexyl-16,17,18,19,20-pentanorprosta-5,13-dienoic acid, (5EZ,13E)-(9α,11α,15α,17S)-6,9-methano-11,15-dihydroxy-17,20-dimethylprosta-5,13-dienoic acid, (5EZ,13E)-(9α,11α,15αβ)-6,9-methano-11,15-dihydroxy-15-methylprosta-5,13-dienoic acid, (5EZ,13E)-(9α,11α,15α)-6,9-methano-11,15-dihydroxy-15-(3-ethylcyclopentyl)-16,17,18,19,20-pentanorprosta-5,13-dienoic acid, (5EZ,13E)-(9α,11α,15α)-6,9-methano-11,15-dihydroxy-15-(3-ethylcyclobutyl)-16,17,18,19,20-pentanorprosta-5,13-dienoic acid, (5EZ,13E)-(9α,11α,15α)-6,9-methano-11,15-dihydroxy-15-(4-methylcyclohexyl)-16,17,18,19,20-pentanorprosta-5,13-dienoic acid and (5EZ,13E)-(9α,11α,15α)-6,9-methano-11,15-dihydroxy-15-cyclopentyl-16,17,18,19,20-pentanorprosta-5,13-dienoic acid, and cyclodextrin clathrates of such acids and methyl esters and non-toxic salts of such acids.

All compounds of general formula II are new compounds and as such constitute a feature of the present invention. Compounds of general formula II include those of general formula III, IV, IVA, IVB, V, VI, XLI, XLII and XLIII. Compounds of general formulae VII, X, XI, XII, XV, XVI, XVII, XIX, XX, XXI, XXII, XXIII, XXIV, XXV, XXVII, XXVIII, XXIX, XXX, XXXI, XXXII, XXXIII, XXXIV, XXXVI, XXXVII, XXXVIII, XXXIX, XL, XLIV, XLIVA, XLIVB, XLV, XLVI, XLVII, XLVIII, , XLIX, L, LI, LII, LIII, LIV, LV, LVI, LVII, LVIII, LIX, LX, LXI and LXII are also novel compounds of the present invention.

The following Reference Examples and Examples illustrate the preparation of new prostaglandin I$_2$ analogues of the present invention. In the Reference Examples and Examples 'TLC', 'IR', 'NMR' and 'MS' represent respectively 'Thin layer chromatography', 'Infrared absorption spectrum', 'Nuclear magnetic resonance spectrum' and 'Mass spectrum'. Where solvent ratios are specified, e.g. in chromatographic separations, the ratios are by volume. The solvents in parentheses show the developing solvent used in the thin layer chromatography. Except when specified otherwise, infrared spectra are recorded by the liquid film method, and nuclear magnetic resonance spectra are recorded in deuterochloroform ($CDCl_3$) solution.

REFERENCE EXAMPLE 1

4α-Methoxycarbonylmethyl-5β-benzyloxymethylcyclopent2-en-1α-ol

To a solution of 23.6 g of 4α-carboxymethyl-5β-benzyloxymethylcyclopent-2-en-1α-ol [prepared as described in J. Amer. Chem. Soc., 93, 1492 (1971)] in 200 ml of acetone were added 27.6 g of potassium carbonate and 113.6 g of methyl iodide. The mixture was allowed to stand at room temperature for 50 minutes and then refluxed for 2 hours. The reaction mixture was filtered and the filtrate was concentrated under reduced pressure. The residue was purified by column chromatography on silica gel using a mixture of cyclohexane and ethyl acetate (2:1) as eluant to give 24.9 g of the title compound having the following physical characteristics:

TLC (cyclohexane:ethyl acetate=1:1):Rf=0.32.
IR: $\nu$=3400, 1740, 1455, 1440, 1368, 1171, 1100, 743, 705 $cm^{-1}$.
NMR: $\delta$=7.20 (5H, s), 5.67 (2H, s), 4.55 (1H, m), 4.47 (2H, s), 3.58 (3H, s).

REFERENCE EXAMPLE 2

3α-Ethoxycarbonylmethyl-4α-methoxycarbonylmethyl-5β-benzyloxymethylcyclopent-1-ene A mixture of 4.14 g of the cyclopent-2-en-1α-ol compound (prepared as described in Reference Example 1), 8.2 ml of triethyl orthoacetate and 0.17 g of hydroquinone was reacted for 20 hours at 145° C., distilling away the ethanol produced, and the mixture obtained was concentrated under reduced pressure. The residue was purified by column chromatography on silica gel using a mixture of chloroform and cyclohexane (3:1) as eluant to give 2.70 g of the title compound having the following physical characteristics:

TLC (benzene-ethyl acetate=2:1): Rf=0.38.
IR: $\nu$=1736, 1372, 1260, 1163, 1100, 1029, 737, 698 $cm^{-1}$.
NMR: $\delta$=7.20 (5H, s), 5.67 (2H, m), 4.44 (2H, s), 4.07 (2H, q), 3.56 (3H, s), 3.40 (2H, d), 1.23 (3H, t).
MS: m/e=346 (M+), 228, 206, 193, 192, 191, 179, 178, 177, 165, 164, 163, 151, 119, 105, 93, 92, 91, 79, 78, 77.

REFERENCE EXAMPLE 3

3-Oxo-6-syn-benzyloxymethyl-cis-bicyclo[3,3,0]oct-7ene

A solution of 2.70 g of the cyclopent-1-ene compound (prepared as described in Reference Example 2) in 7 ml of benzene was added to a solution of 3.5 g of potassium tert-butoxide and 60 ml of benzene at room temperature and the mixture stirred at 65°–70° C. for 1.5 hours. The reaction mixture was then poured into a mixture of 2N hydrochloric acid and ice and extracted with diethyl ether. The extract was washed with water, a saturated aqueous solution of sodium bicarbonate, water and a saturated aqueous solution of sodium chloride, dried over anhydrous sodium sulphate and concentrated under reduced pressure. The residue was mixed with 7 ml of hexamethylphosphoramide and 0.35 ml of water and the mixture stirred at 155°–160° C. for 15 minutes. The reaction mixture was then poured into 40 ml of ice-water and extracted with diethyl ether. The extract was washed with a saturated aqueous solution of sodium chloride, dried over anhydrous sodium sulphate and concentrated under reduced pressure. The residue was purified by column chromatography on silica gel using a mixture of cyclohexane and ethyl acetate (5:1) as eluant to give 1.58 g of the title compound having the following physical characteristics:

TLC (cyclohexane:ethyl acetate=2:1): Rf=0.39.
IR: $\nu$=3040, 2900, 2060, 1740, 1452, 1401, 1363, 1159, 1100, 737, 698 $cm^{-1}$.
NMR: $\delta$=7.33 (5H, s), 5.72 (2H, m), 4.53 (2H, s), 3.41 (2H, dd), 3.30–3.60 (1H, m), 2.78 (2H, m).
MS: m/e=242 (M+), 121, 92, 91, 79, 77.

REFERENCE EXAMPLE 4

6-Syn-benzyloxymethyl-7-anti-hydroxy-8-syn-bromo-cis-bicyclo[3,3,0]octan-3-one

A mixture of 1.02 g of the oct-7-ene compound (prepared as described in Reference Example 3), 21 ml of dimethyl sulphoxide, 0.21 ml of water and 1.5 g of N-bromosuccinimide was stirred at 22°–24° C. for 25 minutes. The reaction mixture was poured into ice-water and extracted with diethyl ether. The extract was washed with water and a saturated aqueous solution of sodium chloride, dired over anhydrous sodium sulphate and concentrated under reduced pressure. The residue was purified by column chromatography on silica gel using a mixture of cyclohexane and ethyl acetate (6:1) as eluant to give 1.06 g of the title compound having the following physical characteristics:

TLC (benzene:ethyl acetate=2:1): Rf=0.36.
IR: $\nu$=3420, 3040, 2860, 1738, 1453, 1403, 1105, 740, 700 $cm^{-1}$;
NMR: $\delta$=7.33 (5H, s), 4.54 (2H, s), 4.12 (1H, t), 3.75 (1H, t), 3.62 (2H, dd).
MS: m/c=340 (M+), 338, 108, 107, 92, 91, 79.

REFERENCE EXAMPLE 5

6-Syn-benzyloxymethyl-7-anti-hydroxy-cis-bicyclo[3,3,0]octan-3-one

A mixture of 54 mg of the bromo compound (prepared as described in Reference Example 4), 1 ml of benzene, 0.09 ml of tributyltin hydride and a small quantity of α,α'-azobisisobutyronitrile was irradiated with light from a high pressure mercury lamp at room temperature for 30 minutes. The reaction mixture was mixed with an excess of a saturated aqueous solution of sodium carbonate, allowed to stand at room temperature for 1.5 hours, and then extracted with diethyl ether. The extract was washed with a saturated aqueous solution of sodium chloride, dried over anhydrous sodium sulphate and concentrated under reduced pressure. The residue was purified by column chromatography on silica gel using a mixture of cyclohexane and ethyl acetate (3:1) as eluant to give 29 mg of the title compound having the following physical characteristics:

TLC (cyclohexane:ethyl acetate=1:3): Rf=0.33;
IR: $\nu$=3430, 3040, 2930, 2860, 1737, 1451, 1403, 1099, 742, 700 $cm^{-1}$.

NMR: δ=7.32 (5H, s), 4.52 (2H, s), 4.08 (1H, q), 3.55 (2H, m).

REFERENCE EXAMPLE 6

6-Syn-benzyloxymethyl-7-anti-(tetrahydropyran-2-yloxy)-8-syn-bromo-cis-bicyclo[3,3,0]octan-3-one To a solution of 1.01 g of the bromo compound (prepared as described in Reference Example 4) in 10 ml of methylene chloride was added a small quantity of p-toluenesulphonic acid and 0.405 ml of 2,3-dihydropyran. The mixture was stirred at room temperature for 30 minutes. The reaction mixture was then poured into a saturated aqueous solution of sodium bicarbonate and extracted with diethyl ether. The extract was washed with a saturated aqueous solution of sodium chloride, dried over anhydrous sodium sulphate and concentrated under reduced pressure. The residue was purified by column chromatography on silica gel using a mixture of cyclohexane and ethyl acetate (2:1) as eluant to give 1.28 g of the title compound having the following physical characteristics:

TLC (cyclohexane:ethyl acetate=2:1): Rf=0.36.
IR: ν=3040, 2950, 2860, 1742, 1451, 1404, 1356, 1200, 1121, 1078, 1035, 968, 740, 700 cm$^{-1}$.
NMR: δ=7.34 (5H, s), 5.00–4.65 (1H, m), 4.55 (2H, s), 4.50–3.20 (6H, m).

REFERENCE EXAMPLE 7

6-Syn-benzyloxymethyl-7-anti-(tetrahydropyran-2-yloxy)cis-bicyclo[3,3,0]octan-3-one Proceeding as described in Reference Example 5, but using the bromo compound (prepared as described in Reference Example 6), there was obtained the title compound (60% yield) having the following physical characteristics:

TLC (cyclohexane:ethyl acetate=2:1): Rf=0.35.
IR: ν=3040, 2940, 2860, 1739, 1450, 1353, 1200, 1113, 1074, 1020, 970, 738, 698 cm$^{-1}$.
NMR: δ=7.20 (5H, s), 4.57 (1H, m), 4.46 (2H, s), 4.10 (1H, m), 3.46 (2H, m).

REFERENCE EXAMPLE 8

6-Syn-benzyloxymethyl-7-anti-hydroxy-cis-bicyclo[3,3,0]octan-3-one

A mixture of 260 mg of the tetrahydropyran-2-yl compound (prepared as described in Reference Example 7), 1.5 ml of 2N-hydrochloric acid and 3 ml of tetrahydrofuran was stirred at room temperature for 2 hours. The reaction mixture was extracted with diethyl ether. The extract was washed with a saturated aqueous solution of sodium bicarbonate and a saturated aqueous solution of sodium chloride, dried over anhydrous sodium sulphate and concentrated under reduced pressure. The residue was purified by column chromatography on silica gel using a mixture of cyclohexane and ethyl acetate (1:1) as eluant to give 156 mg of the title compound having the same physical characteristics as the compound prepared as described in Reference Example 5.

REFERENCE EXAMPLE 9

6-Syn-benzyloxymethyl-7-anti-(tetrahydropyran-2-yloxy)cis-bicyclo[3,3,0]octan-3-one Proceeding as described in Reference Example 6, but using the hydroxy compound as described in Reference Example 5 or 8, there was obtained the title compound having the same physical characteristics as the compound prepared as described in Reference Example 7 (yield 99%).

REFERENCE EXAMPLE 10

1α-(Tetrahydropyran-2-yloxy)-4α-methoxycarbonylmethyl-5β-benzyloxymethylcyclopent-2-ene Proceeding as described in Reference Example 6, but using the cyclopenten-1α-ol compound prepared as described in Reference Example 1, there was obtained the title compound (99% yield) having the following physical characteristic:

TLC (cyclohexane:ethyl acetate=7:3): Rf=0.43.

REFERENCE EXAMPLE 11

1α-(Tetrahydropyran-2-yloxy)-4α-(2-oxo-3-ethoxycarbonylpropyl)-5β-benzyloxymethylcyclopent-2-ene Under an atmosphere of argon, 40 ml of a 1.5M solution of butyllithium in hexane was added to a solution of 6.06 g of diisopropylamine in 100 ml of tetrahydrofuran at −78° C. and the mixture was stirred at the same temperature for 15 minutes. To the amide solution obtained a solution of 4.2 g of ethyl acetate in 30 ml of tetrahydrofuran was added dropwise slowly at −78° C., and the mixture was stirred at the same temperature for 30 minutes. To the solution obtained 7.20 g of the methoxycarbonyl compound (prepared as described in Reference Example 10) in 50 ml of tetrahydrofuran was added dropwise slowly at −78° C. and the reaction mixture was stirred at −20° C. for one hour and for a further 30 minutes at 0° C. The reaction mixture was acidified with acetic acid to pH 3 poured into 200 ml of water and the mixture extracted with ethyl acetate. The extract was dried over anhydrous magnesium sulphate and concentrated under reduced pressure. The residue was purified by column chromatography on silica gel using a mixture of cyclohexane and ethyl acetate (17:3) as eluant to give 7.05 g of the title compound having the following physical characteristics:

TLC (cyclohexane:ethyl acetate=7:3): Rf=0.30.
IR: ν=1745, 1720, 1625, 1455, 1370, 1320, 1205, 1115, 1030, 745, 705 cm$^{-1}$.
NMR: δ=7.25 (5H, m), 5.75 (2H, m), 4.48 (2H, broad s), 4.16 and 4.13 (2H, each q), 1.27 and 1.24 (3H, each t).

REFERENCE EXAMPLE 12

1α-(Tetrahydropyran-2-yloxy)-4α-(2-oxo-3-diazo-3-ethoxycarbonylpropyl)-5β-benzyloxymethylcyclopent-2-ene Under an atmosphere of argon, a mixture of 8.75 g of the oxo compound (prepared as described in Reference Example 11), 110 ml of acetonitrile and 5.31 g of triethylamine was mixed with a solution of 4.97 g of p-toluenesulphonyl azide in 10 ml of acetonitrile at 0° C. and the mixture stirred at the same temperature for 5 minutes and then at room temperature for 14 hours. The reaction mixture was concentrated under reduced pressure. The residue was purified by column chromatography on silica gel using a mixture of cyclohexane and diethyl ether (7:3) as eluant to give 8.89 g of the title compound having the following physical characteristics:

TLC (cyclohexane:methylene chloride:ethyl acetate=5:5:1): Rf=0.49.
IR: ν=2130, 1720, 1655, 1375, 1313, 1133, 1110, 1010, 742, 700 cm$^{-1}$.

NMR: δ=7.32 (5H, m), 5.36 (2H, m), 4.54 (2H, broad s), 4.28 (2H, q), 1.31 (3H, t).
MS: m/e=414 (M+ −28).

REFERENCE EXAMPLE 13

2-Ethoxycarbonyl-6-syn-benzyloxymethyl-7-anti(tetrahydropyran-2-yloxy)-cis-tricyclo[3,3,0,0$^{2.8}$]octan-3-one Under an atmosphere of argon, a mixture of 3.64 g of the diazo compound (prepared as described in Reference Example 12), 10.4 g of anhydrous cupric sulphate and 60 ml of benzene was refluxed for 25 hours. The reaction mixture was filtered and the filtrate was concentrated under reduced pressure. The residue was purified by column chromatography on silica gel using a mixture of cyclohexane and ethyl acetate (3:1) as eluant to give 2.2 g of the title compound having the following physical characteristics:
TLC (cyclohexane:diethyl ether=2:3): Rf=0.33 and 0.28.
IR: ν=1760, 1740, 1725, 1452, 1373, 1315, 1260, 1230, 1200, 1122, 1030, 979, 742, 703 cm$^{-1}$.
NMR: δ=7.34 (5H, m), 4.54 (2H, broad s), 4.19 (2H, q), 1.25 (3H, t).
MS: m/e=414 (M+).

REFERENCE EXAMPLE 14

2-Ethoxycarbonyl-6-syn-benzyloxymethyl-7-anti(tetrahydropyran-2-yloxy)-cis-bicyclo[3,3,0]octan-3-one Proceeding as described in Reference Example 5, but using the tricyclo[3,3,0,0$^{2.8}$]octan-3-one compound prepared as described in Reference Example 13, there was obtained the title compound (yield 27%) having the following physical characteristics:
TLC (cyclohexane:ethyl acetate=7:3): Rf=0.45;
MS: m/e=416 (M+).

REFERENCE EXAMPLE 15

6-Syn-benzyloxymethyl-7-anti-(tetrahydropyran-2-yloxy)cis-bicyclo[3,3,0]octan-3-one A solution of 5 mg of the 2-ethoxycarbonyl compound (prepared as described in Reference Example 14), 1 ml of hexamethylphosphoramide and 1 drop of water was stirred at 160° C. for 15 minutes. The reaction mixture was diluted with 30 ml of diethyl ether, washed with water and a saturated aqueous solution of sodium chloride, dried over anhydrous magnesium sulphate and concentrated under reduced pressure. The residue was dissolved in 1 ml of methylene chloride, mixed with 0.01 ml of 2,3-dihydropyran and a small quantity of p-toluenesulphonic acid, and stirred at room temperature for 30 minutes. To the reaction mixture was added 0.01 ml of triethylamine and the mixture was then concentrated under reduced pressure. The residue was purified by column chromatography on silica gel using a mixture of cyclohexane and ethyl acetate (9:1) as eluant to give 4 mg of the title compound having the same physical characteristics as the compound described in Reference Example 7.

REFERENCE EXAMPLE 16

2α-Methoxycarbonylmethyl-3β-benzyloxymethyl-4α-(tetrahydropyran-2-yloxy)cyclopentan-1-one To a solution of 47 g of 2-oxa-6-syn-benzyloxymethyl-7-anti-(tetrahydropyran-2-yloxy)-cis-bicyclo[3,3,0]octan-3-one [described in J. Amer. Chem. Soc., 93, 1490 (1971)] in 160 ml of methanol was added 100 ml of 2N sodium hydroxide aqueous solution and the mixture was stirred at room temperature for 30 minutes. The reaction mixture was concentrated under reduced pressure and the residue was acidified with 15% (w/v) hydrochloric acid to pH 3, cooling the mixture with an ice-bath and then extracted with ethyl acetate. The extract was washed with a saturated aqueous solution of sodium chloride, dried over anhydrous magnesium sulphate and concentrated under reduced pressure to half the original volume of ethyl acetate. The solution obtained was cooled with an ice bath. Diazomethaneetherate was added until the pale-yellow colour did not vanish. The mixture was then concentrated under reduced pressure to give a methyl ester compound.
A solution of 28.4 g of chromyl chloride (CrO$_2$Cl$_2$) in 70 ml of carbon tetrachloride was added dropwise slowly to a mixture of 35 ml of tert-butanol, 44.5 ml of pyridine and 650 ml of methylene chloride at −78° C., and then the methyl ester compound in 200 ml of methylene chloride was added at room temperature and the mixture stirred at 35° C. for 2.5 hours. The reaction mixture was mixed with 2.5 ml of dimethyl sulphide and stirred at room temperature for 10 minutes. The mixture was concentrated under reduced pressure to a volume of 200–300 ml, then poured into 1 liter of diethyl ether and the mixture was stirred vigorously for 15 minutes. The solution obtained was filtered and the filtrate was washed with 1N hydrochloric acid, water and a saturated aqueous solution of sodium chloride, dried over anhydrous magnesium sulphate and concentrated under reduced pressure. The residue was purified by column chromatography on silica gel using a mixture of cyclohexane and ethyl acetate (5:1) as eluant to give 40 g of the title compound having the following physical characteristics:
TLC (benzene:ethyl acetate=2:1): Rf=0.51.
IR: ν=1740, 1495, 1450, 1435, 1370, 1200, 970 cm$^{-1}$.
NMR: δ=7.20 (5H, s), 4.60 (1H, m), 4.50 (2H, s), 4.45–4.00 (1H, m), 3.60 (3H, s).

REFERENCE EXAMPLE 17

1-Methoxycarbonylmethylidene-2-methoxycarbonylmethyl-3β-benzyloxymethyl-4α-(tetrahydropyran-2-yloxy)cyclopentane Under an atmosphere of nitrogen, 205 ml of a 1.55M solution of butyllithium in hexane was added dropwise to a solution of 44.5 ml of diisopropylamine and 1 liter of tetrahydrofuran at −78° C. and the mixture was stirred at the same temperature for 15 minutes. To the solution obtained, methyltrimethylsilyl acetate [prepared as described in J. Org. Chem., 32, 3535 (1967), boiling point 70°–75° C./105 mm Hg] (50 g) was added dropwise and the mixture stirred at −78° C. for 20 minutes. To the reaction mixture, 38 g of the cyclopentan-1-one compound (prepared as described in Reference Example 16) in 100 ml of tetrahydrofuran was added dropwise and the mixture was stirred at −78° C. for 2 hours. The reaction mixture was mixed with 23 ml of acetic acid and concentrated under reduced pressure. The residue was dissolved in ethyl acetate, washed with 1N hydrochloric acid, water and a saturated aqueous solution of sodium chloride, dried over anhydrous magnesium sulphate and concentrated under reduced pressure. The residue was purified by column chromatography on silica gel using a mixture of cyclohexane and ethyl acetate (6:1) as eluant to give 19.8 g of the title compound having the following physical characteristics:

TLC (benzene:ethyl acetate=2:1): Rf=0.58.

IR: $\nu$=1740, 1720, 1655, 1495, 1440, 1210, 1030 cm$^{-1}$.

NMR: $\delta$=7.20 (5H, s), 5.70 (1H, m), 4.60 (1H, m), 4.45 (2H, s), 4.10 (1H, m), 3.63 (3H, s), 3.60 (3H, s).

REFERENCE EXAMPLE 18

1,2-Bis-(methoxycarbonylmethyl)-3$\beta$-benzyloxymethyl-4$\alpha$-(tetrahydropyran-2-yloxy)cyclopentane To a solution of 29 g of the methylidene compound (prepared as described in Reference Example 17) and 600 ml of ethanol was added 10 g of 5% (w/w) palladium on charcoal and hydrogenation was carried out at room temperature. The reaction mixture was filtered and the filtrate was concentrated under reduced pressure. The residue was purified by column chromatography on silica gel using a mixture of cyclohexane and ethyl acetate (5:1) as eluant to give 26.5 g of the title compound having the following physical characteristics:

TLC (benzene:ethyl acetate=2:1): Rf=0.52.

IR: $\nu$=1740, 1495, 1440, 1020 cm$^{-1}$.

NMR: $\delta$=7.20 (5H, s), 4.60 (1H, m), 4.40 (2H, s), 4.20–3.85 (1H, m), 3.60 (3H, s), 3.50 (3H, s).

REFERENCE EXAMPLE 19

A mixture of 2(or 4)-methoxycarbonyl-6-syn-benzyloxymethyl-7-anti-(tetrahydropyran-2-yloxy)-cis-bicyclo[3,3,0]octan-3-one and 2(or 4)-methoxycarbonyl-6-anti-benzyloxymethyl-7-syn-(tetrahydropyran-2-yloxy)cis-bicyclo[3,3,0]octan-3-one Under an atmosphere of nitrogen, a solution of 26.5 g of the bis-(methoxycarbonylmethyl) compound (prepared as described in Reference Example 18) in 100 ml of benzene was added dropwise to a solution of 27.4 g of potassium tert-butoxide in 700 ml of benzene at 30° C. and the mixture was stirred at 70°–80° C. for 4 hours. The reaction mixture was mixed with 20 ml of acetic acid, cooling the mixture with an ice-bath and the mixture then poured into 150 ml of water and extracted with ethyl acetate. The extract was washed with water and a saturated aqueous solution of sodium chloride, dried over anhydrous magnesium sulphate and concentrated under reduced pressure. The residue was purified by column chromatography on silica gel using a mixture of cyclohexane and ethyl acetate (5:1) as eluant to give 8.45 g of the title compound having the following physical characteristics:

TLC (cyclohexane:ethyl acetate=2:1): Rf=0.38.

IR: $\nu$=1760, 1730, 1660, 1620, 1495, 1450, 1025, 700 cm$^{-1}$.

NMR: $\delta$=7.20 (5H, s), 4.60 (1H, m), 4.45 (2H, s), 4.15 (1H, m).

REFERENCE EXAMPLE 20

6-Syn-benzyloxymethyl-7-anti-(tetrahydropyran-2-yloxy)cis-bicyclo[3,3,0]octan-3-one Preceeding as described in Reference Example 15, but using a mixture of the 2(or 4)-methoxycarbonyl compounds prepared as described in Reference Example 19, there was obtained the title compound (yield 25%) having the same physical characteristics as those of the compound prepared as described in Reference Example 7.

REFERENCE EXAMPLE 21

6-Syn-hydroxymethyl-7-anti-(tetrahydropyran-2-yloxy)cis-bicyclo[3,3,0]octan-3-one Under an atmosphere of hydrogen, a mixture of 3.78 g of the benzyloxymethyl compound (prepared as described in Reference Example 7, 9, 15 or 20), 1.4 g of 5% (w/w) palladium on charcoal, 70 ml of ethanol and 7 ml of acetic acid was stirred at room temperature for 3 hours. The reaction mixture was filtered and the filtrate was concentrated under reduced pressure to half of its original volume. The concentrated solution was poured into a saturated aqueous solution of sodium bicarbonate, the mixture extracted with ethyl acetate, the extract dried over anhydrous magnesium sulphate and concentrated under reduced pressure. The residue was purified by column chromatography on silica gel using a mixture of cyclohexane and ethyl acetate (1:1) as eluant to give 2.42 g of the title compound having the following physical characteristics:

TLC (cyclohexane:ethyl acetate=2:1): Rf=0.07.

IR: $\nu$=2945, 2870, 1740 cm$^{-1}$.

NMR: $\delta$=4.77–4.52 (1H, m), 4.28–3.36 (5H, m), 2.95–1.35 (16H, m).

REFERENCE EXAMPLE 22

3-(4-Methoxycarbonyl-EZ-butylidene)-6-syn-hydroxymethyl-7-anti-(tetrahydropyran-2-yloxy)-cis-bicyclo[3,3,0]octane Under an atmosphere of nitrogen, to a solution of 2.22 g of (4-carboxybutyl)triphenylphosphonium bromide in 5 ml of dimethyl sulphoxide was added, dropwise, 5 ml of a 2M solution of dimsyl sodium in dimethyl sulphoxide at room temperature, 510 mg of the hydroxymethyl compound (prepared as described in Reference Example 21) in dimethyl sulphoxide was then added and the mixture was stirred at room temperature for 16 hours. The reaction mixture was poured into ice-water containing potassium carbonate and then washed with a mixture of ethyl acetate and diethyl ether (1:1). The aqueous layer was acidified to pH 3 with a saturated aqueous solution of oxalic acid and extracted with a mixture of ethyl acetate and diethyl ether (1:1). The extract was washed with water and a saturated aqueous solution of sodium chloride, dried over anhydrous magnesium sulphate, and concentrated under reduced pressure to half of its original volume. To the solution obtained was added diazomethane-etherate until the pale-yellow colour did not vanish and the mixture was then concentrated under reduced pressure. The residue was purified by column chromatography on silica gel using a mixture of cyclohexane and ethyl acetate (3:1) as eluant to give 520 mg of the title compound having the following physical characteristics:

TLC (benzene:ethyl acetate=2:1): Rf=0.31.

IR: $\nu$=3450, 1740, 1440, 1025, 980 cm$^{-1}$.

NMR: $\delta$=5.22 (1H, m), 4.65 (1H, m), 4.07–3.40 (5H, m), 3.66 (3H, s).

REFERENCE EXAMPLE 23

3-(4-Methoxycarbonyl-EZ-butylidene)-6-syn-formyl-7-anti-(tetrahydropyran-2-yloxy)-cis-bicyclo[3,3,0]octane Under an atmosphere of nitrogen, to a solution of 4.7 ml of pyridine in 80 ml of methylene chloride was added 2.9 g of chromium trioxide; the mixture was stirred at room temperature for 10 minutes and then 14 g of infusorial earth were added. To the solution obtained was added, at 0°–5° C., a solution of 1.04 g of the butylidene compound (prepared as described in Reference Example 22) in 10 ml of methylene chloride and the mixture obtained was stirred for 15 minutes. To the solution obtained were added 4 ml of allyl alcohol and the mixture was then stirred for 10 minutes; 22 g of sodium bisulphate were then added and the mixture stirred at 0°–5° C. for 10 minutes. The reaction mixture was filtered through a layer of anhydrous magnesium sulphate. The filtrate was filtered again through a layer of silica gel and concentrated under reduced pressure at a temperature below 0° C. to give 800 mg of the title compound having the following physical characteristic:

TLC (benzene:ethyl acetate=2:1): Rf=0.57.

REFERENCE EXAMPLE 24

(5EZ,13E)-(9α,11α,16RS)-6,9-Methano-11-(tetrahydropyran-2-yloxy)-15-oxo-16-chloroprosta-5,13-dienoic acid methyl ester Under an atmosphere of argon, a solution of 234 mg of dimethyl 2-oxo-3RS-chloroheptylphosphonate in 2 ml of tetrahydrofuran was added drop-wise to a suspension of 23 mg of sodium hydride (content 63.5%) in 3 ml of tetrahydrofuran, and the mixture was stirred at room temperature for 1.5 hours. A solution of 80 mg of the formyl compound (prepared as described in Reference Example 23) in 1 ml of tetrahydrofuran was added at room temperature and the mixture stirred for 7 hours. The reaction mixture was neutralized with acetic acid, filtered through a layer of silica gel and the filtrate was concentrated under reduced pressure. The residue was purified by column chromatography on silica gel using a mixture of cyclohexane and ethyl acetate (10:1) as eluant to give 86 mg of the title compound having the following physical characteristics:

TLC (cyclohexane:ethyl acetate=2:1): Rf=0.54.
IR: $\nu$=1740, 1700, 1683, 1628, 1440, 1035, 1080, 1040, 1025, 978 cm$^{-1}$.
NMR: $\delta$=7.20–6.80 (1H, m), 6.40 (1H, dd), 5.20 (1H, m), 3.60 (3H, s).

Proceeding as described above, the following compounds having the physical characteristics given below were obtained from the appropriate phosphonate and the formyl compound prepared as described in Reference Example 23.

(a)

(5EZ,13E)-(9α,11α)-6,9-Methano-11-(tetrahydropyran-2-yloxy)-15-oxo-15-(3-ethylcyclobutyl)-16,17,18,19,20-pentanorprosta-5,13-dienoic acid methyl ester TLC (cyclohexane:ethyl acetate=2:1): Rf=0.66.
IR: $\nu$=2950, 2865, 1742, 1695, 1670, 1630 cm$^{-1}$.
NMR: $\delta$=6.96–6.58 (1H, m), 6.25–5.97 (1H, m), 5.37–5.13 (1H, m), 4.76–4.49 (1H, m), 3.67 (3H, s), 0.98–0.68 (3H, s).

(b)

(5EZ,13E)-(9α,11α)-6,9-Methano-11-(tetrahydropyran-2-yloxy)-15-oxo-15-(3-ethylcyclopentyl)-16,17,18,19,20-pentanorprosta-5,13-dienoic acid methyl ester TLC (cyclohexane:ethyl acetate=2:1): Rf=0.72.
IR: $\nu$=2945, 2860, 1740, 1695, 1655, 1625 cm$^{-1}$.
NMR: $\delta$=7.00–6.63 (1H, m), 6.34–6.05 (1H, dd), 5.35–5.10 (1H, m), 4.72–4.50 (1H, m), 3.67 (3H, s), 1.00–0.88 (3H, t).

(c)

(5EZ,13E)-(9α,11α,17S)-6,9-Methano-11-(tetrahydropyran-2-yloxy)-15-oxo-17,20-dimethylprosta-5,13-dienoic acid methyl ester IR: $\nu$=2900, 2940, 2880, 1745, 1700, 1670, 1630, 1440, 1210, 1080, 980 cm$^{-1}$.
NMR: $\delta$=7.10–5.80 (2H, m), 5.50–4.80 (1H, m), 4.80–4.20 (1H, m), 4.20–3.00 (3H, m), 3.60 (3H, s).
MS: m/e=390 (M$^+$−34).

(d)

(5EZ,13E)-(9α,11α)-6,9-Methano-11-(tetrahydropyran-2-yloxy)-15-oxo-15-cyclohexyl-16,17,18,19,20-pentanorprosta-5,13-dienoic acid methyl ester IR: $\nu$=2955, 2945, 2855, 1745, 1700, 1670, 1630, 1450, 1380, 1260, 1210, 1130, 1080, 1030, 980 cm$^{-1}$.
NMR: $\delta$=7.00–5.70 (2H, m), 5.30–4.80 (1H, m), 4.70–4.20 (1H, m), 4.10–3.00 (3H, m), 3.60 (3H, s).

(e)

(5EZ,13E)-(9α,11α,16S)-6,9-Methano-11-(tetrahydropyran-2-yloxy)-15-oxo-16-methylprosta-5,13-dienoic acid methyl ester TLC (cyclohexane:ethyl acetate=2:1): Rf=0.74.
IR: $\nu$=2865, 1740, 1695, 1665, 1625 cm$^{-1}$.
NMR: $\delta$=7.02–6.67 (1H, m), 6.28–6.07 (1H, m), 5.36–5.10 (1H, m), 4.73–4.49 (1H, m), 3.66 (3H, s), 2.18 (3H, d), 0.93–0.77 (3H, m).

(f)

(5EZ,13E)-(9α,11α)-6,9-Methano-11-(tetrahydropyran-2-yloxy)-15-oxo-15-(3-propylcyclopentyl)-16,17,18,19,20-pentanorprosta-5,13-dienoic acid methyl ester TLC (cyclohexane:ethyl acetate=2:1): Rf=0.79.
IR: $\nu$=2950, 2870, 1740, 1695, 1663, 1625 cm$^{-1}$.
NMR: $\delta$=7.00–6.62 (1H, m), 6.33–6.04 (1H, m), 5.37–5.10 (1H, m), 4.72–4.49 (1H, m), 3.66 (3H, s), 1.01–0.76 (3H, m).

(g)

(5EZ,13E)-(9α,11α,16R)-6,9-Methano-11-(tetrahydropyran-2-yloxy)-15-oxo-16-methylprosta-5,13-dienoic acid methyl ester TLC (cyclohexane:ethyl acetate=2:1): Rf=0.80.
IR: $\nu$=2970, 2940, 2870, 1745, 1700, 1665, 1630, 1460, 1380, 1210, 1130, 1080, 1040, 980 cm$^{-1}$.
NMR: $\delta$=7.00–5.80 (2H, m), 5.40–4.90 (1H, m), 4.70–4.30 (1H, m), 4.10–3.00 (3H, m), 3.60 (3H, s).

(h)

(5EZ,13E)-(9α,11α)-6,9-Methano-11-(tetrahydropyran-2-yloxy)-15-oxo-16-(3-chlorophenoxy)-17,18,19,20-tetranorprosta-5,13-dienoic acid methyl ester TLC (benzene:ethyl acetate=2:1): Rf=0.70.
IR: $\nu$=1740, 1695, 1625, 1600, 1480, 1040, 980 cm$^{-1}$.
NMR: $\delta$=7.30–6.55 (5H, m), 6.30 (1H, d), 5.20 (1H, m), 4.70–4.30 (3H, m), 3.60 (3H, s).

(i)

(5EZ,13E)-(9α,11α)-6,9-Methano-11-(tetrahydropyran-2-yloxy)-15-oxoprosta-5,13-dienoic acid methyl ester TLC (benzene:ethyl acetate=2:1): Rf=0.70.

(j)

(5EZ,13E)-(9α,11α)-6,9-Methano-11-(tetrahydropyran-2-yloxy)-15-oxo-15-(4-methylcyclohexyl)-16,17,18,19,20-pentanorprosta-5,13-dienoic acid methyl ester TLC (cyclohexane:ethyl acetate=1:1): Rf=0.68.
NMR: δ=7.0-5.66 (2H, m), 5.65-4.80 (1H, m), 4.50 (1H, broad s), 3.56 (3H, s).

(k)

(5EZ,13E)-(9α,11α)-6,9-Methano-11-(tetrahydropyran-2-yloxy)-15-oxo-15-cyclopentyl-16,17,18,19,20-pentanorprosta-5,13-dienoic acid methyl ester TLC (cyclohexane:ethyl acetate=1:1): Rf=0.67;
NMR: δ=7.0-6.27 (1H, m), 6.27-5.67 (1H, m), 5.5-4.8 (1H, m), 4.8-4.23 (1H, m), 3.53 (3H, s).

REFERENCE EXAMPLE 25

(5EZ,13E)-(9α,11α)-6,9-Methano-11-hydroxy-15-oxo-15-(3-ethylcyclobutyl)-16,17,18,19,20-pentanorprosta-5,13-dienoic acid methyl ester A solution of 130 mg of the 15-oxo compound [prepared as described in Reference Example 24(a)] in 5 ml of a mixture of acetic acid, tetrahydrofuran and water (3:1:1) was stirred at 50° C. for 1.5 hours. The reaction mixture was neutralized with a saturated aqueous solution of sodium bicarbonate and extracted with ethyl acetate. The extract was washed with a saturated aqueous solution of sodium chloride, dried over anhydrous magnesium sulphate and concentrated under reduced pressure. The residue was purified by column chromatography on silica gel using a mixture of cyclohexane and ethyl acetate as eluant to give 91 mg of the title compound having the following physical characteristics:

TLC (cyclohexane:ethyl acetate=2:1): Rf=0.22.
IR: ν=2950, 2860, 1740, 1695, 1665, 1622 cm$^{-1}$.
MS: m/e=374 (M+), 356, 330.

Proceeding as described above, the following compounds having the physical characteristics given below were obtained from the corresponding 15-oxo compounds prepared as described in Reference Example 24(j) and (k) respectively.

(a)

(5EZ,13E)-(9α,11α)-6,9-Methano-11-hydroxy-15-oxo-15-(4-methylcyclohexyl)-16,17,18,19,20-pentanorprosta-5,13-dienoic acid methyl ester TLC (cyclohexane:ethyl acetate=1:1): Rf=0.43.
NMR: δ=7.0-5.67 (2H, m), 5.6-4.8 (1H, m), 3.58 (3H, s).

(b)

(5EZ,13E)-(9α,11α)-6,9-Methano-11-hydroxy-15-oxo-15-cyclopentyl-16,17,18,19,20-pentanorprosta-5,13-dienoic acid methyl ester TLC (cyclohexane:ethyl acetate=1:1): Rf=0.44.
IR: ν=3450, 2960, 2875, 1740, 1690, 1660, 1620, 1450, 1435 cm$^{-1}$.
NMR: δ=6.72 (1H, dd), 6.10 (1H, d), 5.5-4.92 (1H, m). 3.6 (3H, s).

EXAMPLE 1

(5EZ,13E)-(9α,11α,15αβ,16RS)-6,9-Methano-11-(tetrahydropyran-2-yloxy)-15-hydroxy-16-chloroprosta-5,13-dienoic acid methyl ester To a solution of 86 mg of the 15-oxo compound (prepared as described in Reference Example 24) in 2 ml of methanol was added 8.2 mg of sodium borohydride and the mixture was stirred at −20° to −30° C. for 30 minutes. The reaction mixture was acidified to pH 3 with acetic acid and diluted with ethyl acetate. The solution was washed with water, a saturated aqueous solution of sodium bicarbonate and a saturated aqueous solution of sodium chloride, dried over anhydrous magnesium sulphate and concentrated under reduced pressure to give 85 mg of the title compound having the following physical characteristics:

TLC (cyclohexane:ethyl acetate=2:1): RF=0.41.
IR: ν=3400, 1740, 978 cm$^{-1}$.

Proceeding as described above, the following compounds having the physical characteristics given below were obtained from the corresponding 15-oxo compounds prepared as described in Reference Example 24 (b)–(i), 25 and 25 (a)–(b), respectively:

(a)

(5EZ,13E)-(9α,11α,15α)-6,9-Methano-11,15-dihydroxy-15-(3-ethylcyclobutyl)-16,17,18,19,20-pentanorprosta-5,13-dienoic acid methyl ester

[purified by column chromatography on silica gel using a mixture of methylene chloride and ethyl acetate (1:1) as eluant] was prepared from the product of Reference Exaample 25:
TLC (methylene chloride:ethyl acetate=1:1): RF=0.34 (15β-isomer, Rf=0.64).
IR: ν=2950, 2850, 1740 cm$^{-1}$.
NMR: δ=5.57-5.36 (2H, m), 5.34-5.08 (1H, m), 3.68 (3H, s), 3.35-3.10 (2H, broad s), 0.92-0.68 (3H, m).
MS: m/e=358 (M+ −18), 340, 327, 314.

(b) (5EZ,13E)-(9α,11α,15α)-6,9-Methano-11,15-dihydroxy-15-(4-methylcyclohexyl)-16,17,18,19,20-pentanorprosta-5,13-dienoic acid methyl ester

[purified by column chromatography on silica gel using a mixture of methylene chloride and ethyl acetate (1:1) as eluant] was prepared from the product of Reference Example 25(a):
TLC (cyclohexane:ethyl acetate=1:1): Rf=0.21.
IR: ν=3490, 2950, 2860, 1740, 1450, 1375, 1315, 1250, 1200, 1170, 1080, 970 cm$^{-1}$.
NMR: δ=5.8-4.68 (3H, m), 4.35-3.30 (2H, m), 3.65 (3H, s), 3.0 (2H, broad s).

(c)

(5EZ,13E)-(9α,11α,15α)-6,9-Methano-11,15-dihydroxy-15-cyclopentyl-16,17,18,19,20-pentanorprosta-5,13-dienoic acid methyl ester

[purified by column chromatography on silica gel using a mixture of methylene chloride and ethyl acetate (1:1) as eluant] was preapred from the product of Reference Example 25(b):
TLC (cyclohexane:ethyl acetate=1:1): RF=0.14;
IR: ν=3380, 2950, 2875, 1740, 1450, 1430, 1315, 1250, 1195, 1170, 1130, 1085, 1020, 970 cm$^{-1}$.
NMR: δ=5.87-4.83 (3H, m), 4.27-3.4 (2H, m), 3.6 (3H, s).

(d)

(5EZ,13E)-(9α,11α,15αβ)-6,9-Methano-11-(tetrahydropyran-2-yloxy)-15-hydroxy-15-(3-ethylcyclo-pentyl)-16,17,18,19,20-pentanorprosta-5,13-dienoic acid methyl ester was prepared from the product of Reference Example 24(b):

TLC (cyclohexane:ethyl acetate=2:1): RF=0.50.
IR: ν=3450, 2950, 2870, 1740 cm⁻¹.

(e)

(5EZ,13E)-(9α,11α,15αβ,17S)-6,9-Methano-11-(tetrahydropyran-2-yloxy)-15-hydroxy-17,20-dimethyl-prosta-5,13-dienoic acid methyl ester was prepared from the product of References Example 24(c):

IR: ν=3450, 2940, 1745, 1440, 1200, 1140, 980 cm⁻¹.

(f)

(5EZ,13E)-(9α,11α,15αβ)-6,9-Methano-11-(tetrahydropyran-2-yloxy)-15-hydroxy-15-cyclohexyl-16,17,18,19,20-pentanorprosta-5,13-dienoic acid methyl ester was prepared from the product of Reference Example 24 (d):

IR: ν=3450, 2945, 2850, 1745, 1450, 1350, 1250, 1200, 1170, 1120, 1080, 1020, 980, 920, 870 cm⁻¹.

(g)

(5EZ,13E)-(9α,11α,15αβ,16S)-6,9-Methano-11-(tetrahydropyran-2-yloxy)-15-hydroxy-16-methylprosta-5,13-dienoic acid methyl ester was prepared from the product of Reference Example 24(e):

IR: ν=2950, 2870, 1740 cm⁻¹.

(h)

(5EZ,13E)-(9α,11α,15αβ)-6,9-Methano-11-(tetrahydropyran-2-yloxy)-15-hydroxy-15-(3-propylcyclopentyl)-16,17,18,19,20-pentanorprosta-5,13-dionoic acid methyl ester was prepared from the product of Reference Example 24(f): IR: ν=2950, 2865, 1740 cm⁻¹.

(i)

(5EZ,13E)-(9α,11α,15αβ,16R)-6,9-Methano-11-(tetrahydropyran-2-yloxy)-15-hydroxy-16-methylprosta-5,13-dienoic acid methyl ester was prepared from the product of Reference Example 24(g): IR: ν=3450, 2950, 2870, 1745, 1440, 1380, 1250, 1200, 1140, 1080, 1020, 980, 920, 870, 810 cm⁻¹.

(j)

(5EZ,13E)-(9α,11α,15αβ)-6,9-Methano-11-(tetrahydropyran-2-yloxy)-15-hydroxy-16-(3-chlorophenoxy)-17,18,19,20-tetranorprosta-5,13-dienoic acid methyl ester was prepared from the product of Reference Example 24(h):

TLC (benzene:ethyl acetate=2:1): Rf=0.44.
IR: ν=3430, 1740, 1600, 1480, 1440, 1030, 980 cm⁻¹.
NMR: δ=7.30–6.60 (4H, m), 5.56 (2H, m), 5.20 (1H, m), 4.70–4.20 (2H, m).

(k)

(5EZ,13E)-(9α,11α,15αβ)-6,9-Methano-11-(tetrahydropyran-2-yloxy)-15-hydroxyprosta-5,13-dienoic acid methyl ester was prepared from the product of Reference Example 24(i):

TLC (benzene:ethyl acetate=2:1): Rf=0.48 and 0.41.

EXAMPLE 2

(5EZ,13E)-(9α,11α,15αβ)-6,9-Methano-11-(tetrahydropyran-2-yloxy)-15-hydroxy-15-methylprosta-5,13-dienoic acid methyl ester A mixture of 16 mg of the 15-oxo compound [prepared as described in Reference Example 24(i)], 0.01 ml of a 3.478M solution of trimethyl aluminium in hexane and 1 ml of benzene was stirred at room temperature for 20 minutes. To the reaction mixture obtained was added a saturated aqueous solution of ammonium chloride and the mixture was extracted with ethyl acetate. The extract was washed with a saturated aqueous solution of sodium chloride, dried over anhydrous magnesium sulphate and concentrated under reduced pressure. The residue was purified by column chromatography on silica gel using a mixture of cyclohexane and ethyl acetate (2:1) as eluant to give 10 mg of the title compound having the following physical characteristics:

TLC (cyclohexane:ethyl acetate=5:2): Rf=0.21.
MS: m/e=462 (M+), 360, 344, 342, 316.

EXAMPLE 3

(5EZ,13E)-(9α,11α,15α,16RS)-6,9-Methano-11,15-dihydroxy-16-chloroprosta-5,13-dienoic acid methyl ester To a solution of 85 mg of the tetrahydropyran-2-yloxy compound (prepared as described in Example 1) in 2 ml of methanol was added as small quantity of p-toluenesulphonic acid and the mixture was stirred at room temperature for 1.5 hours. 0.1 ml of triethylamine was added and the solution was then concentrated under reduced pressure. The residue was purified by column chromatography on silica gel using a mixture of cyclohexane and ethyl acetate as eluant to give 27 mg of the title compound having the following physical characteristics:

TLC (ethyl acetate:cyclohexane=2:1): Rf=0.37 (15β-isomer, Rf=0.46).
IR: ν=3400, 1740, 1438, 1250, 1170, 1132, 1080, 972 cm⁻¹.
NMR: δ=5.80–5.40 (2H, m), 5.24 (1H, m), 4.30–3.60 (3H, m), 3.68 (3H, s).
MS: m/e=362 and 360 (M+ −18), 344, 336, 326, 300, 179.

Proceeding as described above, the following compounts having the physical characteristics given below were obtained from the corresponding tetrahydropyran-2-yloxy compounds prepared as described in Examples 1 (d)–(k) or 2:

(a)

(5EZ,13E)-(9α,11α,15α)-6,9-Methano-11,15-dihydroxy-15-(3-ethylcyclopentyl)-16,17,18,19,20-pentanorprosta-5,13-dienoic acid methyl ester was prepared from the product of Example 1(d):

TLC (methylene chloride:ethyl acetate=1:1): Rf=0.26 (15β-isomer, Rf=0.51).
IR: ν=2950, 2860, 1740 cm⁻¹.

NMR: δ=5.57–5.40 (2H, m), 5.35–5.10 (1H, m), 3.67 (3H, s), 3.25–2.80 (2H, m), 0.99–0.76 (3H, m).
MS: m/e=372 (M+ −18), 354, 328.

(b)
(15EZ,13E)-(9α,11α,15α,17S)-6,9-Methano-11,15-dihydroxy-17,20-dimethylprosta-5,13-dienoic acid methyl ester was prepared from the product of Example 1(e):
TLC (methylene chloride:ethyl acetate=1:1): Rf=0.33 (15β-isomer, Rf=0.59).
IR: ν=3350, 2940, 1745, 1440, 1380, 970 cm$^{-1}$;
NMR: δ=5.60–5.40 (2H, m), 5.40–5.10 (1H, m), 4.20–4.00 (1H, m), 3.90–3.00 (1H, m), 3.67 (3H, s), 3.10–2.90 (2H, m), 1.00–0.70 (6H, m).
MS: m/e=374 (M+ −18), 356, 343, 330.

(c)
(5EZ,13E)-(9α,11α,15α)-6,9-Methano-11,15-dihydroxy-15-cyclohexyl-16,17,18,19,20-pentanorprosta-5,13-dienoic acid methyl ester was prepared from the product of Example 1(f):
TLC (methylene chloride:ethyl acetate=1:1): Rf=0.35 (15β-isomer, Rf=0.56).
IR: ν=3400, 2950, 2860, 1745, 1450, 1380, 1330, 1260, 1180, 1130, 1090, 1010, 980, 900 cm$^{-1}$.
NMR: δ=5.60–5.40 (2H, m), 5.40–5.00 (1H, m), 3.90–3.40 (2H, m), 3.68 (3H, s).
MS: m/e=358 (M+ −18), 340, 327, 314, 293, 275, 257.

(d)
(5EZ,13E)-(9α,11α,15α,16S)-6,9-Methano-11,15-dihydroxy-16-methylprosta-5,13-dienoic acid methyl ester was prepared from the product of Example 1(g):
TLC (benzene:ethyl acetate=2:1): Rf=0.24 (15β-isomer, Rf=0.37).
IR: ν=3360, 1740, 980 cm$^{-1}$.
NMR: δ=5.70–5.00 (3H, m), 4.20–3.90 (1H, m), 3.90–3.50 (1H, m), 3.67 (3H, s), 1.10–0.70 (6H, m).
MS: m/e=360 (M+ −18), 342, 329, 316, 293, 275.

(e)
(5EZ,13E)-(9α,11α,15α)-6,9-Methano-11,15-dihydroxy-15-(3-propylcyclopentyl)-16,17,18,19,20-pentanorprosta-5,13-dienoic acid methyl ester was prepared from the product of Example 1(h):
TLC (benzene:ethyl acetate=2:1): Rf=0.26 (15β-isomer, Rf=0.39).
IR: ν=3360, 1740, 980 cm$^{-1}$.
NMR: δ=5.70–5.00 (3H, m), 4.20–3.90 (1H, m), 3.90–3.50 (1H, m), 3.68 (3H, s), 1.00–0.80 (3H, m).
MS: m/e=386 (M+ −18), 368, 355, 342, 337.

(f)
(5EZ,13E)-(9α,11α,15α,16R)-6,9-Methano-11,15-dihydroxy-16-methylprosta-5,13-dienoic acid methyl ester was prepared from the product of Example 1(i):
TLC (methylene chloride:ethyl acetate=1:1): Rf=0.30 (15β-isomer, Rf=0.53).
IR: ν=3400, 2955, 2945, 2870, 1745, 1440, 1380, 1250, 1170, 1080, 970 cm$^{-1}$.
NMR: δ=5.60–5.40 (2H, m), 5.40–5.10 (1H, m), 4.00–3.50 (2H, m), 3.67 (3H, s), 3.20–2.80 (2H, m), 1.00–0.70 (6H, m).
MS: m/e=360 (M+ −18), 342, 329, 316, 293, 275, 257, 179.

(g)
(5EZ,13E)-(9α,11α,15α)-6,9-Methano-11,15-dihydroxy-16-(3-chlorophenoxy)-17,18,19,20-tetranorprosta-5,13-dienoic acid methyl ester was prepared from the product of Example 1(j):
TLC (benzene:ethyl acetate=2:1): Rf=0.36 (15β-isomer, Rf=0.45).
IR: ν=3380, 1740, 1600, 1480, 1440, 1040, 975 cm$^{-1}$.
NMR: δ=7.21–6.74 (4H, m), 5.66 (2H, m), 5.23 (1H, m), 4.47 (1H, m), 3.95 (2H, m), 3.66 and 3.67 (3H, each s).

(h)
(5EZ,13E)-(9α,11α,15α)-6,9-Methano-11,15-dihydroxyprosta-5,13-dienoic acid methyl ester was prepared from the product of Example 1(k):
TLC (benzene:ethyl acetate=2:1): Rf=0.22 (15β-isomer, Rf=0.35).
IR: ν=3660, 1740, 1440, 1170, 975 cm$^{-1}$.
NMR: δ=5.50 (2H, m), 5.24 (1H, m), 4.02 (1H, m), 3.90–3.53 (1H, m), 3.67 (3H, s), 0.90 (3H, m).

(i)
(5EZ,13E)-(9α,11α,15αβ)-6,9-Methano-11,15-dihydroxy-15-methylprosta-5,13-dienoic acid methyl ester
was prepared from the product of Example 2:

TLC (cyclohexane:ethyl acetate=1:1): Rf=0.23.

EXAMPLE 4

(5EZ,13E)-(9α,11α,15α)-6,9-Methano-11,15-dihydroxy-15-(3-ethylcyclobutyl)-16,17,18,19,20-pentanorprosta-5,13-dienoic acid.

52 mg of the methyl ester compound [prepared as described in Example 1(a)] in 1.3 ml of methnol was mixed with 1.38 ml of a 0.5N aqueous solution of sodium hydroxide and the mixture was stirred at 50° C. for 1.5 hours. To the solution obtained was added 4 ml of 0.2N hydrochloric acid and the mixture was extracted with ethyl acetate. The extract was washed with saturated aqueous solution of sodium chloride, dried over anhydrous magnesium sulphate and concentrated under reduced pressure. The residue was purified by column chromatography on silica gel using a mixture of cyclohexane and ethyl acetate (1:1) as eluant to give 50 mg of the title compound having the following physical characteristics:
TLC (ethyl acetate:formic acid=400:5): Rf=0.64.
IR: ν=2970, 2935, 2870, 2800–2350, 1715 cm$^{-1}$.
NMR: δ=5.97–5.60 (3H, m), 5.57–5.36 (2H, m), 5.34–5.08 (1H, m), 4.15–3.50 (2H, m), 0.94–0 (3H, m).
MS: m/e=344 (M+ −18), 326, 300.

Proceeding as described above, the following compounds having the physical characteristics given below were obtained from the corresponding methyl ester compounds prepared as described in Examples 1(b)–(c) and 3(a)–(i):

(a)
(5EZ,13E)-(9α,11α,15α)-6,9-Methano-11,15-dihydroxy-15-(3-ethylcyclopentyl)-16,17,18,19,20-pentanorprosta-5,13-dienoic acid was prepared from the product of Example 3(a):
TLC (ethyl acetate:formic acid=400:5): Rf=0.65.
IR: ν=2950, 2855, 2800–2400, 1715 cm$^{-1}$.
NMR: δ=5.86–5.58 (3H, m), 5.56–5.40 (2H, m), 5.34–5.10 (1H, m), 3.95–3.54 (2H, m), 1.00–0.76 (3H, m).

MS: m/e=358 (M+ −18), 340, 314.

(b)
(5EZ,13E)-(9α,11α,15α,17S)-6,9-Methano-11,15-dihydroxy-17,20-dimethylprosta-6,13-dienoic acid was prepared from the product of Example 3(b):
TLC (ethyl acetate:triethylamine=99:1): Rf=0.20.
IR: $\nu$=3350, 2940, 2650, 1715, 1460, 1380, 980 cm$^{-1}$.
NMR: $\delta$=5.80–5.30 (5H, m), 5.30–5.00 (1H, m), 4.30–4.00 (1H, m), 3.90–3.50 (1H, m), 1.00–0.70 (6H, m).
MS: m/e=360 (M+ −18), 342, 318, 165.

(c)
(5EZ,13E)-(9α,11α,15α)-6,9-Methano-11,15-dihydroxy-15-cyclohexyl-16,17,18,19,20-pentanorprosta-5,13-dienoic acid was prepared from the product of Example 3(c):
TLC (ethyl acetate): Rf=0.49.
IR: $\nu$=3350, 2945, 2850, 2650, 1715, 1450, 1250, 1080, 980, 900 cm$^{-1}$.
NMR: $\delta$=5.70–5.35 (2H, m), 5.35–5.10 (1H, m), 5.10–4.80 (3H, m), 4.00–3.50 (2H, m).
MS: m/e=344 (M+ −18), 326, 300, 261, 243, 218.

(d)
(5EZ,13E)-(9α,11α,15α,16S)-6,9-Methano-11,15-dihydroxy-16-methylprosta-5,13-dienoic acid was prepared from the product of Example 3(d):
TLC (ethyl acetate): Rf=0.37 and 0.28.
IR: $\nu$=3000–2350, 1720 cm$^{-1}$.
NMR: $\delta$=5.59–5.10 (6H, m), 3.98–3.56 (2H, m), 2.59–2.30 (6H, m), 1.01–0.75 (6H, m).
MS: m/e=346 (M+ −18), 338, 302, 261, 243.

(e)
(5EZ,13E)-(9α,11α,15α)-6,9-Methano-11,15-dihydroxy-15-(3-propylcyclopentyl)-16,17,18,19,20-pentanorprosta-5,13-dienoic acid was prepared from the product of Example 3(e):
TLC (ethyl acetate:formic acid=400:5): Rf=0.65.
IR: $\nu$=2950, 2870, 1710 cm$^{-1}$;
NMR: $\delta$=5.75–5.36 (5H, m), 5.33–5.10 (1H, m), 3.94–3.53 (2H, m), 0.99–0.75 (3H, m).
MS: m/e=372 (M+ −18), 354, 328.

(f)
(5EZ,13E)-(9α,11α,15α,16R)-6,9-Methano-11,15-dihydroxy-16-methylprosta-5,13-dienoic acid was prepared from the product of Exmple 3(f):
TLC (ethyl acetate): Rf=0.58 and 0.50.
IR: $\nu$=3350, 2955, 2945, 2870, 2650, 1715, 1460, 1380, 1250, 1130, 1080, 970 cm$^{-1}$.
NMR: $\delta$=5.70–5.40 (2H, m), 5.40–4.80 (4H, m), 4.00–3.50 (2H, m), 1.00–0.70 (6H, m).
MS: m/e=346 (M+ −18), 328, 302, 261.

(g)
(5EZ,13E)-(9α,11α,15α)-6,9-Methano-11,15-dihydroxy-16-(3-chlorophenoxy)-17,18,19,20-tetranorprosta-5,13-dienoic acid was prepared from the product of Example 3(g):
TLC (ethyl acetate:formic acid=400:5): Rf=0.41.
IR: $\nu$=3350, 1740, 1715, 1600, 1480, 1255, 1040, 975 cm$^{-1}$.
NMR: $\delta$=7.20–6.70 (4H, m), 6.00–5.40 (5H, m), 5.20 (1H, m), 4.45 (1H, m), 3.95 (2H, m), 3.70 (1H, m).
MS: m/e=402 (M+ −18), 384, 358, 275, 261, 257, 243, 231, 165.

(h)
(5EZ,13E)-(9α,11α,15α)-6,9-Methano-11,15-dihydroxyprosta-5,13-dienoic acid was prepared from the product of Example 3(h): TLC (ethyl acetate:formic acid=400:5): Rf=0.35.
IR: $\nu$3340, 1715, 1250, 1080, 970 cm$^{-1}$.
NMR: $\delta$=5.45 (2H, m), 5.20 (1H, m), 4.00 (1H, m), 3.64 (1H, m), 0.89 (3H, m).

(i)
(5EZ,13E)-(9α,11α,15αβ)-6,9-Methano-11,15-dihydroxy-15-methylprosta-5,13-dienoic acid was prepared from the product of Example 3(i):
TLC (ethyl acetate: Rf=0.25.
IR: $\nu$=3400, 1740, 1715, 1380, 1240, 975 cm$^{-1}$.
NMR: $\delta$=5.80–5.05 (3H, m), 4.00–3.50 (1H, m), 0.88 (3H, m).

(j)
(5EZ,13E)-(9α,11α,15α)-6,9-Methano-11,15-dihydroxy-15-(4-methylcyclohexyl)-16,17,18,19,20-pentanorprosta-5,13-dienoic acid was prepared from the product of Example 1(b):
TLC (ethyl acetate:methanol=95:5): Rf=0.42 and 0.45.
NMR: $\delta$=5.94 (3H, board s), 5.7–5.0 (3H, m), 4.06–3.28 (2H, m).
MS: m/e=358 (M+ −18), 341, 340, 314, 261, 243, 218, 165, 97, 55, 41.

(k)
(5EZ,13E)-(9α,11α,15α)-6,9Methano-11,15-dihydroxy-15-cyclopentyl-16,17,18,19,20-pentanorprosta-5,13-dienoic acid was prepared from the product of Example 1(c):
TLC (ethyl acetate:methanol=95:5): Rf=0.41 and 0.47.
IR: $\nu$=3350, 2950, 2875, 2650, 1710, 1450, 1430, 1410, 1375, 1250, 1220, 1130, 1080, 1020, 970 cm$^{-1}$.
NMR: "=6.55–4.95 (6H, m), 4.2–3.35 (2H, m).
MS: m/e=330 (M+ −18), 312, 286, 261, 243, 217, 165, 91, 69, 41.

REFERENCE EXAMPLE 26

2α-Methoxycarbonylmethyl-3β-methoxymethyl-4-(tetrahydropyran-2-yloxy)cyclopentan-1-one 90 ml of a 2N sodium hydroxide solution were added to a solution of 32.5 g of 2-oxa-6-syn-methoxymethyl-7-anti-(tetrahydropyran-2-yloxy)-cis-bicyclo[3,3,0]octan-3-one in 160 ml of methanol and the reaction mixture was stirred at room temperature for 30 minutes and then concentrated under reduced pressure. The residue was acidified to pH 3 with 15% (w/v) hydrochloric acid, cooling the mixture with an ice-bath, and extracted with ethyl acetate. The extract was washed with a saturated aqueous solution of sodium chloride, dried over anhydrous magnesium sulphate and concentrated under reduced pressure to half the original volume of ethyl acetate. To the solution obtained was added an ethereal solution of diazomethane, cooling the mixture with an ice-bath, until the reaction mixture turned pale yellow. The reaction mixture was concentrated under reduced pressure to give a methyl ester compound.

A solution of 20.9 g of chromyl chloride in 70 ml of carbon tetrachloride was added dropwise slowly to a mixture of 25.6 ml of tert-butanol, 34 ml of pyridine and 400 ml of methylene chloride at −78° C. To the solution obtained was added the methyl ester compound prepared as described above in 100 ml of methylene chloride at room temperature and the mixture was stirred at room temperature for 1.5 hours and then at 35° C. for 2.5 hours. The reaction mixture was mixed with 2 ml of dimethyl sulphide and stirred at room temperature for 10 minutes. The reaction mixture was then concentrated under reduced pressure until the volume of the mixture was 100 to 200 ml. The solution was poured into 1 liter of diethyl ether and the mixture was stirred vigorously for 30 minutes. The solution was filtered, and the filtrate washed with 1N hydrochloric acid, water, a saturated aqueous solution of sodium bicarbonate and a saturated aqueous solution of sodium chloride, dried over anhydrous magnesium sulphate and concentrated under reduced pressure. The residue was purified by column chromatography on silica gel using a mixture of cyclohexane and ethyl acetate (4:1) as eluant to give 28.4 g of the title compound having the following physical characteristics:

TLC (diethyl ether): Rf=0.58.
IR: $\nu = 1740, 1440, 1200, 1030$ cm$^{-1}$.
NMR: $\delta = 4.60$ (1H, m), 3.60 (3H, s), 3.30 (3H, s).

2-Oxa-6-syn-methoxymethyl-7-anti-(tetrahydropyran-2-yloxy)-cis-bicyclo[3,3,0]octan-3-one, used as a starting material in the above procedure, was prepared as follows:

A mixture of 30 g of 2-oxa-6-syn-methoxymethyl-7-anti-acetoxy-cis-bicyclo[3,3,0]octan-3-one [prepared as described in J. Amer. Chem. Soc., 92, 397 (1970)] in 400 ml of methanol and 18 g of potassium carbonate were stirred at room temperature for 30 minutes. To the reaction mixture was added 16 ml of glacial acetic acid and the mixture was then concentrated under reduced pressure. The residue was dissolved in ethyl acetate, and the solution was washed with water and a saturated aqueous solution of sodium chloride, dried over anhydrous magnesium sulphate and concentrated under reduced pressure to give 23 g of 2-oxa-6-syn-methoxymethyl-7-anti-hydroxy-cis-bicyclo[3,3,0]octan-3-one having the following Rf value:

TLC (benzene:ethyl acetate=1:1): Rf=0.08.

A solution of 23 g of the 7-anti-hydroxy compound (prepared as described above) in 350 ml of methylene chloride was mixed with 20 ml of 2,3-dihydropyran and 200 mg of p-toluenesulphonic acid, and the mixture was stirred at room temperature for 1 hour. To the reaction mixture 10 ml of triethylamine was added and the mixture was then concentrated under reduced pressure. The residue was purified by column chromatography on silica gel using a mixture of cyclohexane and ethyl acetate (1:1) as eluant to give 28 g of 2-oxa-6-syn-methoxymethyl-7-anti-(tetrahydropyran-2-yloxy)-cis-bicyclo[3,3,0]octan-3-one having the following physical characteristics:

TLC (benzene:ethyl acetate=1:1): Rf=0.26.
NMR: $\delta = 4.90$ (1H, m), 4.60 (1H, m), 4.20–3.30 (5H, m), 3.27 (3H, s).

REFERENCE EXAMPLE 27

1-Methoxycarbonylmethylidene-2-methoxycarbonylmethyl-3β-methoxymethyl-4α-(tetrahydropyran-2-yloxy)cyclopentane Under an atmosphere of nitrogen, 195 ml of a 1.55M solution of n-butyllithium in hexane was added dropwise to a solution of 42.6 ml of diisopropylamine in 1 liter of tetrahydrofuran at −78° C., and the mixture was stirred at the same temperature for 15 minutes. To the solution obtained, 44 g of methyltrimethylsilyl acetate [prepared as described in J. Org. Chem., 32, 3535 (1967), boiling point: 70°–75° C./105 mm Hg] was added dropwise and the mixture was stirred at −78° C. for 20 minutes. To the solution thus obtained, a solution of 23.4 g of the ketone compound (prepared as described in Reference Example 26) in 80 ml of tetrahydrofuran was added dropwise and the mixture stirred at −78° C. for 1.5 hours. The reaction mixture was mixed with 20 ml of acetic acid and concentrated under reduced pressure. The residue was dissolved in ethyl acetate, washed with water and a saturated aqueous solution of sodium chloride, dried over anhydrous magnesium sulphate and concentrated under reduced pressure. The residue was purified by column chromatography on silica gel using a mixture of cyclohexane and ethyl acetate (3:1) as eluant to give 15.3 g of the title compound having the following physical characteristics:

TLC (benzene:ethyl acetate=2:1): Rf=0.49.
IR: $\nu = 1740, 1720, 1655, 1440, 1360, 1220, 1030$ cm$^{-1}$.
NMR: $\delta = 5.70$ (1H,m), 4.60 (1H,m), 4.05 (1H,m), 3.60 (6H,s), 3.25 (3H, s).

REFERENCE EXAMPLE 28

1,2-Bis(methoxycarbonylmethyl)-3β-methoxymethyl-4α-(tetrahydropyran-2-yloxy)cyclopentane To a solution of 24 g of the methylidene compound (prepared as described in Reference Example 27) in 500 ml of ethanol was added 7 g of 5% (w/w) palladium on charcoal and hydrogenation was then carried out at room temperature. The reaction mixture was filtered and the filtrate was concentrated under reduced pressure. The residue was purified by column chromatography on silica gel using a mixture of methylene chloride and ethyl acetate (6:1) as eluant to give 23.4 g of the title compound having the following physical characteristics:

TLC (benzene:ethyl acetate=2:1): Rf=0.44.
IR: $\nu = 1740, 1440, 1200, 1020$ cm$^{-1}$.
NMR: $\delta = 4.63$ (1H,m), 3.67 (6H,s), 3.31 (3H,s).

REFERENCE EXAMPLE 29

Mixture of 2(or 4)-methoxycarbonyl-6-syn-methoxymethyl-7-anti-(tetrahydropyran-2-yloxy)-cis-bicyclo[3,3,0]octan-3-one and 2(or 4)-methoxycarbonyl-6-anti-methoxymethyl-7-syn-(tetrahydropyran-2-yloxy)-cis-bicyclo[3,3,0]octan-3-one Under an atmosphere of nitrogen, 22.8 g of the bis(-methoxycarbonylmethyl) compound (prepared as described in Reference Example 28) in 100 ml of benzene was added dropwise to a solution of 28.5 g of potassium tert-butoxide in 700 ml of benzene at 40° C., and the mixture was stirred at 75° C. for 4 hours. The reaction mixture was mixed with 20 ml of glacial acetic acid, cooling the mixture with an ice-bath, and then extracted with ethyl acetate. The extract was washed with water and a saturated aqueous solution of sodium chloride, dried over anhydrous magnesium sulphate and concentrated under reduced pressure. The residue was purified by column chromatography on silica gel using a mixture of cyclohexane and ethyl acetate (4:1) as eluant to give 9.86 g of the title compound having the following physical characteristics:

TLC (benzene:ethyl acetate=2:1): Rf=0.48.
IR: $\nu$=1760, 1730, 1660, 1620 cm$^{-1}$.

REFERENCE EXAMPLE 30

6-Syn-methoxymethyl-7-anti-(tetrahydropyran-2-yloxy)-cis-bicyclo[3,3,0]octan-3-one A solution of 9.56 g of the mixture of 2(or 4)-methoxycarbonyl compounds (prepared as described in Reference Example 29) in 28.5 ml of hexamethylphosphoramide (HMPA) was mixed with 1.5 ml of water and the mixture stirred at 175° C. for 15 minutes. The reaction mixture was then poured into 200 ml of ice-water, and extracted with diethyl ether. The extract was washed with a saturated aqueous solution of sodium chloride, dried over anhydrous magnesium sulphate and concentrated under reduced pressure. The residue was purified by column chromatography on silica gel using a mixture of cyclohexane and ethyl acetate (3:1) as eluant to give 4.07 g of the title compound having the following physical chracteristics:

TLC (benzene:ethyl acetate=2:1): Rf=0.27.
IR: $\nu$=1740, 1120, 1020, 975 cm$^{-1}$.
NMR: $\delta$=4.64 (1H,m), 4.20–3.73 (3H,m), 3.34 (3H,s).

REFERENCE EXAMPLE 31

6-Syn-methoxymethyl-7-anti-hydroxy-cis-bicyclo[3,3,0]octan-3-one

A mixture of 1.25 g of the 7-tetrahydropyran-1-yloxy compound (prepared as described in Reference Example 30), 35 ml of tetrahydrofuran and 15 ml of 1N hydrochloric acid was stirred at room temperature for 3.5 hours. The reaction mixture was extracted with ethyl acetate. The extract was washed with a saturated aqueous solution of sodium bicarbonate and a saturated aqueous solution of sodium chloride, dried over anhydrous magnesium sulphate and concentrated under reduced pressure. The residue was purified by column chromatography on silica gel using a mixture of cyclohexane and ethyl acetate (1:1) as eluant to give 800 mg of the title compound having the following physical characteristics:

TLC (benzene:ethyl acetate=1:1): Rf=0.10.
IR: $\nu$=3420, 1740, 1400, 1100 cm$^{-1}$.
NMR: $\delta$=4.20–3.95 (1H,m), 3.75–3.30 (2H,m), 3.47 (3H,s).

REFERENCE EXAMPLE 32

6-Syn-methoxymethyl-7-anti-benzoyloxy-cis-bicyclo[3,3,0]octan-3-one 1 ml of benzoyl chloride was added to a mixture of a solution of 800 mg of the 7-hydroxy compound (prepared as described in Reference Example 31) in 25 ml of methylene chloride and 1.6 ml of pyridine at room temperature and the mixture was stirred for 2.5 hours. 0.2 ml of ethanol was added to the mixture which was then stirred at room temperature for 15 minutes. The reaction mixture was extracted with ethyl acetate. The extract was washed with 1N hydrochloric acid, water and a saturated aqueous solution of sodium chloride, dried over anhydrous magnesium sulphate and concentrated under reduced pressure. The residue was purified by column chromatography on silica gel using a mixture of cyclohexane and ethyl acetate (3:1) as eluant to give 1.24 g of the title compound having the following physical characteristic:

TLC (benzene:ethyl acetate=2:1): Rf=0.43.

REFERENCE EXAMPLE 33

6-Syn-methoxymethyl-7-anti-benzoyloxy-cis-bicyclo[3,3,0]octan-3-ol

To a solution of 124 g of the ketone compound (prepared as described in Reference Example 32) in 30 ml of methanol was added 290 mg of sodium borohydride in five portions at −10° C., and the mixture was stirred at the same temperature for 15 minutes. 1 ml of glacial acetic acid was added and the reaction mixture was then concentrated under reduced pressure. The residue was dissolved in ethyl acetate, washed with a saturated aqueous solution of sodium chloride, dried over anhydrous magnesium sulphate and concentrated under reduced pressure to obtain 1.3 g of the title compound as a crude product having the following physical characteristics:

TLC (benzene:ethyl acetate=3:1): Rf=0.25 and 0.15.

REFERENCE EXAMPLE 34

3-Acetoxy-6-syn-methoxymethyl-7-anti-benzoyloxy-cis-bicyclo[3,3,0]octane

To a mixture of 1.3 g of the 3-ol compound (prepared as described in Reference Example 33), 25 ml of methylene chloride and 1.6 ml of pyridine, 0.47 ml of acetyl chloride was added at 0° C. and the mixture was stirred at the same temperature for 30 minutes. The solution obtained was mixed with 0.2 ml of ethanol, stirred for 10 minutes, and extracted with ethyl acetate. The extract was washed with 1N hydrochloric acid, water and a saturated aqueous solution of sodium chloride, dried over anhydrous magnesium sulphate and concentrated under reduced pressure to obtain 1.44 g of the title compound as crude product having the following physical characteristic:

TLC (benzene:ethyl acetate=2:1): Rf=0.52.

REFERENCE EXAMPLE 35

3-Acetoxy-6-syn-hydroxymethyl-7-anti-benzoyloxy-cis-bicyclo[3,3,0]octane 2.47 ml of boron tribromide was added dropwise to a solution of 1.44 g of the 6-methoxymethyl compound (prepared as described in Reference Example 34) in 22 ml of methylene chloride at −78° C., and the mixture was stirred at 0° C. for 40 minutes. To the reaction mixture, 30 ml of diethyl ether was added and the mixture was then poured into 100 ml of a saturated aqueous solution of sodium bicarbonate, cooling the mixture with an ice-bath. The solution obtained was extracted with ethyl acetate. The extract was dried over anhydrous magnesium sulphate and concentrated under reduced pressure. The residue was purified by column chromatography on silica gel using a mixture of cyclohexane and ethyl acetate (3:1) as eluant to give 1.04 g of the title compound having the following physical characteristics:

TLC (benzene:ethyl acetate=2:1): Rf=0.26.
IR: $\nu$=3450, 1740, 1720, 1600, 1280, 1260, 1120, 720 cm$^{-1}$.
NMR: $\delta$=8.0–7.20 (5H,m), 5.20 (2H,m), 3.67 (2H,m), 2.03 (3H,s).

REFERENCE EXAMPLE 36

(E)-3-Acetoxy-6-syn-(3-oxooct-1-enyl)-7-anti-benzoyloxy-cis-bicyclo[3,3,0]octane 2.9 g of chromium trioxide was added to a solution of 4.7 ml of pyridine in 80 ml of methylene chloride at room temperature and the mixture was stirred for 15 minutes. To the solution obtained, 14 g of infusorial earth was added and a solution of 970 mg of the 6-hydroxymethyl compound (prepared as described in Reference Example 35) in 10 ml of methylene chloride were added successively at 0° C. and the mixture was stirred for 20 minutes. After stirring with 4 ml of allyl alcohol for 10 minutes, the reaction mixture was mixed with 22 g of sodium bisulphate and stirred at 0° C. for 10 minutes. The reaction mixture was filtered through a layer of anhydrous magnesium sulphate and the filtrate was concentrated at a temperature below 0° C. under reduced pressure to obtain the corresponding 6-formyl compound having the following Rf value:

TLC (benzene:ethyl acetate=2:1): Rf=0.54.

1.15 g of dimethyl 2-oxoheptylphosphonate

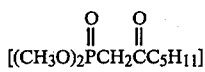

was added dropwise to a suspension of 153 mg of sodium hydride (content 63.5% w/w) in tetrahydrofuran and the mixture was stirred at room temperature for 30 minutes. To the solution obtained, the 6-formyl compound (prepared as described above) in 6 ml of tetrahydrofuran was added dropwise and the mixture was stirred at room temperature for 1 hour. The reaction mixture was mixed with 1 ml of glacial acetic acid, filtered through a layer of silica gel and the filtrate was concentrated under reduced pressure. The residue obtained was purified by column chromatography on silica gel using a mixture of cyclohexane and ethyl acetate (4:1) as eluant to give 960 mg of the title compound having the following physical characteristics:

TLC (benzene:ethyl acetate=2:1): Rf=0.65.
IR: $\nu$=1740, 1720, 1670, 1630, 1600, 1280, 1250, 720 cm$^{-1}$.
NMR: $\delta$=7.90–7.30 (5H,m), 6.65 (1H,dd), 6.0 (1H,d), 5.15 (2H,m), 2.01 (3H,s), 0.85 (3H,m).

Proceeding as described above, the following compounds having the physical characteristics given below were obtained from the 6-formyl compound, prepared as described above, and the appropriate phosphonate.

(a)

(E)-3-Acetoxy-6-syn-(3-oxo-4S-methyloct-1-enyl)-7-anti-benzoyloxy-cis-bicyclo[3,3,0]octane TLC (benzene:ethyl acetate=2:1): Rf=0.67.
IR: $\nu$=1740, 1720, 1670, 1630, 1600 cm$^{-1}$.
NMR: $\delta$=8.0–7.5 (5H,m), 6.65 (1H,d), 6.18 (1H,d), 5.13 (2H,m), 2.01 (3H,s), 1.0–0.7 (6H,m).

(b)

(E)-3-Acetoxy-6-syn-[3-oxo-3-(3-propylcyclopentyl)-prop-1-enyl]-7-anti-benzoyloxy-cis-bicyclo[3,3,0]octane TLC (benzene:ethyl acetate=2:1): Rf=0.68.
IR: $\nu$=1740, 1720, 1670, 1635, 1600 cm$^{-1}$.
NMR: $\delta$=8.0–7.5 (5H,m), 6.5 (1H,dd), 6.1 (1H,d), 5.10 (2H,m), 2.00 (3H,s), 0.86 (3H,m).

REFERENCE EXAMPLE 37

(E)-3-Acetoxy-6-syn-(3α$\beta$-hydroxyoct-1-enyl)-7-anti-benzoyloxy-cis-bicyclo[3,3,0]octane To a solution of 1.09 g of the 3-oxo compound (prepared as described in Reference Example 36) in 20 ml of methanol was added 380 mg of sodium borohydride and the mixture was stirred at −40° to −25° C. for 1 hour 20 minutes. 1 drop of glacial acetic acid was added to the reaction mixture which was then stirred at −40° C. for 30 minutes. The reaction mixture was then treated with 1.5 ml of glacial acetic acid and concentrated under reduced pressure. The residue was dissolved in ethyl acetate, washed with water and a saturated aqueous solution of sodium chloride, dried over anhydrous magnesium sulphate and concentrated under reduced pressure to give 1.03 g of the title compound having the following physical characteristics:

TLC (benzene:ethyl acetate=2:1): Rf=0.45 and 0.38.
IR: $\nu$=3450, 1740, 1720, 1600, 1450, 1280, 1250, 975 cm$^{-1}$.
NMR: $\delta$=8.00–7.10 (5H,m), 5.50 (2H,m), 5.30–4.70 (2H,m), 4.00 (1H,m), 2.02 (3H,s), 0.85 (3H,m).

Proceeding as described above, the following compounds having the physical characteristics given below were obtained, from the corresponding 3-oxo compounds prepared as described in Reference Example 36(a) and 36(b), respectively.

(a)

(E)-3-Acetoxy-6-syn-(3α$\beta$-hydroxy-4S-methyloct-1-enyl)-7-anti-benzoyloxy-cis-bicycle[3,3,0]octane TLC (benzene:ethyl acetate=2:1): Rf=0.47 and 0.39.
IR: $\nu$=3450, 1740, 1720, 1600 cm$^{-1}$.
NMR: $\delta$=8.00–7.15 (5H,m), 5.5 (2H,m), 5.3–4.7 (2H,m), 4.05 (1H,m), 2.01 (3H,s), 1.5–0.75 (6H,m).

(b)

(E)-3-Acetoxy-6-syn[3α$\beta$-hydroxy-3-(3-propylcyclopentyl)prop-1-enyl]-7-anti-benzoyloxy-cis-bicyclo[3,3,0]octane TLC (benzene:ethyl acetate=2:1): Rf=0.49 and 0.40.
IR: $\nu$=3450, 1740, 1720, 1600 cm$^{-1}$.
NMR: $\delta$=8.05–7.10 (5H,m), 5.5 (2H,m), 5.2–4.6 (1H,m), 4.02 (1H, m), 2.01 (3H,s), 0.85 (3H,m).

REFERENCE EXAMPLE 38

(E)-6-Syn-[3α$\beta$-(tetrahydropyran-2-yloxy)oct-1-enyl]-7-anti-benzoyloxy-cis-bicyclo[3,3,0]octan-3-ol To a solution of 1.02 g of the 3-hydroxy compound (prepared as described in Reference Example 37) in 20 ml of methylene chloride, 0.4 ml of 2,3-dihydropyran and approximately 3 mg of p-toluenesulphonic acid were added and the mixture was stirred at room temperature for 30 minutes. The reaction mixture was mixed with 1 ml of triethylamine and concentrated under reduced pressure to obtain 1.25 g of (E)-3-acetoxy-6-syn-[3α$\beta$-(tetrahydropyran-2-yloxy)oct-1-enyl]-7-anti-benzoyloxy-cis-bicyclo[3,3,0]octane as a crude compound having the following Rf value:

TLC (benzene:ethyl acetate=2:1): Rf=0.60.

The compound thus obtained was dissolved in 20 ml of methanol. To the solution, 220 mg of potassium carbonate was added at 0° C., and the mixture was stirred at the same temperature for 4 hours. The reaction mixture was mixed with 1 ml of glacial acetic acid and concentrated under reduced pressure. The residue was dissolved in ethyl acetate, washed with water and a saturated aqueous solution of sodium chloride, dried over anhydrous magnesium sulphate and concentrated under reduced pressure. The residue was purified by column chromatography on silica gel using a mixture of cyclohexane and ethyl acetate (2:1) as eluant to give 938 mg of the title compound having the following physical characteristics:

TLC (benzene:ethyl acetate=2:1): Rf=0.46, 0.40, 0.36 and 0.30.

IR: $\nu=3450, 1720, 1600, 1450, 1280, 1025, 980, 720$ cm$^{-1}$.

NMR: $\delta=8.00-7.20$ (5H,m), 5.70-5.25 (2H,m), 5.20-4.80 (1H,m), 4.60 (1H,m), 4.50-4.15 (1H,m), 0.85 (3H,m).

Proceeding as described above the following compounds, having the physical characteristics given below, were prepared from the corresponding 3-hydroxy compounds described in Reference Example 37(a) and 37(b):

(a-i)

(E)-3-Acetoxy-6-syn-[3α$\beta$-(tetrahydropyran-2-yloxy)-4S-methyloct-1-enyl]-7-anti-benzoyloxy-cis-bicyclo[3,3,0]octane TLC (benzene:ethyl acetate=2:1): Rf=0.61.

(a-ii)

(E)-6-Syn-[3α$\beta$-(tetrahydropyran-2-yloxy)-4S-methyloct-1-enyl]-7-anti-benzoyloxy-cis-bicyclo[3,3,0]octan-3-ol TLC (benzene:ethyl acetate=2:1): Rf=0.47, 0.41, 0.37 and 0.32.

IR: $\nu=3450, 1720, 1600, 980$ cm$^{-1}$.

NMR: $\delta=8.0-7.2$ (5H,m), 5.7-5.2 (2H,m), 5.2-4.7 (1H,m), 4.6 (1H, m), 4.6-4.1 (1H,m), 1.1-0.7 (6H,m).

(b-i)

(E)-3-Acetoxy-6-syn-[3α$\beta$-(tetrahydropyran-2-yloxy)-3-(3-propylcyclopentyl)prop-1-enyl]-7-anti-benzoyloxy-cis-bicyclo[3,3,0]octane TLC (benzene:ethyl acetate=2:1): Rf=0.63.

(b-ii)

(E)-6-syn-[3α$\beta$-(tetrahydropyran-2-yloxy)-3-(3-propylcyclopentyl)prop-1-enyl]-7-anti-benzoyloxy-cis-bicyclo[3,3,0]octan-3-ol TLC (benzene:ethyl acetate=2:1): Rf=0.49, 0.43, 0.38 and 0.33.

IR: $\nu=3450, 1720, 1600, 980$ cm$^{-1}$.

NMR:$\delta=8.0-7.1$ (5H,m), 5.75-5.2 (2H,m), 5.2-4.75 (1H,m), 4.62 (1H,m), 4.5-4.1 (1H,m), 0.86 (3H,m).

REFERENCE EXAMPLE 39

(E)-6-Syn-[3α$\beta$-(tetrahydropyran-2yloxy)oct-1-enyl]-7-anti-benzoyloxy-cis-bicyclo[3,3,0]octan-3-one 2.1 g of chromium trioxide was added to a solution of 3.4 ml of pyridine in 60 ml of methylene chloride at room temperature and the mixture was stirred for 15 minutes. To the solution obtained, 10 g of infusorial earth and a solution of 938 mg of the 3-hydroxy compound (prepared as described in Reference Example 38) in 5 ml of methylene chloride were added successively at 0° C. and the mixture was stirred for 20 minutes. After stirring with 2.9 ml of allyl alcohol for 10 minutes, the reaction mixture was mixed with 16 g of sodium bisulphate and stirred for 10 minutes. The reaction mixture was filtered through a layer of anhydrous magnesium sulphate, and the filtrate was concentrated under reduced pressure. The residue was purified by column chromatography on silica gel using a mixture of cyclohexane and ethyl acetate (5:1) as eluant to give 860 mg of the title compound having the following physical characteristics:

TLC (benzene:ethyl acetate=2:1): Rf=0.60 and 0.52.

IR: $\nu=1740, 1720, 1600, 1280, 1030, 980, 720$ cm$^{-1}$.

NMR: $\delta=8.00-7.20$ (5H,m), 5.70-4.90 (3H,m), 4.70-4.30 (1H,m), 0.85 (3H,m).

Proceeding as described above the following compounds, having the physical characteristics given below were prepared from the corresponding compounds described in Reference Example 38(a-ii) and 38(b-ii):

(a)

(E)-6-Syn-[3α$\beta$-(tetrahydropyran-2-yloxy)-4S-methyloct-1-enyl]-7-anti-benzoyloxy-cis-bicyclo[3,3,0]octan-3-one TLC (benzene:ethyl acetate=2:1): Rf=0.63 and 0.55.

IR: $\nu=1740, 1720, 1600, 980$ cm$^{-1}$.

NMR: $\delta=8.1-7.1$ (5H,m), 5.7-4.2 (4H,m), 1.0-0.7 (6H,m).

(b)

(E)-6-Syn-[3α$\beta$-(tetrahydropyran-2-yloxy)-3-(3-propylcyclopentyl)prop-1-enyl]-7-anti-benzoyloxy-cis-bicyclo[3,3,0]octan-3-one TLC (benzene:ethyl acetate=2:1): Rf=0.65 and 0.54.

IR: $\nu=1740, 1720, 1600, 980$ cm$^{-1}$.

NMR: $\delta=8.1-7.2$ (5H,m), 5.7-4.2 (4H,m), 0.86 (3H,m).

REFERENCE EXAMPLE 40

(E)-6-Syn-[3α$\beta$-tetrahydropyran-2-yloxy)oct-1-enyl]-7-anti-hydroxy-cis-bicyclo[3,3,0]octan-3-one A mixture of a solution of 860 mg of the 7-benzyloxy compound (prepared as described in Reference Example 39) in 15 ml of methanol and 410 mg of potassium carbonate was stirred at 40°-45° C. for 1.5 hours and then for a further 16 hours at room temperature. The reaction mixture was mixed with 0.6 ml of glacial acetic acid and concentrated under reduced pressure. The residue was dissolved in ethyl acetate, washed with water and a saturated aqueous solution of sodium chloride, dried over anhydrous magnesium sulphate and concentrated under reduced pressure. The residue was purified by column chromatography on silica gel using a mixture of cyclohexane and ethyl acetate (1:1) as eluant to give 407 mg of the title compound having the following physical characteristics:

TLC (benzene:ethyl acetate=2:1): Rf=0.17 and 0.15.

IR: $\nu=3430, 1740, 1020, 980$ cm$^{-1}$.

NMR: $\delta=5.40$ (2H,m), 4.65 (1H,m), 4.20-3.20 (4H,m), 0.85 (3H,m).

Proceeding as described above the following compounds, having the physical characteristics given below, were prepared from the corresponding compounds described in Reference Example 39(a) and 39(b):

(a)

(E)-6-Syn-[3α$\beta$-(tetrahydropyran-2-yloxy)-4S-methyloct-1-enyl]-7-anti-hydroxy-cis-bicyclo[3,3,0]octan-3-one TLC (benzene:ethyl acetate=2:1): Rf=0.18 and 0.16;
IR: $\nu=3450, 1740, 980$ cm$^{-1}$;

NMR: δ=5.7-5.2 (2H,m), 4.65 (1H,m), 4.3-3.1 (4H,m), 1.0-0.7 (6H,m).

(b)

(E)-6-Syn-[3αβ-(tetrahydropyran-2-yloxy)-3-(3-propyl-cyclopentyl)prop-1-enyl]-7-anti-hydroxy-cis-biscyclo[3,3,0]octan-3-one TLC (benzene:ethyl acetate=2:1): Rf=0.19 and 0.17.
IR: ν=3450, 1740, 980 cm⁻¹.
NMR: δ=5.7-5.2 (2H,m), 4.65 (1H,m), 4.3-3.1 (4H,m), 0.86 (3H,m).

REFERENCE EXAMPLE 41

(E)-6-Syn-[3αβ-(tetrahydropyran-2-yloxy)oct-1-enyl]-7-anti-(tetrahydropyran-2-yloxy)-cis-bicyclo[3,3,0]-octan-3-one 0.3 ml of 2,3-dihydropyran and approximately 2 mg of p-toluenesulphonic acid were added to a solution of 407 mg of the 7-hydroxy compound (prepared as described in Reference Example 40) in 9 ml of methylene chloride and the mixture was stirred at room temperature for 30 minutes. The reaction mixture was mixed with 0.5 ml of triethylamine and concentrated under reduced pressure. The residue was purified by column chromatography on silica gel using a mixture of cyclohexane and ethyl acetate (5:1) as eluant to give 488 mg of the title compound having the following physical characteristics:

TLC (benzene:ethyl acetate=2:1): Rf=0.44.
IR: ν=1740, 1130, 1030, 980 cm⁻¹.
NMR: δ=5.70-5.25 (2H,m), 4.65 (2H,m), 4.15-3.15 (6H,m), 0.85 (3H,m).

Proceeding as described above the following compounds, having the physical characteristics given below were prepared from the corresponding compounds described in Reference Example 40(a) and 40(b):

(a)

(E)-6-Syn-[3αβ-(tetrahydropyran-2-yloxy)-4S-methyloct-1-enyl]-7-anti-(tetrahydropyran-2yloxy)-cis-bicyclo[3,3,0]octan-3-one TLC (benzene:ethyl acetate=2:1): Rf=0.46.
IR: ν=1740, 980 cm¹.
NMR: δ=5.7-5.2 (2H,m), 4.65 (2H,m), 4.2-3.1 (6H,m), 1.0-0.7 (6H,m).

(b)

(E)-6-Syn-[3αβ-(tetrahydropyran-2-yloxy)-3-(3-propyl-cyclopentyl)prop-1-enyl]-7-anti-(tetrahydropyran-2-yloxy)-cis-bicyclo[3,3,0]octan-3-one TLC (benzene:ethyl acetate=2:1): Rf=0.49.
IR: ν=1740, 980 cm⁻¹.
NMR: δ=5.7-5.2 (2H,m), 4.65 (2H,m), 4.2-3.1 (6H,m), 0.86 (3H,m).

EXAMPLE 5

(5EZ,13E)-(9α,11β,15αβ)-6,9-Methano-11,15-bis(tetrahydropyran-2-yloxy)prosta-5,13-dienoic acid methyl ester A mixture of 155 mg of sodium hydride (content 63.5% w/w) and 2.1 ml of dimethyl sulphoxide was stirred at 65°-70° C. for 1 hour. The solution thus obtained was added dropwise to a solution of 886 mg of (4-carboxybutyl)triphenylphosphonium bromide in 2 ml of dimethyl sulphoxide, cooling the mixture with an ice-bath. To the solution obtained was added dropwise 350 mg of the 3-oxo compound (prepared as described in Reference Example 41) in 2 ml of dimethyl sulphoxide, and the mixture was stirred at 30°-35° C. for 15 hours. The reaction mixture was mixed with 35 ml of ice-water, acidified to pH 4 with an aqueous solution of oxalic acid and extracted with a mixture of diethyl ether and ethyl acetate (1:1). The extract was washed with water, a saturated aqueous solution of sodium chloride, dried over anhydrous magnesium sulphate, and concentrated under reduced pressure to give (5EZ,13E)-(9α,11β,15αβ)-6,9-methano-11,15-bis(tetrahydropyran-2-yloxy)prosta-5,13-dienoic acid as a crude product having the following Rf value:

TLC (benzene:ethyl acetate=2:1): Rf=0.32 and 0.26.

The acid compound, thus obtained, was dissolved in 20 ml of ethyl acetate and diazomethane-etherate was added to the solution, cooling the mixture with an ice-bath until the pale-yellow colour did not vanish and the reaction mixture was then concentrated under reduced pressure. The residue was purified by column chromatography on silica gel using a mixture of cyclohexane and ethyl acetate (7:1) as eluant to give 330 mg of the title compound having the following physical characteristics:

TLC (benzene:ethyl acetate=4:1): Rf=0.55.
IR: ν=1740, 1440, 1025, 980 cm⁻¹.
NMR: δ=5.60-5.00 (3H,m), 4.65 (2H,m), 4.15-3.20 (6H,m), 3.60 (3H,s), 0.85 (3H,m).

Proceeding as described above, the following compounds, having the physical characteristics given below, were prepared from the corresponding 3-oxo compounds described in Reference Example 41(a) and 41(b):

(a-i)

(5EZ,13E)-(9α,11α,15αβ,16S)-6,9-Methano-11,15-bis(-tetrahydropyran-2-yloxy)-16-methylprosta-5,13-dienoic acid TLC (benzene:ethyl acetate=2:1): Rf=0.33 and 0.28.

(a-ii)

(5EZ,13E)-(9α,11α,15αβ,16S)-6,9-Methano-11,15-bis(-tetrahydropyran-2-yloxy)-16-methylprosta-5,13-dienoic acid methyl ester TLC (benzene:ethyl acetate=4:1): Rf=0.57.
IR: ν=1740, 980 cm⁻¹.
NMR: δ=5.7-5.0 (3H,m), 4.65 (2H,m), 4.2-3.2 (6H,m), 1.0-0.7 (6H,m).

(b-i)

(5EZ,13E)-(9α,11α,15αβ)-6,9-Methano-11,15-bis(tetrahydropyran-2-yloxy)-15-(3-propylcyclopentyl)-16,17,18,19,20-pentanorprosta-5,13-dienoic acid TLC (benzene:ethyl acetate=2:1): Rf=0.32 and 0.27.

(b-ii)

(5EZ,13E)-(9α,11α,15αβ)-6,9-Methano-11,15-bis(tetrahydropyran-2-yloxy)-15-(3-propylcyclopentyl)-16,17,18,19,20-pentanorprosta-5,13-dienoic acid methyl ester TLC (benzene:ethyl acetate=4:1): Rf=0.58;
IR: ν=1740, 980 cm⁻¹;
NMR: 67 =5.7-5.0 (3H,m), 4.65 (2H m), 4.2-3.1 (6H,m), 0.86 (3H,m).

EXAMPLE 6

(5EZ,13E)-(9α,11α,15α)-6,9-Methano-11,15-dihydroxyprosta-5,13-dienoic acid methyl ester and 15β-isomer thereof A mixture of a solution of 330 mg of the bis(tetrahydropyran-2-yloxy) compound (prepared as described in Example 5) in 6 ml of methanol and approximately 5 mg of p-toluenesulphonic acid was stirred at room temperature for 2 hours. The reaction mixture was mixed with 1 ml of triethylamine and then concentrated under reduced pressure. The residue was purified by column chromatography on silica gel using a mixture of cyclohexane and ethyl acetate (3:1) as eluant to give 115 mg of the title compound (15α-compound) and 72 mg of the 15β-isomer. The 15α-compound had the same physical characteristics as the compound prepared as described in Example 3(h). The 15β-compound had the following physical characteristics:

TLC (benzene:ethyl acetate=2:1): Rf=0.35;
IR: $\nu=3360, 1740, 1440, 1170, 975$ cm$^{-1}$;
NMR: $\delta=5.59$ (2H,m), 5.24 (1H,m), 4.10 (1H,m), 3.90–3.55 (1H,m), 3.67 (3H,s), 0.90 (3H,m).

Proceeding as described above, the following compounds were prepared from the corresponding bis(tetrahydropyran-2-yloxy) compounds described in Example 5(a) and 5(b):

(5EZ,13E)-(9α,11α,15α,16S)-6,9-Methano-11,15-dihydroxy-16-methylprosta-5,13-dienoic acid methyl ester and its 15β-isomer The 15α-compound had the same physical characteristics as the compound prepared as described in Example 3(d).

The 15β-compound had the following physical characteristics:

TLC (benzene:ethyl acetate=2:1) Rf=0.37.
IR: $\nu=3360, 1740, 980$ cm$^{-1}$.
NMR: $\delta=5.7-5.0$ (3H,m), 4.3–4.0 (1H,m), 3.9–3.5 (1H,m), 3.68 (3H,s), 1.1–0.7 (6H,m).

(b)

(5EZ,13E)-(9α,11α,15α)-6,9-Methano-11,15-dihydroxy-15-(3-propylcyclopentyl)-16,17,18,19,20-pentanorprosta-5,13-dienoic acid methyl ester and its 15β-isomer The 15α-compound had the same physical characteristics as the compound prepared as described in Example 3(e).

The 15β-compound had the following physical characteristics:

TLC (benzene:ethyl acetate=2:1): Rf=0.39.
IR: $\nu=3360, 1740, 980$ cm$^{-1}$.
NMR: $\delta=5.7-5.0$ (3H,m), 4.3–4.0 (1H,m), 3.9–3.5 (1H,m), 3.68 (3H,s), 1.0–0.80 (3H,m).

The present invention includes within its scope pharmaceutical compositions which comprise at least one new therapeutically useful compound of general formula II wherein $R^2$ and $R^3$ both represent hydogen atoms and the other symbols are as hereinbefore defined, or cyclodextrin clathrate of such acids and esters or, when $R^1$ represents a hydrogen atom, non-toxic salt thereof or, when $R^1$ represents a group

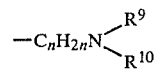

in which n, $R^9$ and $R^{10}$ are as hereinbefore defined, non-toxic acid addition salt thereof, together with a pharmaceutical carrier or coating. In clinical practice the new compounds of the present invention of general formula II wherein $R^2$ and $R^3$ both represent hydrogen atoms will normally be administered orally, vaginally, rectally or parenterally.

Solid compositions for oral administration include compressed tablets, pills, dispersible powders and granules. In such solid compositions one or more of the active compounds is, or are, admixed with at least one inert diluent such as calcium carbonate, potato starch, alginic acid, lactose or mannitol. The compositions may also comprise, as is normal practice, additional substances other than inert diluents, e.g. lubricating agents such as magnesium stearate. Liquid compositions for oral administration include pharmaceutically-acceptable emulsions, solutions, suspensions, syrups and elixirs containing inert diluent commonly used in the art, such as water and liquid paraffin. Besides inert diluents such compositions may also comprise adjuvants such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds of general formula II wherein $R^2$ and $R^3$ both represent hydrogen atoms.

Solid compositions for rectal administration include suppositories formulated in manner known per se and containing one or more of the active compounds of general formula II wherein $R^2$ and $R^3$ both represent hydrogen atoms.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, each dose per person is generally between 0.05 and 500 μg by parenteral administration in the treatment of hypertension or disorders of the peripheral circulation, and between 0.05 and 500 μg by parenteral administration in the prevention and treatment of cerebral thrombosis, myocardial infarction and arteriosclerosis.

The following Example illustrates pharmaceutical compositions according to the invention.

EXAMPLE 7

(5EZ,13E)-(9α,11α,15α,17S)-6,9-methano-11,15-dihydroxy-17,20-dimethylprosta-5,13-dienoic acid (500 μg) was dissolved in ethanol (5 ml). The solution was then sterilised by passage through a bacteria-retaining filter and placed in 0.1 ml portions in 1 ml ampoules, to give 10 μg of (5EZ,13E)-(9α,11α,15α,17S)-6,9-methano-11,15-dihydroxy-17,20-dimethylprosta-5,13-dienoic acid per ampoule. The ampoules were sealed. The contents of an ampoule diluted to a suitable volume, e.g. with 1 ml of tris-HCl-buffer solution (pH 8.6), gave a solution ready for administration by injection.

We claim:

1. A prostaglandin I$_2$ analogue of the formula:

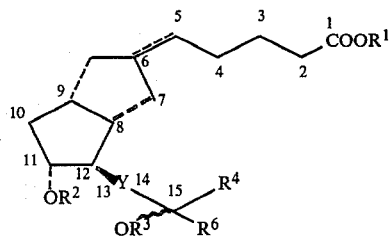

II wherein the symbol ==== between the carbon atoms in positions 5 and 6 represents a single or double bond, Y represents ethylene or trans-vinylene, R$^1$ represents a hydrogen atom, a straight- or branched-chain alkyl group containing from 1 to 12 carbon atoms, ar aralkyl group containing from 7 to 12 carbon atoms, a cycloalkyl group containing from 4 to 7 carbon atoms unsubstituted or substituted by at least one straight- or branched-chain alkyl group containing from 1 to 4 carbon atoms, a phenyl group unsubstituted or substituted by at least one chlorine atom, trifluoromethyl group, alkyl group containing from 1 to 4 carbon atoms or phenyl group, a —C$_m$H$_{2m}$COOR$^7$ group, wherein m represents an integer of from 1 to 12 and R$^7$ represents a straight- or branched-chain alkyl group containing from 1 to 4 carbon atoms, a —C$_n$H$_{2n}$OR$^8$ group, wherein n represents an integer of from 2 to 12 and R$^8$ represents a hydrogen atom or a straight- or branched-chain alkyl group containing from 1 to 4 carbon atoms, or a

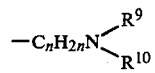

group, wherein R$^9$ and R$^{10}$, which may be the same or different, each represents a straight- or branched-chain alkyl group containing from 1 to 4 carbon atoms and n is as hereinbefore defined, R$^2$ represents a hydrogen atom or a hydroxy-protecting group which is eliminated under acidic or alkaline conditions selected from the group consisting of tetrahydropyran-2-yl, tetrahydrofuran-2-yl, tetrahydrothiopyran-2-yl, 1-ethoxyethyl, (1-methoxy-1-methyl)ethyl, 1-methoxycyclohexyl, (1-methoxy-1-phenyl)ethyl, trimethylsilyl, triethylsilyl, tri-n-butylsilyl, tert-butyldimethylsilyl, tribenzylsilyl, triphenylsilyl, acetyl, chloroacetyl, dichloroacetyl, trichloroacetyl, trifluoroacetyl, propionyl, benzoyl, p-phenylbenzoyl, and naphthyloyl, R$^3$ represents a hydrogen atom or a hydroxy-protecting group which is eliminated under acidic conditions selected from the group consisting of tetrahydropyran-2-yl, tetrahydrofuran-2-yl, tetrahydrothiopyran-2-yl, 1-ethoxyethyl, (1-methoxy-1-methyl)ethyl, 1-methoxy-cyclohexyl, (1-methoxy-1-phenyl)ethyl, trimethylsilyl, triethylsilyl, tri-n-butylsilyl, tert-butyldimethylsilyl, tribenzylsilyl, and triphenylsilyl, R$^4$ represents a hydrogen atom or a methyl or ethyl group, R$^6$ represents a cycloalkyl group containing from 4 to 7 carbon atoms unsubstituted or substituted by at least one straight- or branched-chain alkyl group containing from 1 to 8 carbon atoms, the wavy line ⁓⁓ attached to the carbon in position 15 represents α- or β-configuration or a mixture thereof and when ==== represents a double bond, the double bond between C$_5$–C$_6$ is E, Z or a mixture thereof, and when ==== represents a single bond, the absolute configuration of C$_6$ is R, S or a mixture thereof and, when R$^2$ and R$^3$ represent hydrogen atoms, cyclodextrin clathrates of such acids and esters and, when R$^1$, R$^2$ and R$^3$ represent hydrogen atoms non-toxic salts thereof and, when R$^1$ represents a

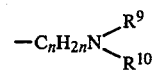

group in which n, R$^9$ and R$^{10}$ are as hereinbefore defined, non-toxic acid addition salts thereof.

2. A compound of the general formula:

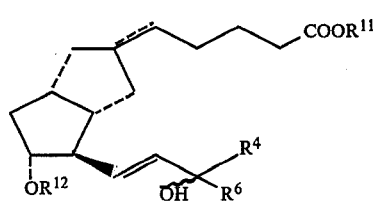

IVA wherein R$^{11}$ represents a straight- or branched-chain alkyl group containing from 1 to 12 carbon atoms, R$^{12}$ represents a hydroxy-protecting group which is eliminated under acidic conditions selected from the group consisting of tetrahydropyran-2-yl, tetrahydrofuran-2-yl, tetrahydrothiopyran-2-yl, 1-ethoxyethyl, (1-methoxy-1-methyl)ethyl, 1-methoxy-cyclohexyl, (1-methoxy-1-phenyl)ethyl, trimethylsilyl, triethylsilyl, tri-n-butylsilyl, tert-butyldimethylsilyl, tribenzylsilyl and triphenylsilyl and the other symbols are as defined in claim 1.

3. A compound of the general formula:

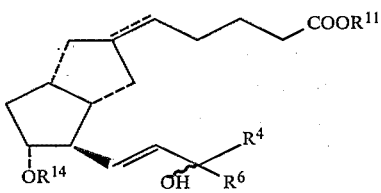

wherein R¹⁴ represents a hydroxy-protecting group which is eliminated under alkaline conditions selected from the group consisting of acetyl, chloroacetyl, dichloroacetyl, trichloroacetyl, trifluoroacetyl, propionyl, benzoyl, p-phenylbenzoyl, and naphthyloyl, R¹¹ is as defined in claim 2 and the other symbols are as defined in claim 1.

4. A prostaglandin analogue according to claim 1 wherein R² and R³ both represent hydrogen atoms.

5. A prostaglandin analogue according to claim 1 wherein R¹ represents a hydrogen atom or a straight- or branched-chain alkyl group containing from 1 or 4 carbon atoms.

6. A prostaglandin analogue according to claim 1 wherein R¹ represents a hydrogen atom or a methyl group.

7. A prostaglandin analogue according to claim 1 wherein the symbol ===== between the carbon atoms in positions 5 and 6 represents a double bond.

8. A prostaglandin analogue according to claim 1 wherein Y represents trans-vinylene.

9. A prostaglandin analogue according to claim 1 wherein the grouping —R⁶ represents a cyclobutyl, cyclopentyl or cyclohexyl group unsubstituted or substituted by a methyl, ethyl or propyl group.

10. A prostaglandin analogue according to claim 1 wherein the grouping —R⁶ represents 3-ethylcyclobutyl, cyclopentyl, 3-ethylcyclopentyl, 3-propylcyclopentyl, cyclohexyl, or 4-methylcyclohexyl.

11. A prostaglandin analogue according to claim 1 wherein the hydroxy group or protected-hydroxy group attached to the C-15 carbon atom in formula II is in α-configuration.

12. A prostaglandin analogue according to claim 1 which is (5EZ,13E)-(9α,11α,15α)-6,9-methano-11,15-dihydroxy-15-(3-ethylcyclobutyl)-16,17,18,19,20-pentanorprosta-5,13-dienoic acid methyl ester and cyclodextrin clathrates thereof.

13. A prostaglandin analogue according to claim 1 which is (5EZ,13E)-(9α,11α,15α)-6,9-methano-11,15-dihydroxy-15-(4-methylcyclohexyl)-16,17,18,19,20-pentanorprosta-5,13-dienoic acid methyl ester and cyclodextrin clathrates thereof.

14. A prostaglandin analogue according to claim 1 which is (5EZ,13E)-(9α,11α,15α)-6,9-methano-11,15-dihydroxy-15-cyclopentyl-16,17,18,19,20-pentanorprosta-5,13-dienoic acid methyl ester and cyclodextrin clathrates thereof.

15. A prostaglandin analogue according to claim 1 which is (5EZ,13E)-(9α,11α,15α)-6,9-methano-11,15-dihydroxy-15-(3-ethylcyclopentyl)-16,17,18,19,20-pentanorprosta-5,13-dienoic acid methyl ester and cyclodextrin clathrates thereof.

16. A prostaglandin analogue according to claim 1 which is (5EZ,13E)-(9α,11α,15α)-6,9-methano-11,15-dihydroxy-15-cyclohexyl-16,17,18,19,20-pentanorprosta-5,13-dienoic acid methyl ester and cyclodextrin clathrates thereof.

17. A prostaglandin analogue according to claim 1 which is (5EZ,13E)-(9α,11α,15α)-6,9-methano-11,15-dihydroxy-15-(3-propylcyclopentyl)-16,17,18,19,20-pentanorprosta-5,13-dienoic acid methyl ester and cyclodextrin clathrates thereof.

18. A prostaglandin analogue according to claim 1 which is (5EZ,13E)-(9α,11α,15α)-6,9-methano-11,15-dihydroxy-15-(3-propylcyclopentyl)-16,17,18,19,20-pentanorprosta-5,13-dienoic acid and cyclodextrin clathrates and non-toxic salts thereof.

19. A prostaglandin analogue according to claim 1 which is (5EZ,13E)-(9α,11α,15α)-6,9-methano-11,15-dihydroxy-15-cyclohexyl-16,17,18,19,20-pentanorprosta-5,13-dienoic acid and cyclodextrin clathrates and non-toxic salts thereof.

20. A prostaglandin analogue according to claim 1 which is (5EZ,13E)-(9α,11α,15α)-6,9-methano-11,15-dihydroxy-15-(3-ethylcyclopentyl)-16,17,18,19,20-pentanorprosta-5,13-dienoic acid and cyclodextrin clathrates and non-toxic salts thereof.

21. A prostaglandin analogue according to claim 1 which is (5EZ,13E)-(9α,11α,15α)-6,9-methano-11,15-dihydroxy-15-(3-ethylcyclobutyl)-16,17,18,19,20-pentanorprosta-5,13-dienoic acid and cyclodextrin clathrates and non-toxic salts thereof.

22. A prostaglandin analogue according to claim 1 which is (5EZ,13E)-(9α,11α,15α)-6,9-methano-11,15-dihydroxy-15-(4-methylcyclohexyl)-16,17,18,19,20-pentanorprosta-5,13-dienoic acid and cyclodextrin clathrates and non-toxic salts thereof.

23. A prostaglandin analogue according to claim 1 which is (5EZ,13E)-(9α,11α,15α)-6,9-methano-11,15-dihydroxy-15-cyclopentyl-16,17,18,19,20-pentanorprosta-5,13-dienoic acid and cyclodextrin clathrates and non-toxic salts thereof.

24. A compound according to claim 2 which is (5EZ,13E)-(9α,11α,15αβ)-6,9-methano-11-(tetrahydropyran-2-yloxy)-15-hydroxy-15-(3-ethylcyclopentyl)-16,17,18,19,20-pentanorprosta-5,13-dienoic acid methyl ester.

25. A compound according to claim 2 which is (5EZ,13E)-(9α,11α,15αβ)-6,9-methano-11-(tetrahydropyran-2-yloxy)-15-hydroxy-15-cyclohexyl-16,17,18,19,20-pentanorprosta-5,13-dienoic acid methyl ester.

26. A compound according to claim 2 which is (5EZ,13E)-(9α,11α,15αβ)-6,9-methano-11-(tetrahydropyran-2-yloxy)-15-hydroxy-15-(3-propylcyclopentyl)-16,17,18,19,20-pentanorprosta-5,13-dienoic acid methyl ester.

27. A compound of the general formula:

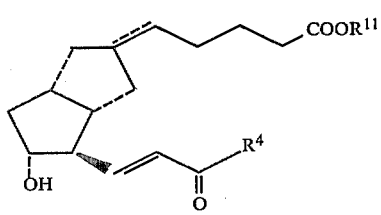

wherein R¹¹ is as defined in claim 2 and the other symbols are as defined in claim 1.

28. Pharmaceutical compositions useful in the treatment of hypertension, in the treatment of disorders of the peripheral circulation and in the prevention and treatment of cerebral thrombosis, myocardial infarction, and arteriosclerosis which comprise, as active ingredient, at least one prostaglandin analogue as claimed in claim 1, wherein $R^2$ and $R^3$ both represent hydrogen atoms, or cyclodextrin clathrate thereof or, when $R^1$, $R^2$ and $R^3$ represent hydrogen atoms, non-toxic salt thereof, or when $R^1$ represents a

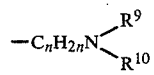

group in which n, $R^9$ and $R^{10}$ are as defined in claim 1 and $R^2$ and $R^3$ represent hydrogen atoms, non-toxic acid addition salt thereof, in association with a pharmaceutically acceptable diluent or carrier.

29. Pharmaceutical compositions according to claim 28 which comprise, as active ingredient, at least one prostaglandin analogue as claimed in any one of claims 12 to 15, 16, 18, 19 and 20 to 23, or cyclodextrin clathrate thereof, or non-toxic salt of a prostaglandin analogue as claimed in any one of claims 18, 19 and 20 to 23.

30. A prostaglandin analogue according to claim 1 which is a cyclodextrin clathrate of a prostaglandin analogue as claimed in any one of claims 4 to 11 wherein $R^2$ and $R^3$ both represent hydrogen atoms.

31. A prostaglandin analogue according to claim 1 which is a non-toxic salt of a prostaglandin analogue as claimed in any one of claims 4 to 11 wherein the symbols $R^1$, $R^2$ and $R^3$ represent hydrogen atoms.

32. A prostaglandin analogue according to claim 1 which is a non-toxic acid addition salt of a prostaglandin analogue as claimed in any one of claims 1, 4 and 7 to 11 wherein $R^1$ represents a group

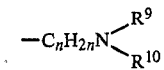

in which n, $R^9$ and $R^{10}$ are as defined in claim 1.

33. A compound of the general formula:

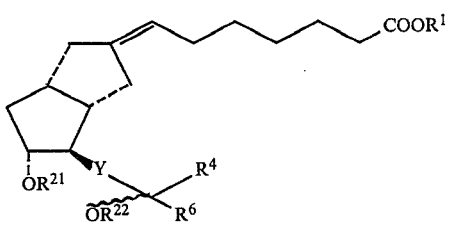

wherein $R^{21}$ and $R^{22}$ each represent a hydroxy-protecting group which is eliminated under acidic conditions selected from the group consisting of tetrahydropyran-2-yl, tetrahydrofuran-2-yl, tetrahydrothiopyran-2-yl, 1-ethoxyethyl, (1-methoxy-1-methyl)ethyl, 1-methoxy-cyclohexyl, (1-methoxy-1-phenyl)ethyl, trimethylsilyl, triethylsilyl, tri-n-butylsilyl, tert-butyldimethylsilyl, tribenzylsilyl, and triphenylsilyl and $R^{21}$ may also represent a hydrogen atom, and the other symbols are as defined in claim 1.

34. A prostaglandin analogue according to claim 1 wherein $R^2$ and $R^3$ both represent a hydroxy-protecting group which is eliminated under acidic conditions.

35. A prostaglandin analogue according to claim 1 wherein $R^2$ represents a hydroxy-protecting group which is eliminated under acidic conditions and $R^3$ represents a hydrogen atom.

36. A prostaglandin analogue according to claim 34 or 35 wherein the hydroxy-protecting group is a tetrahydropyran-2-yl, tetrahydrofuran-2-yl, tetrahydrothiopyran-2-yl, 1-ethoxyethyl, (1-methoxy-1-methyl)ethyl, 1-methoxy-cyclohexyl, (1-methoxy-1-phenyl)ethyl, trimethylsilyl, triethylsilyl, tri-n-butylsilyl, tert-butyldimethylsilyl, tribenzylsilyl or triphenylsilyl group.

37. A prostaglandin analogue according to claim 34 or 35 wherein the hydroxy-protecting group is the tetrahydropyran-2-yl group.

38. A compound according to claim 27 which is (5EZ,13E)-(9α,11α)-6,9-methano-11-hydroxy-15-oxo-15-(3-ethylcyclobutyl)-16,17,18,19,20-pentanorprosta-5,13-dienoic acid methyl ester.

39. A compound according to claim 27 which is (5EZ,13E)-(9α,11α)-6,9-methano-11-hydroxy-15-oxo-15-(4-methylcyclohexyl)-16,17,18,19,20-pentanorprosta-5,13-dienoic acid methyl ester.

40. A compound according to claim 27 which is (5EZ,13E)-(9α,11α)-6,9-methano-11-hydroxy-15-oxo-15-cyclopentyl-16,17,18,19,20-pentanorprosta-5-13-dienoic acid methyl ester.

* * * * *

UNITED STATES PATENT AND TRADEMARK OFFICE
CERTIFICATE OF CORRECTION

PATENT NO. : 4,479,966

DATED : Oct. 30, 1984

INVENTOR(S) : Hayashi et al.

It is certified that error appears in the above-identified patent and that said Letters Patent is hereby corrected as shown below:

In the title, front page and at column 1, change "PGI2" to -- $PGI_2$ --

In the ABSTRACT, lines 27 and 28, after "when" insert --  --

Column 3, line 27, after "at" insert -- the --

Column 5, line 14, change "2" to -- 1 --

Column 6, line 55, change the pertinent portion of the formula to read

-- 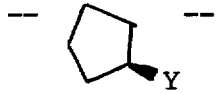 --

Column 11, line 52, change "phosphonate" to -- phosphorane --

Column 12, line 33, change "phosphoric acid, cya-" to -- phosphorous acid, cya- --

Column 14, line 58, change "ycyclohexane" to -- ycyclohexene --

Column 24, line 25, change the pertinent portion of the formula to read

--  --

Column 25, Scheme F, change the pertinent portion of the formula XLV to read

--  --

Column 29, line 17, change "XLVXII" to -- XLVIII --

Column 30, line 32, change "LXXI" to -- LXII --

UNITED STATES PATENT AND TRADEMARK OFFICE
CERTIFICATE OF CORRECTION

PATENT NO. : 4,479,966
DATED : Oct. 30, 1984
INVENTOR(S) : Hayashi et al.

It is certified that error appears in the above-identified patent and that said Letters Patent is hereby corrected as shown below:

Column 31, line 58, change "tetralkylam-" to -- tetraalkylam- --

Column 32, line 51, after "sent" insert -- hydrogen --

Column 33, line 33, change "7 and 18" to -- 7 and 13 --

Column 33, line 34, change "mg" to -- µg --

Column 36, line 39, change "dienoid" to -- dienoic --

Column 37, line 29, change "dienoid" to -- dienoic --

Column 40, line 16, change "2060" to -- 2860 --

Column 43, lines 7 and 31, change "[3,3,0,0$^{2.8}$]" to -- [3,3,0,0$^{2,8}$] --

Column 45, line 64, change "Preceeding" to -- Proceeding --

Column 47, line 68, change "1625" to -- 1626 --

Column 48, line 9, change "2900" to -- 2960 --

Column 48, line 13, change "-34" to -- -84 --

Column 48, line 32, change "0.93" to -- 0.98 --

Column 50, line 33, change "Exaample" to -- Example --

Column 50, line 62, change "preapred" to -- prepared --

Column 51, line 43, change "dionoic" to -- dienoic --

Column 51, line 67, change "5.56" to -- 5.65 --

UNITED STATES PATENT AND TRADEMARK OFFICE
CERTIFICATE OF CORRECTION

PATENT NO. : 4,479,966
DATED : Oct. 30, 1984
INVENTOR(S) : Hayashi et al.

It is certified that error appears in the above-identified patent and that said Letters Patent is hereby corrected as shown below:

Column 52, line 38, change "as" to -- a --

Column 52, line 56, change "pounts" to -- pounds --

Column 54, line 20, change "3660" to -- 3360 --

Column 55, line 4, change "6,13" to -- 5,13 --

Column 56, line 6, change "0.85" to -- 0.35 --

Column 56, line 27, change "board" to -- broad --

Column 56, line 41, change " " " to -- $\delta$ --

Column 58, line 7, change "23.4" to -- 28.4 --

Column 59, line 29, change "-1-" to -- -2- --

Column 60, line 20, change "0.25" to -- 0.27 --

Column 62, line 32, change "bicycle" to -- bicyclo --

Column 65, line 43, change "$cm^1$" to -- $cm^{-1}$ --

Column 66, line 10, change "11$\beta$" to -- 11$\alpha$ --

Column 66, line 67, change "67" to -- $\delta$ --

Column 67, line 64, change "hydogen" to -- hydrogen --

Column 69, line 43, change "ar" to -- an --

Column 71, line 22, change "or" to -- to --

UNITED STATES PATENT AND TRADEMARK OFFICE
CERTIFICATE OF CORRECTION

PATENT NO. : 4,479,966

DATED : Oct. 30, 1984

INVENTOR(S) : Hayashi et al.

It is certified that error appears in the above-identified patent and that said Letters Patent is hereby corrected as shown below:

Column 72, line 58, change the pertinent portion of the formula from "$R^4$" to -- $R^6$ --

Signed and Sealed this

Fifth Day of November 1985

[SEAL]

Attest:

DONALD J. QUIGG

Attesting Officer

Commissioner of Patents and Trademarks